(12) United States Patent
Yamamoto et al.

(10) Patent No.: US 12,275,965 B2
(45) Date of Patent: Apr. 15, 2025

(54) NUCLEASE DOMAIN AND USE THEREOF

(71) Applicant: HIROSHIMA UNIVERSITY, Higashi-Hiroshima (JP)

(72) Inventors: Takashi Yamamoto, Higashi-Hiroshima (JP); Tetsushi Sakuma, Higashi-Hiroshima (JP); Masakazu Saito, Higashi-Hiroshima (JP)

(73) Assignee: HIROSHIMA UNIVERSITY, Higashi-Hiroshima (JP)

( * ) Notice: Subject to any disclaimer, the term of this patent is extended or adjusted under 35 U.S.C. 154(b) by 966 days.

(21) Appl. No.: 17/271,481

(22) PCT Filed: Aug. 23, 2019

(86) PCT No.: PCT/JP2019/033045
§ 371 (c)(1),
(2) Date: Feb. 25, 2021

(87) PCT Pub. No.: WO2020/045281
PCT Pub. Date: Mar. 5, 2020

(65) Prior Publication Data
US 2021/0332339 A1 Oct. 28, 2021

(30) Foreign Application Priority Data
Aug. 27, 2018 (JP) ................ 2018-158710

(51) Int. Cl.
*C12N 9/22* (2006.01)
*C12N 15/63* (2006.01)
*C12N 15/90* (2006.01)

(52) U.S. Cl.
CPC .............. *C12N 9/22* (2013.01); *C12N 15/63* (2013.01); *C12N 15/907* (2013.01); *C12N 2800/80* (2013.01)

(58) Field of Classification Search
CPC ........ C12N 9/22; C12N 15/63; C12N 15/907; C12N 2800/80; C12N 15/09; C07K 2319/80
See application file for complete search history.

(56) References Cited

U.S. PATENT DOCUMENTS

| | | | |
|---|---|---|---|
| 9,410,134 B2 | 8/2016 | Kuhn | |
| 10,975,393 B2 * | 4/2021 | Miller | C12N 9/22 |
| 2017/0152527 A1 | 6/2017 | Paschon et al. | |
| 2018/0087072 A1 * | 3/2018 | Miller | C12N 9/14 |
| 2019/0169240 A1 | 6/2019 | Yamamoto et al. | |

FOREIGN PATENT DOCUMENTS

WO 2014/175284 A1 10/2014

OTHER PUBLICATIONS

Bhattacharya et al., Impact of genetic variation on three dimensional structure and function of proteins, 2017, PLoS One, vol. 12, Issue 3, pp. 1-22 (Year: 2017).*
Fenton et al., Rheostat positions: A new classification of protein positions relevant to pharmacogenomics, 2020, Medicinal Chemistry Research, vol. 29, pp. 1133-1146 (Year: 2020).*
Guo et al., Protein tolerance to random amino acid change, 2004, PNAS, vol. 101, No. 25, pp. 9205-9210 (Year: 2004).*
Handel et al., Expanding or Restricting the Target Site Repertoire of Zinc-finger Nucleases: The Inter-domain Linker as a Major Determinant of Target Site Selectivity, 2009, Molecular Therapy, vol. 17, No. 1, pp. 104-111 (Year: 2009).*
Sakuma et al., Repeating pattern of non-RVD variations in DNA-binding modules enhances TALEN activity, 2013, Scientific Reports, vol. 3, Issue 3379, pp. 1-8 (Year: 2013).*
Extended European Search Report, dated May 20, 2022, issued by the European Patent Office in European Application No. 19853370.5.
Database Protein [online], "hypothetical protein [Clostridium botulinum]", WP_050491628, 579 aa, linear BCT Aug. 7, 2015 (1 page total).
Database UniProt [online], "SubName: Full=Uncharacterized protein {ECO : 0000313|EMBL:KSU87972.1}", AOAV8JLM2, Mar. 16, 2016, 585 AA (1 page total).
Communication, dated Mar. 11, 2021, issued by the International Bureau in International application No. PCT/JP2019/033045.
Eva-Maria Handel et al., "Expanding or Restricting the Target Site Repertoire of Zinc-finger Nucleases: The Inter-domain Linker as a Major Determinant of Target Site Selectivity", *Molecular Therapy*, 2009, 17(1): 104-111.
S. G. Dastager et al., "hypothetical protein AS180_10220 [*Bacillus* sp. SGD-V-76]", Database GenBank [online], Accession No. KSU87972.1, Dec. 2015, CSIR-National Chemical Laboratory, National Collection of Industrial Microorganisins (NCIM), India, 2 pages.
S. G. Dastager et al., "*Bacillus* sp. SGD-V-76 contig031, whole genome shotgun sequence", Database GenBank [online]. Accession No. LNQP01000031.1, Dec. 2015, CSIR-National Chemical Laboratory, National Collection of Industrial Microorganisins (NCIM), 2 pages.
A. Poehlein e al., "[Clostridium] thermoalcaliphilum strain DSM 7309 CLOTH_contig000003, whole genome shotgun sequence", Database GenBank [online], Accession No. MZGW01000003. Mar. 1, 2017, Genomic and Applied Microbiology & Goettingen Genomics Laboratory, Georg-August-University Goettingen, Germany, 2 pages.
International Search Report for PCT/JP2019/033045, dated Oct. 15, 2019.

* cited by examiner

*Primary Examiner* — Jeffrey Stucker
*Assistant Examiner* — Brittney E Donoghue
(74) *Attorney, Agent, or Firm* — Sughrue Mion, PLLC

(57) ABSTRACT

The present invention provides an artificial nucleic acid-cleaving enzyme comprising: a nuclease domain which is a polypeptide containing an amino acid sequence set forth at positions 391 to 585 of SEQ ID NO: 1 or positions 389 to 579 of SEQ ID NO: 3, or a mutant polypeptide thereof; and a nucleic acid-binding domain.

10 Claims, 16 Drawing Sheets

Specification includes a Sequence Listing.

Fig.1B

```
FokI    LVKSELEEKKSELRHKLKYVPHEYIELIEIARNSTQDRILEMKVMEFFMKVYGYRGKHLG
ND1     LVKGEMEKKKSDLRHKLKHVPHEYIELIEIAQDSKQNRLFEFKVVEFLKEVYDYNGKHLG
ND2     IVKSSIEMSKANMRDNLQMLPHDYIELIEISQDPYQNRIFEMKVMDLFINEYGFSGSHLG
ND3     GIKSNISLLKDELRGQISHISHEYLSLIDLAFDSKQNRLFEMKVLELLVNEYGFKGRHLG
ND4     ISKTNILELKDKVRDKLKYVDHRYLALIDLAYDGTANRDFEIQTIDLLINELKFKGVRLG
                                             ▼ ▼           *
FokI    GSRKPDGAI-YTVGSPIDYGVIVDTKAYSGGYNLPIGQADEMQRYVEENQTRNKHINPNE
ND1     GSRKPDGAL-YTNGLRTDYGIILDTKAYKDGYSLPISQADEMQRYVDENNNRNAIINPNE
ND2     GSRKPDGAM-YAHG----FGVIVDTKAYKDGYNLPISQADEMERYVRENIDRNEHVNSNR
ND3     GSRKPDGIV-YSTTLEDNFGIIVDTKAYSEGYSLPISQADEMERYVRENSNRDEEVNPNK
ND4     ESRKPDGIISYNIN------GVIIDNKAYSTGYNLPINQADEMIRYIEENQTRDEKINSNK

FokI    WWKVYPSSVTEFKFLFVSGHFKGNYKAQLTRLNHITNCNGAVLSVEELLIGGEMIKAGTL
ND1     WWKVYPNSILDFKFLFVSGFFKGDYKKQLARVSNLTKRKGAVLSVEQLLLGGEKIKDGSL
ND2     WWNIFPEDTNEYKFLFVSGFFKGNFEKQLERISIDTGVQGGALSVEHLLLGAEYIKRGIL
ND3     WWENFSEEVKKYYFVFISGSFKGKFEEQLRRLSMTTGVNGSAVNVVNLLLGAEKIRSGEM
ND4     WWESFDEKVKDFNYLFVSSFFKGNFKNNLKHIANRTGVNGGAINVENLLYFAEELKAGRI

FokI    TLEEVRRK-FNNGEINF (SEQ ID NO:125)
ND1     TLEDVGDK-FNNDEIIF (SEQ ID NO:126)
ND2     TLYDFKNS-FLNKEIQF (SEQ ID NO:127)
ND3     TIEELERAMFNNSEFI- (SEQ ID NO:128)
ND4     SYLDSFKM-YNNDEIYL (SEQ ID NO:129)
```

Fig. 10

ZFA36-ZFA36 1st site

FokI (N=17)
(Reference) ACCATCTTCC---ACTCT-GAAGATGGA (SEQ ID NO:76)
wt 13/17 CAGCCACCATCTTCC---ACTCT-GAAGATGGACAGGT (SEQ ID NO:77)
+1 1/17 CAGCCACCATCTTCC---ACTCT-GAAGATGGACAGGT (SEQ ID NO:77)
+4 3/17 CAGCCACCATCTTCCACTCTCACTCT-GAAGATGGACAGGT (SEQ ID NO:78)

ND1 (N=14)
(Reference) ACCATCTCTTCC---ACTCTGAAGATGGA (SEQ ID NO:142)
wt 3/14 CAGCCACCATCTTCC---ACTCTGAAGATGGACAGGT (SEQ ID NO:79)
+1 1/14 CAGCCACCATCTTCCA---ACTCTGAAGATGGACAGGT (SEQ ID NO:80)
+2/Δ1 2/14 CAGCCACCATCTTCCACT--CTCTGAAGATGGACAGGT (SEQ ID NO:81)
+6 1/14 CAGCCACCATCTTCCACTCTGAAGATGGAGGA---GAAGATGGACAGGT (SEQ ID NO:82)
Δ2 1/14 CAGCCACCATCTTCC-----TCT-GAAGATGGACAGGT (SEQ ID NO:83)
Δ8 1/14 CAGCC-----C---ACTCTGAAGATGGACAGGT (SEQ ID NO:84)

ND2 (N=13)
(Reference) ACCATCTTCCACTCT-GAAGATGGA (SEQ ID NO:142)
wt 9/13 CAGCCACCATCTTCCACTCT-GAAGATGGACAGGT (SEQ ID NO:85)
+1 1/13 CAGCCACCATCTTCCACTCT-TGAAGATGGACAGGT (SEQ ID NO:86)
+2 1/13 CAGCCACCATCTTCCACTCTCTG-AAGATGGACAGGT (SEQ ID NO:87)
Δ2 1/13 CAGCCACCATCTTCC-----TCT-GAAGATGGACAGGT (SEQ ID NO:88)
Δ4 1/13 CAGCCACCATCTCT--TCT-GAAGATGGACAGGT (SEQ ID NO:89)

ND3 (N=15)
(Reference) ACCATCCACCATCTCTGAAGATGGA (SEQ ID NO:142)
wt 15/15 CAGCCACCATCTCCACTCTGAAGATGGACAGGT (SEQ ID NO:90)

ND4 (N=16)
(Reference) ACCATCTTCCACTCTGAAGATGGA (SEQ ID NO:142)
wt 16/16 CAGCCACCATCTTCCACTCTGAAGATGGACAGGT (SEQ ID NO:91)

ZFA36-ZFA36 2nd site

FokI (N=20)
(Reference) ACCTACCAGTTCAA---GAAGA--GAAGATGGC (SEQ ID NO:143)
wt 13/20 ACCTACCATCTTCAA---GAAGA--GGAAGATGGCTTAAA (SEQ ID NO:92)
+2 1/20 ACCTACCATCTTCAA---GAAGA---GAAGATGGCTTAAA (SEQ ID NO:93)
+4 3/20 ACCTACCATCTTCAAGATGGAAGA---GAAGATGGCTTAAA (SEQ ID NO:94)
+5 1/20 ACCTACCATCTTCAAGATGGAAGAGGA---GAAGATGGCTTAAA (SEQ ID NO:95)
+231 1/20 ACCTACCATCTTCAA(231bp)AAGATGGCTTAAA (SEQ ID NO:144,145)
Δ2 1/20 AGTTACCATCTTCAA------GATGGCTTAAA (SEQ ID NO:96)

ND1 (N=17)
(Reference) ACCATCTTCAA---GAAGAAGAAGATGGC (SEQ ID NO:143)
wt 4/17 ACCTACCATCTTCAA---GAAGAAGAAGATGGCTTAAA (SEQ ID NO:98)
+2 6/17 ACCTACCATCTTCAA---GAAGAAGAAGAAGATGGCTTAAA (SEQ ID NO:99)
+3 1/17 ACCTACCATCTTCAACT---GAAGAAAAGATGGCTTAAA (SEQ ID NO:100)
+6 3/17 ACCTACCATCTTCAACTCTCGAAGAAAGATGGCTTAAA (SEQ ID NO:101)
Δ2 1/17 ACCTACCATCTTCAA------TGAAAGATGGCTTAAA (SEQ ID NO:102)

ND2 (N=16)
(Reference) ACCATCTTCAA---GAAGAAGAAGATGGC (SEQ ID NO:143)
wt 7/16 ACCTACCATCTTCAA---GAAGAAGAAGAAGATGGCTTAAA (SEQ ID NO:103)
+1 1/16 ACCTACCATCTTCAA---AGAAGAAAGATGGCTTAAA (SEQ ID NO:104)
+2 2/16 ACCTACCATCTTCAA---GAAGAAGAAAGATGGCTTAAA (SEQ ID NO:105)
+4 5/16 ACCTACCATCTTCAA---GAAGAAGAAGAAGATGGCTTAAA (SEQ ID NO:106)
+71 1/16 ACCTACCATCTTCAA(71bp)AAGAAGAAGATGGCTTAAA (SEQ ID NO:146,147)

ND3 (N=16)
(Reference) ACCATCTTCAA---GAAGAAGAAGATGGC (SEQ ID NO:143)
wt 13/16 ACCTACCATCTTCAA---GAAGAAGAAGAAGATGGCTTAAA (SEQ ID NO:108)
+2 1/16 ACCTACCATCTTCAA---AAGAAGAAGAAGAAGATGGCTTAAA (SEQ ID NO:109)
+8 1/16 ACCTACCATCTTC-----AGTTGGCTTAAA (SEQ ID NO:110)

ND4 (N=14)
(Reference) ACCATCTTCAA---GAAGAAGAAGATGGC (SEQ ID NO:143)
wt 14/14 ACCTACCATCTTCAAGAAGAAGAAGAAGATGGCTTAAA (SEQ ID NO:112)

NUCLEASE DOMAIN AND USE THEREOF

CROSS REFERENCE TO RELATED APPLICATIONS

This application is a National Stage of International Application No. PCT/JP2019/033045 filed on Aug. 23, 2019, which claims priority under U.S.C. § 119(a) to Japanese Patent Application No. JP2018-158710 filed on Aug. 27, 2018.

INCORPORATION BY REFERENCE OF SEQUENCE LISTING

The content of the electronically submitted sequence listing, file name: Q261402_Substitute_Sequence_Listing.txt; size: 89.6 KB; and date of creation: Jun. 30, 2024, filed herewith, is incorporated herein by reference in its entirety.

TECHNICAL FIELD

The present invention relates to a novel nuclease domain and an artificial nucleic acid-cleaving enzyme containing the nuclease domain.

BACKGROUND ART

In recent years, as a genome editing tool, nucleases that specifically recognize a target sequence and can cleave in the vicinity thereof have become available, such as zinc-finger nuclease (ZFN), transcription activator-like effector nuclease (TALEN), and CRISPR/Cas (clustered regularly interspaced short palindromic repeat/CRISPR-associated) system. These nucleases include a nucleic acid-binding domain and a nucleic acid-cleaving domain, and can result in a DNA double-strand break (DSB) at a specific base sequence of genomic DNA. As the repair of DSB brought about by these nucleases, non-homologous end joining (NHEJ) and homologous recombination (HR), which are prone to repair errors, are known. When repairing DSB, cells mainly use the NHEJ pathway for repair, so that repair errors are likely to occur, frame shifts occur, and as a result, gene function is lost. In this way, genome editing technology that can perform gene disruption and the like using the mechanism possessed by cells is being widely used in life science such as disease research and application to agricultural products.

In a ZFN and a TALEN, a FokI nuclease domain (hereinafter also referred to as "FokI-ND") is usually used as a nucleic acid-cleaving domain. The FokI-ND has been shown to have the ability to bind to nucleic acids, but does not recognize the base sequence and cleaves the target nucleic acid by forming a dimer. Therefore, a ZFN and a TALEN require two target sequences of nucleic acid-binding domain, and FokI-ND acts in the spacer sequence sandwiched between the two target sequences to bring about DSB. In a ZFN, the two target sequences are referred to as a target half-site L and a target half-site R.

A ZFN is composed of a FokI-ND, a nucleic acid-binding domain made up of zinc-finger protein (ZFP), and an intermolecular linker connecting them. In a ZFN, there are strong restrictions due to the length of the spacer sequence and the properties of the linker, and it is necessary to devise the design. Therefore, as a technique related to ZFNs, modification of the length of the spacer sequence and the linker has been reported (NPL 1).

In addition, a fusion protein of a nucleic acid-binding domain such as TALE and a nuclease domain derived from *Clostridium* spec. 7_2_43 FAA strain has been reported (PTL 1).

CITATION LIST

Patent Literature

[PTL 1] U.S. Pat. No. 9,410,134

Non Patent Literature

[NPL 1] Handel, E. M., Alwin, S. and Cathomen, T. (2009) Expanding or restricting the target site repertoire of zinc-finger nucleases: the inter-domain linker as a major determinant of target site selectivity. Mol Ther, 17, 104-111

SUMMARY OF INVENTION

Technical Problem

An object of the present invention is to provide a novel nuclease domain having high cleavage activity and cleavage efficiency as well as fewer restrictions due to a target sequence, spacer sequence, linker sequence, and the like, and an artificial nucleic acid-cleaving enzyme containing the nuclease domain.

Solution to Problem

The present inventors searched for a nuclease domain different from FokI-ND, which is currently used as a standard nucleic acid-cleaving domain for genome editing enzymes, and have found as a result a novel nuclease domain that surpasses the existing FokI-ND in functionality such as cleavage activity, specificity, cytotoxicity, and target sequence selectivity. Thus, the present invention has been completed.

That is, the present invention provides the following aspects.

(1) An artificial nucleic acid-cleaving enzyme comprising:
a nuclease domain which is a polypeptide containing an amino acid sequence set forth at positions 391 to 585 of SEQ ID NO: 1 or positions 389 to 579 of SEQ ID NO: 3, or a mutant polypeptide thereof; and a nucleic acid-binding domain.

(2) The artificial nucleic acid-cleaving enzyme according to (1) above, further comprising: a linker located between the nuclease domain and the nucleic acid-binding domain.

(3) The artificial nucleic acid-cleaving enzyme according to (1) or (2) above, wherein the nucleic acid-binding domain contains a zinc finger, TALE, CRISPR/Cas, or PPR.

(4) An isolated nucleic acid comprising: a nucleic acid sequence encoding the artificial nucleic acid-cleaving enzyme according to any one of (1) to (3) above.

(5) A vector comprising: the nucleic acid according to (4) above, or a transcription product or translation product thereof.

(6) A method for modifying a target nucleic acid, comprising: introducing into a cell the artificial nucleic acid-cleaving enzyme according to any one of (1) to (3) above, the nucleic acid according to (4) above, or the vector according to (5) above.

(7) The method according to (6) above, wherein the artificial nucleic acid-cleaving enzyme, nucleic acid, or vector is two or more kinds of artificial nucleic acid-cleaving enzymes, a nucleic acid encoding the two or more kinds of artificial nucleic acid-cleaving enzymes, or a vector containing the nucleic acid, a transcription product thereof, or a translation product thereof.

(8) A kit for modifying a target nucleic acid, comprising: the artificial nucleic acid-cleaving enzyme according to any one of (1) to (3) above, the nucleic acid according to (4) above, or the vector according to (5) above.

(9) The kit according to (8) above, wherein the artificial nucleic acid-cleaving enzyme, nucleic acid, or vector is two or more kinds of artificial nucleic acid-cleaving enzymes, a nucleic acid encoding the two or more kinds of artificial nucleic acid-cleaving enzymes, or a vector containing the nucleic acid, a transcription product thereof, or a translation product thereof.

(10) A polypeptide containing an amino acid sequence set forth at positions 391 to 585 of SEQ ID NO: 1 or positions 389 to 579 of SEQ ID NO: 3, or a mutant polypeptide thereof.

(11) An isolated nucleic acid comprising: a nucleic acid sequence encoding the polypeptide or the mutant polypeptide thereof according to (10) above.

(12) A vector comprising: the nucleic acid according to (11) above, or a transcription product thereof, or a translation product thereof.

Advantageous Effects of Invention

The nuclease domain according to the present invention provides a nucleic acid cleaving action superior to the conventional FokI-ND in terms of functionality such as cleavage activity, specificity, and target sequence selectivity. By binding the nuclease domain of the present invention to a nucleic acid-binding domain, a nucleic acid-cleaving enzyme having high activity and flexibility in the target sequence is provided, which specifically cleaves the target sequence. Such a nucleic acid-cleaving enzyme is very useful as a genome editing tool.

BRIEF DESCRIPTION OF DRAWINGS

FIG. 1B shows an amino acid sequence alignment of the FokI nuclease domain homolog. Amino acid sequences were aligned using MAFFT. The amino acids that define the heterodimer nuclease domain and the corresponding point mutations are indicated by arrows, asterisks, and colons. In the figure, "Fok1" means FokI-ND.

FIG. 6B The results of the SSA reporter assay performed in Example 6 are shown, where − indicates that the ZFN plasmid is absent. The data are shown as mean±SEM (n=3).

FIG. 7A hPGRN_ZFL1-6bp-hPGRN_ZFL1 reporter. FIG. 7B ZFA36-6bp-ZFA36 reporter. In the figure, "FokI" means FokI-ND.

FIG. 9A ZFL1-FokI-DDD and appropriate nuclease domain.
FIG. 9B ZFL1-ND1-DDD and appropriate nuclease domain.
FIG. 9C ZFL1-ND2-DDD and appropriate nuclease domain. The data are shown as mean±SEM (n=3). In the figure, "FokI" means FokI-ND.

FIG. 10 shows the results of sequence analysis of the target site performed in Example 9. In the figure, "FokI" means FokI-ND.

DESCRIPTION OF EMBODIMENTS

1. Novel Nuclease Domains

Figure 1A:
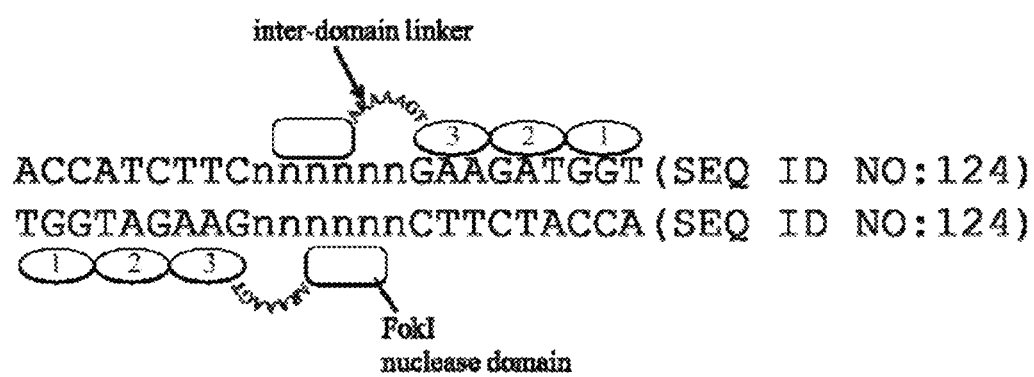
FIG. 1A is a schematic diagram of ZFA36-ND. The upper part shows that the two ZFN target sites are separated by a spacer sequence. The lower part shows that the ZFNs each contain three zinc finger molecules, a short 7-amino acid TGAAARA linker, and a FokI nuclease domain. When a pair of ZFNs binds to a target half site separated by a spacer sequence of a given length, the nuclease domain is dimerized and the nucleic acid can be cleaved.

In order to develop a novel nuclease domain with higher performance than FokI-ND, the present inventors searched for homologous natural materials by protein-protein BLAST based on the amino acid sequence of FokI-ND. The present inventors selected several types from the homologous sequences having homology with FokI-ND in the range of 35% to 70% to further proceed with the analysis, and have found nuclease domain 1 (hereinafter referred to as "ND1") and nuclease domain 2 (hereinafter referred to as "ND2") having nuclease activity superior to that of FokI-ND.

The amino acid sequence of the full-length protein containing ND1 (derived from Bacillus SGD-V-76) is set forth in SEQ ID NO: 1, and its base sequence is set forth in SEQ ID NO: 2. The amino acid sequence of the full-length protein containing ND2 (derived from *Clostridium botulinum*) is set forth in SEQ ID NO: 3, and its base sequence is set forth in SEQ ID NO: 4. ND1 is typically a partial peptide corresponding to positions 391 to 585 of SEQ ID NO: 1, and ND2 is typically a partial peptide corresponding to positions 389 to 579 of SEQ ID NO: 3.

ND1 has an amino acid sequence identity of 70% with FokI-ND, and ND2 has an amino acid sequence identity of 57% with FokI-ND, both being novel polypeptides isolated for the first time in the present invention.

Therefore, the present invention provides a nuclease domain which is a polypeptide containing an amino acid sequence set forth at positions 391 to 585 of SEQ ID NO: 1 or positions 389 to 579 of SEQ ID NO: 3, or a mutant polypeptide thereof (hereinafter also referred to as "nuclease domain of the present invention"). The nuclease domain of the present invention includes a nuclease domain which is a polypeptide composed of an amino acid sequence set forth at positions 391 to 585 of SEQ ID NO: 1 or positions 389 to 579 of SEQ ID NO: 3, or a mutant polypeptide thereof. In other words, the present invention provides use of a polypeptide containing an amino acid sequence set forth at positions 391 to 585 of SEQ ID NO: 1 or positions 389 to 579 of SEQ ID NO: 3, or a mutant polypeptide thereof, for example a polypeptide composed of an amino acid sequence set forth at positions 391 to 585 of SEQ ID NO: 1 or positions 389 to 579 of SEQ ID NO: 3, or a mutant polypeptide thereof, as a nuclease domain.

In the present specification, a mutant polypeptide of a polypeptide containing an amino acid sequence set forth at positions 391 to 585 of SEQ ID NO: 1 or positions 389 to 579 of SEQ ID NO: 3 is a polypeptide having an amino acid sequence similar to the amino acid sequence set forth at positions 391 to 585 of SEQ ID NO: 1 or positions 389 to 579 of SEQ ID NO: 3 and having nuclease activity. Examples of the mutant polypeptide include a polypeptide containing an amino acid sequence in which one to several amino acid residues are substituted, deleted, inserted, or added in the amino acid sequence set forth at positions 391 to 585 of SEQ ID NO: 1 or positions 389 to 579 of SEQ ID NO: 3 and having nuclease activity, and a polypeptide composed of an amino acid sequence in which one to several amino acids are substituted, deleted, inserted, or added in the amino acid sequence set forth at positions 391 to 585 of SEQ ID NO: 1 or positions 389 to 579 of SEQ ID NO: 3 and having nuclease activity. Here, "one to several" is, for example, 1 to 10, preferably 1 to 6, and is, for example, 1, 2, 3, 4, or 5.

In addition, as another example, the mutant polypeptide may be a polypeptide containing an amino acid sequence having at least 70%, at least 75%, at least 80%, at least 85%, at least 90%, at least 95%, and at least 98% sequence identity with the amino acid sequence set forth at positions 391 to 585 of SEQ ID NO: 1 or positions 389 to 579 of SEQ ID NO: 3 and having nuclease activity, for example may be a polypeptide composed of an amino acid sequence having at least 70%, at least 75%, at least 80%, at least 85%, at least 90%, at least 95%, and at least 98% sequence identity with the amino acid sequence set forth at positions 391 to 585 of SEQ ID NO: 1 or positions 389 to 579 of SEQ ID NO: 3 and having nuclease activity. In addition, further examples of the mutant polypeptide include a polypeptide containing an amino acid sequence encoded by a base sequence having at least 50%, at least 55%, at least 60%, at least 65%, at least 70%, at least 75%, at least 80%, at least 85%, at least 90%, at least 95%, and at least 98% sequence identity with the base sequence set forth at positions 1171 to 1755 of SEQ ID NO: 2 or positions 1165 to 1737 of SEQ ID NO: 4 and having nuclease activity, and a polypeptide composed of an amino acid sequence encoded by a base sequence having at least 50%, at least 55%, at least 60%, at least 65%, at least 70%, at least 75%, at least 80%, at least 85%, at least 90%, at least 95%, and at least 98% sequence identity with the base sequence set forth at positions 1171 to 1755 of SEQ ID NO: 2 or positions 1165 to 1737 of SEQ ID NO: 4 and having nuclease activity.

In the present invention, the "sequence identity" of an amino acid sequence is determined by comparing two sequences aligned to maximize sequence matching. Methods for determining the numerical value (%) of sequence identity are known to those skilled in the art. As an algorithm for obtaining optimum alignment and sequence identity, any algorithm known to those skilled in the art (such as BLAST algorithm and FASTA algorithm) may be used. The sequence identity of an amino acid sequence is determined using, for example, sequence analysis software such as BLASTP or FASTA.

Furthermore, the above-mentioned mutant polypeptide may preferably contain an amino acid sequence having aspartic acid at the position corresponding to position 483 in the amino acid sequence of FokI (hereinafter referred to as "D483") and/or arginine at the position corresponding to position 487 in the amino acid sequence of FokI (hereinafter referred to as "R487"). In addition, the above-mentioned mutant polypeptide may preferably contain an amino acid sequence having aspartic acid, aspartic acid, and lysine at positions corresponding to positions 450, 467 and 469 in the amino acid sequence of FokI (hereinafter referred to as "D450," "D467," and "K469," respectively). More preferably, the mutant polypeptide contains an amino acid sequence having D483 and/or R487 and having D450, D467, and K469. D483 and R487 are amino acid residues believed to be essential for FokI-ND to form a cleavage-active dimer, and are retained in the amino acid sequences of ND1 and ND2. Furthermore, regarding the catalytic site of FokI-ND, analysis using amino acid substitutions has revealed that D450 and D467 are involved in the cleavage of nucleic acids. Furthermore, the sequence including K469 in the vicinity of these amino acids is a motif found in EcoRI and EcoRV, and it has been clarified that these amino acids are involved in the cleavage activity of the phosphate diester bond. D450, D467, and K469 are retained in the amino acid sequences of ND1 and ND2.

In addition, the above-mentioned mutant polypeptide may contain aspartic acid at positions corresponding to positions 483, 487, and 496 in the amino acid sequence of FokI (hereinafter referred to as "D483, D487, and D496") (hereinafter also referred to as "DDD-type mutant"), or may contain arginine at positions corresponding to positions 483, 487, and 537 in the amino acid sequence of FokI (hereinafter referred to as "R483, R487, and R537") (hereinafter, also referred to as "RRR-type mutant"), so that the nuclease domain of the present invention forms a heterodimer upon nucleic acid cleavage.

The chain length of the polypeptide containing an amino acid sequence set forth at positions 391 to 585 of SEQ ID NO: 1 or positions 389 to 579 of SEQ ID NO: 3 or the mutant polypeptide of the present invention is usually 500 amino acids or less, for example, 400 amino acids or less, 300 amino acids or less, or 200 amino acids or less.

Further, in the present specification, the above-mentioned mutant polypeptides also include polypeptides containing modified amino acids and/or unnatural amino acids. The modified amino acids include, but are not limited to, methylation, esterification, amidation, acetylation, alkylation, halogenation, and the like. The modified amino acids and the unnatural amino acids can be introduced by a known method.

The nuclease domain of the present invention has nuclease activity equal to or higher than that of FokI-ND. For example, the nuclease domain of the present invention has at least 0.8 times, at least 0.9 times, at least 1 times, at least 1.3 times, at least 1.5 times, at least 1.8 times, at least 2 times, at least 2.3 times, at least 2.5 times, at least 2.8 times, at least 3 times, at least 3.3 times, at least 3.5 times, at least 3.8 times, or at least 4 times more nuclease activity than FokI-ND. The nuclease activity can be confirmed by methods known in the art. For example, the nuclease domain may be incorporated into a ZFN system, and confirmed by measuring nucleic acid cleavage activity, such as DNA cleavage activity, by the SSA (single-strand annealing) method and the Cel-I method.

As described later, the nuclease domain of the present invention has properties different from those of FokI-ND in the flexibility in the selection of a linker in the artificial nucleic acid-cleaving enzyme and the flexibility in the selection of a spacer as the target cleavage site (Example 5). In addition, even when a Sharkey mutation known to cause an increase in activity in FokI-ND was introduced into the nuclease domain of the present invention, no increase in activity was observed (Example 6). In addition, unlike FokI-ND, the ND1 of the present invention did not decrease in nuclease activity even when a heterodimer was formed (Example 7). Thus, the nuclease domain of the present invention is a nuclease domain that has superior properties and/or different properties as compared with conventional FokI-ND.

The nuclease domain of the present invention may be an isolated nuclease domain. The present invention also provides an isolated nucleic acid encoding the nuclease domain of the present invention. As used herein, the term "isolated" refers to a state separated from the natural world or a living body.

2. Artificial Nucleic Acid-Cleaving Enzyme

The artificial nucleic acid-cleaving enzyme of the present invention includes the nuclease domain and nucleic acid-binding domain of the present invention. The artificial nucleic acid-cleaving enzyme binds to a target sequence on a nucleic acid via a nucleic acid-binding domain, and cleaves the nucleic acid at a target cleavage site by the nuclease domain. Therefore, the artificial nucleic acid-cleaving enzyme is a sequence-specific nucleic acid-cleaving enzyme capable of specifically cleaving a target site in a nucleic acid.

In the present specification, the "nucleic acid" includes both DNA and RNA. Examples of the nucleic acid cleaved by the artificial nucleic acid-cleaving enzyme of the present invention include double-stranded DNA, single-stranded DNA, and single-stranded RNA. Examples of the DNA include, but are not limited to, eukaryotic nuclear genomic DNA, mitochondrial DNA, plastid DNA, prokaryotic genomic DNA, phage DNA, plasmid DNA, and the like. Preferably, the artificial nucleic acid-cleaving enzyme of the present invention cleaves double-stranded DNA on the genome. Examples of the RNA include, but are not limited to, single-stranded RNA, double-stranded RNA, or a DNA-RNA hybrid double strand composed of single-stranded DNA and single-stranded RNA.

The nucleic acid-binding domain may be a protein domain that specifically binds to an arbitrary nucleic acid sequence (target sequence), and examples thereof include, but are not limited to, zinc fingers, TALE, CRISPR/Cas (complex of Cas protein and guide RNA), pentatricopeptide repeat (PPR), and the like, and DNA-binding domains containing combinations thereof. Examples of CRISPR/Cas include CRISPR-Cas9, CRISPR-Cpf1 (Cas12a), CRISPR-Cas12b, CRISPR-CasX (Cas12e), CRISPR-Cas14, CRISPR-Cas3, and the like. The nucleic acid-binding domain containing zinc fingers may preferably contain two or more zinc fingers, and examples thereof may include, but are not limited to, a zinc finger array composed of 3 to 9 zinc fingers (hereinafter also referred to as "ZFA"). It is known that one zinc finger recognizes a three-base sequence, for example, a zinc finger that recognizes GNN, ANN, CNN, or the like. The CRISPR/Cas preferably includes Cas with inactivated nuclease activity, such as dCas (Cas with inactivated nuclease activity, such as dCas9). Nucleic acid-binding domains are appropriately designed by those skilled in the art to bind to the desired target sequence. Note that in the present specification, "CRISPR/Cas" means a complex of a guide RNA and a Cas protein, and the guide RNA recognizes and binds to a target sequence.

In the artificial nucleic acid-cleaving enzyme of the present invention, the nuclease domain and the nucleic acid-binding domain may be directly linked or may be linked via a linker. The linker is composed of, for example, two or more amino acid residues, and the length thereof is not particularly limited, but may be, for example, a length of 2 to 20 amino acids, for example 2, 4, 6, 8, 9, 9, 12, 16, or 20 amino acids. The type of linker is not particularly limited either, and examples thereof include TGAAARA, GS, RPGEKP, TGPGAAARA, and the like. The presence or absence of a linker and the length and type of the linker are appropriately selected by those skilled in the art in consideration of the type and the like of the nucleic acid-binding domain. It is known that the nuclease activity of conventional ZFNs including FokI-ND is greatly affected by the linker sequence connecting ZF and FokI-ND, but in the case of the artificial nucleic acid-cleaving enzyme of the present invention, the dependence of its nuclease activity on the linker sequence is lower than that of the conventional ZFNs. In particular, in ND1, almost no decrease in nuclease activity was observed by changing the linker sequence (Example 5). Therefore, the artificial nucleic acid-cleaving enzyme of the present invention has high flexibility in linker sequence.

The target sequence of the artificial nucleic acid-cleaving enzyme of the present invention is an arbitrary sequence on the nucleic acid. The target sequence is preferably two sequences sandwiching a spacer sequence. The length of the spacer sequence, the length of the target sequences, and the base sequences are not particularly limited. Those skilled in the art can appropriately set target sequences having desired lengths and composed of base sequences. The two target sequences may be palindromic sequences or non-palindromic sequences with each other. When the two target sequences are non-palindromic sequences, two kinds of artificial nucleic acid-cleaving enzymes targeting the respective sequence are prepared. Furthermore, in the case of using a nucleic acid-binding domain containing CRISPR/Cas, sequences located in the vicinity of the protospacer adjacent motif (PAM) sequence are selected as the target sequences. That is, the target sequences are set so that the PAM is present outside of both target sequences or in the spacer sequence. The target sequences may be either a double-stranded sequence or a single-stranded sequence. In addition, in this specification, "vicinity" includes both adjacent positions or near positions.

In the artificial nucleic acid-cleaving enzyme of the present invention, when the nucleic acid-binding domain binds to a target sequence on a nucleic acid, the nuclease domain cleaves the nucleic acid at the target cleavage site. The target cleavage site is in or near the spacer sequence adjacent to the target sequences. The length of the spacer array is not particularly limited, and examples thereof include 1 to 20 bp, preferably 3 to 8 bp, and more preferably 5 to 7 bp. In the case of conventional ZFNs including FokI-ND, it is known that the optimum spacer length is 6 bp, and its nuclease activity is greatly affected by the spacer length, but in the case of the artificial nucleic acid-cleaving enzyme of the present invention, the spacer length is more flexible than that of the conventional ZFNs. The artificial nucleic acid-cleaving enzyme of the present invention exhibits high cleaving activity even for short spacers and long spacers by changing the linker length (Example 5). On the other hand, in conventional ZFNs including FokI-ND, even when the linker length is changed, the cleavage activity is significantly lowered for spacers shorter or longer than the optimum spacer length. Since the spacer length defines the distance between recognition sequences, the artificial nucleic acid-cleaving enzyme of the present invention provides a wide choice of target cleavage sites and recognition sequences due to the high flexibility of spacer length.

The artificial nucleic acid-cleaving enzyme of the present invention can be produced in vitro or in vivo by a method known in the art. Examples thereof include a method of artificial synthesis based on amino acid sequence information, and a method in which a nucleic acid encoding the artificial nucleic acid-cleaving enzyme of the present invention or each nucleic acid encoding the nuclease domain and nucleic acid-binding domain of the present invention is artificially synthesized, inserted into a suitable expression vector, and then introduced into a suitable host cell to express the artificial nucleic acid-cleaving enzyme in the cell. Alternatively, a method can be mentioned in which a nucleic acid encoding the artificial nucleic acid-cleaving enzyme of the present invention is synthesized by in-vitro or in-vivo translation to synthesize a protein, which is introduced into a suitable cell to allow the artificial nucleic acid-cleaving enzyme to act in the cell, or an RNA encoding the artificial nucleic acid-cleaving enzyme of the present invention is synthesized by in-vitro transcription, introduced into a suitable host cell to allow the artificial nucleic acid-cleaving enzyme to act in the cell. The expression vector is not particularly limited, and may be selected from vectors used in the art. Examples thereof include plasmid vectors, viral vectors, phage vectors, phagemid vectors, BAC vectors, YAC vectors, MAC vectors, HAC vectors, and the like.

The host cell is not particularly limited, and examples thereof include prokaryotes such as *Escherichia coli*, actinomycetes, and archaea, eukaryotes such as yeast, sea urchin, silkworm, zebrafish, mouse, rat, frog, tobacco, *Arabidopsis thaliana*, and rice, and cultured cells.

A further aspect of the present invention also provides an isolated nucleic acid containing a nucleic acid sequence encoding the artificial nucleic acid-cleaving enzyme of the present invention, as well as a transcription product and translation product of the nucleic acid. The above nucleic acid may be an isolated nucleic acid composed of a nucleic acid sequence encoding the artificial nucleic acid-cleaving enzyme of the present invention. In addition, codon optimization may be performed. In the present specification, "nucleic acid" includes both DNA and RNA.

3. Method for Modifying Target Nucleic Acid

When the artificial nucleic acid-cleaving enzyme of the present invention is introduced into a cell, the enzyme cleaves the target site on the nucleic acid in the cell, and the cleavage is then repaired by non-homologous end joining (NHEJ), homologous recombination (HR), or the like. At this time, in the repair by NHEJ as the main repair pathway, one or more mutations are inserted into the cleavage site to modify the nucleic acid. Therefore, a further aspect of the present invention provides a method for modifying a target nucleic acid, including introducing into a cell the artificial nucleic acid-cleaving enzyme of the present invention or a nucleic acid encoding the artificial nucleic acid-cleaving enzyme. The enzyme or nucleic acid described above may be a transcription product of the nucleic acid or a translation product thereof. The nucleic acid may also be codon-optimized for high expression in the cell. In addition, in the present specification, "modification" includes deletion, insertion, or substitution of at least one nucleotide, or a combination thereof. Also, in the present specification, the term "mutation" used with respect to nucleic acids means a nucleotide deletion, insertion, or substitution.

The introduction of the above-mentioned enzyme or nucleic acid into cells may be physical introduction, introduction via infection of a virus or an organism, or the like, and various methods known in the art can be used. Examples of the physical introduction method include, but are not limited to, an electroporation method, a particle gun method, a microinjection method, a lipofection method, a protein transduction method, and the like. Examples of the introduction method via infection of a virus or an organism include, but are not limited to, virus transduction, *Agrobacterium* method, phage infection, conjugation, and the like. The above introductions involve appropriate use of vectors. The vectors may be appropriately selected according to the type of cell for introduction, and examples thereof include, but are not limited to, plasmid vectors, viral vectors, phage vectors, phagemid vectors, BAC vectors, YAC vectors, MAC vectors, HAC vectors, and the like. Examples also include vectors such as liposomes and lentiviruses capable of carrying translation products (proteins) and transcription products (mRNAs), and peptide vectors such as cell-permeable peptides capable of introducing fused or bound molecules into cells.

Therefore, a further aspect of the present invention provides a vector containing a nucleic acid encoding the artificial nucleic acid-cleaving enzyme of the present invention, or a vector containing a transcription product of the nucleic acid or a translation product thereof. The vector containing a transcription product of the nucleic acid or a translation product thereof includes those transcribed by the nucleic acid in the vector containing the nucleic acid, and those in which the translation product is produced.

The above-mentioned cells may be either prokaryotic cells or eukaryotic cells, and are not particularly limited. Examples thereof include bacteria, archaea, yeast, plant cells, insect cells, and animal cells (such as human cells, non-human cells, non-mammalian vertebrate cells, and invertebrate cells). The cells may also be in-vivo cells, isolated cells, primary cells, or cultured cells. The cells may also be somatic cells, germ cells, or stem cells.

Specifically, examples of prokaryotes from which the above cells are derived include *Escherichia coli*, actinomycetes, archaea, and the like. In addition, examples of eukaryotes from which the above cells are derived include fungi such as yeast, mushrooms, and molds, echinoderms such as sea urchins, sea stars, and sea cucumbers, insects such as silkworms and flies, fish such as tuna, bream, pufferfish, and zebrafish, rodents such as mice, rats, guinea pigs, hamsters, and squirrels, even-toed ungulates such as cows, wild boars, pigs, sheep, and goats, odd-toed ungulates such as horses, reptiles such as lizards, amphibians such as frogs, Lagomorphs such as rabbits, Carnivora such as dogs, cats, and ferrets, birds such as chickens, ostriches, and quails, and plants such as tobacco, *Arabidopsis thaliana*, rice, corn, banana, peanut, sunflower, tomato, rapeseed, wheat, barley, potato, soybean, cotton, and carnation. Examples of the "animal cells" include embryonic cells of embryos at various stages (such as 1-cell stage embryos, 2-cell stage embryos, 4-cell stage embryos, 8-cell stage embryos, 16-cell stage embryos, and mulberry stage embryos); stem cells such as induced pluripotent stem (iPS) cells, embryonic stem (ES) cells, hematopoietic stem cells; somatic cells such as fibroblasts, hematopoietic cells, neurons, muscle cells, osteocytes, hepatocytes, pancreatic cells, brain cells, and kidney cells; fertilized eggs, and the like.

The target nucleic acid may be any gene in the genomic DNA in the cell or DNA in an extra-gene region. In order to cleave the target sequence in the target nucleic acid, the artificial nucleic acid-cleaving enzyme of the present invention is designed so that the nucleic acid-binding domain contained in the artificial nucleic acid-cleaving enzyme of the present invention binds to a sequence in the vicinity of the target sequence (selected as a target sequence of the nucleic acid-binding domain). As a result, the desired sequence in the target nucleic acid is cleaved, for example, the expression of the gene is reduced or eliminated, or the function of the gene is reduced or no function is expressed.

In the target nucleic acid modification method of the present invention, a donor polynucleotide may be introduced into cells in addition to the above-mentioned artificial nucleic acid-cleaving enzyme. The donor polynucleotide contains at least one donor sequence containing the modification desired to be introduced at the target cleavage site. The donor polynucleotide can be appropriately designed by those skilled in the art based on techniques known in the art. When a donor polynucleotide is present in the target nucleic acid modification method of the present invention, homologous recombination takes place at the target cleavage site, and the donor polynucleotide is inserted into the site or the site is replaced with the donor sequence. As a result, the desired modification is introduced at the target cleavage site.

In the absence of donor polynucleotide in the target nucleic acid modification method of the present invention, the target cleavage site is repaired primarily by non-homologous end joining (NHEJ). Since NHEJ is error-prone, deletions, insertions, or substitutions of at least one nucleotide, or a combination thereof, can occur during repair of the cleavage. In this way, the nucleic acid is modified at the target cleavage site.

In the target nucleic acid modification method of the present invention, two or more kinds of the above-mentioned artificial nucleic acid-cleaving enzyme may be introduced into cells. Examples of the two or more kinds of artificial nucleic acid-cleaving enzymes include two or more kinds of artificial nucleic acid-cleaving enzymes with different nucleic acid-binding domains, two or more kinds of artificial nucleic acid-cleaving enzymes with different nuclease domains, two or more kinds of artificial nucleic acid-cleaving enzymes with different nuclease domains and nucleic acid-binding domains, two or more kinds of artificial nucleic acid-cleaving enzymes with different linker sequences, and the like. The two or more kinds of artificial nucleic acid-cleaving enzymes with different nucleic acid-binding domains include two or more kinds of artificial nucleic acid-cleaving enzymes having different target sequences bound with nucleic acid-binding domains, and two or more kinds of artificial nucleic acid-cleaving enzymes having different kinds of nucleic acid-binding domains, and as an example, it is possible to mention two or more kinds of artificial nucleic acid-cleaving enzymes having different nuclease domains and different target sequences bound with nucleic acid-binding domains. For example, when no palindromic sequence exists in the region to be modified on the nucleic acid, two kinds of artificial nucleic acid-cleaving enzymes targeting different sequences may be used. In this case, into the nuclease domains of the two kinds of artificial nucleic acid-cleaving enzymes, a mutation that promotes heterodimer formation of the nuclease domains may be further introduced. This makes it possible to increase the recognition sequences of the artificial nucleic acid-cleaving enzymes and reduce the probability of off-targeting. Such mutations are, for example, substitutions into D483, D487, and D496 (hereinafter also referred to as "DDD-type mutations") and substitutions into R483, R487, and R537 (hereinafter also referred to as "RRR-type mutations"), where a DDD-type mutation is introduced into the nuclease domain of one artificial nucleic acid-cleaving enzyme, and an RRR-type mutation is introduced into the nuclease domain of the other artificial nucleic acid-cleaving enzyme. Note that if the nuclease domain sequence before the introduction of the mutation already has an amino acid residue of either the DDD-type mutation or the RRR-type mutation shown above, only the other amino acid substitutions need to be performed. The two kinds of nuclease domains introduced with a pair of mutations (such as DDD-type mutation and RRR-type mutation) that promote the formation of such heterodimers may be the same nuclease domains except for the above-mentioned mutations, or may be originally different nuclease domains before the above-mentioned mutations are introduced. For example, an artificial nucleic acid-cleaving enzyme containing a DDD-type mutant of ND1 and an artificial nucleic acid-cleaving enzyme containing an RRR-type mutant of ND1 may be used in the method of the present invention. In addition, for example, an artificial nucleic acid-cleaving enzyme containing a DDD-type mutant of ND2 and an artificial nucleic acid-cleaving enzyme containing an RRR-type mutant of ND1 may be used in the method of the present invention. According to the present invention, the combination of the DDD-type mutant of ND1 and the RRR-type mutant of ND1, or the combination of the DDD-type mutant of ND2 and the RRR-type mutant of ND1 showed particularly high specificity and nuclease activity (Example 8).

4. Kit

A further aspect of the present invention provides a kit for modifying a target nucleic acid, including the artificial nucleic acid-cleaving enzyme of the present invention, a nucleic acid encoding the artificial nucleic acid-cleaving enzyme, or a vector containing the nucleic acid, a transcription product of the nucleic acid, or a translation product thereof. Furthermore, the kit may include two or more kinds of artificial nucleic acid-cleaving enzymes as described above. In addition, the kit may include a nucleic acid encoding the two or more kinds of artificial nucleic acid-cleaving enzymes, or a vector containing the nucleic acid, a transcription product of the nucleic acid, or a translation product thereof. Preferably, the kit of the present invention includes one or two kinds of artificial nucleic acid-cleaving enzymes, a nucleic acid encoding the one or two kinds of artificial nucleic acid-cleaving enzymes, or a vector containing the nucleic acid, a transcription product of the nucleic acid, or a translation product thereof. The two or more kinds of artificial nucleic acid-cleaving enzymes may be, for example, an artificial nucleic acid-cleaving enzyme containing a DDD-type mutant of ND1 and an artificial nucleic acid-cleaving enzyme containing an RRR-type mutant of ND1. Further, the two or more kinds of artificial nucleic acid-cleaving enzymes may be, for example, an artificial nucleic acid-cleaving enzyme containing a DDD-type mutant of ND2 and an artificial nucleic acid-cleaving enzyme containing an RRR-type mutant of ND1. The kit may further include one or more additional reagents, and examples of the additional reagents include, but are not limited to, dilution buffers, reconstruction solutions, wash buffers, nucleic acid transfer reagents, protein transfer reagents, and control reagents. The kit usually comes with an instruction manual.

Unless otherwise stated, the meanings of the terms in the present specification are understood to be those commonly recognized in the fields of biology, molecular biology, biochemistry, genetics, and the like.

EXAMPLES

Hereinafter, the present invention is specifically described with reference to Examples, but the present invention is not limited to these Examples.

Note that the cells used in Examples were cultured as follows.

<Cell Culture>

HEK293T cells were maintained in D-MEM medium (Wako Pure Chemical Industries, Ltd.) containing 10% FBS (Difco), 1% streptomycin-penicillin (Wako Pure Chemical Industries, Ltd.), and 1% NEAA (Difco). CHO-K1 cells were maintained with Ham's-F12 (Difco) containing 10% FBS, 1% streptomycin-penicillin, and 5% kanamycin (Wako Pure Chemical Industries, Ltd.). Hereinafter, unless otherwise specified, the cultured cells were maintained at 37° C. and a carbon dioxide concentration of 5%, and if the temperature was specified, the temperature was followed. In addition, as for the culture solution, each of the above media was used unless otherwise specified.

Example 1

Search for Novel Nuclease Domains

Based on the amino acid sequence on the C-terminus side of FokI, a search for homologous natural materials was performed by protein-protein BLAST. In the obtained search results, four kinds of candidates were arbitrarily selected from those having a homology with FokI-ND of 35% to 70%. In descending order of high-homology sequence, they are referred to as ND1 (70% amino acid sequence identity; full-length amino acid sequence: SEQ ID NO: 1; corresponding base sequence: SEQ ID NO: 2), ND2 (57% amino acid sequence identity; full-length amino acid sequence: SEQ ID NO: 3; corresponding base sequence: SEQ ID NO: 4), ND3 (49% amino acid sequence identity; full-length amino acid sequence: SEQ ID NO: 5; corresponding base sequence: SEQ ID NO: 6), and ND4 (45% amino acid sequence identity; full-length amino acid sequence: SEQ ID NO: 7; corresponding base sequence: SEQ ID NO: 8).

When the amino acid sequences of ND1 to ND4 were compared with the amino acid sequence of FokI-ND, it was revealed that the lengths of FokI-ND and nuclease domain were almost the same, although there were amino acid deletions and substitutions. In addition, ND1 to ND4 carried amino acids (D483, R487) thought to be essential for FokI-ND to form a cleavage-active dimer, and amino acids (D450, D467, and K469) presumed to be involved in the hydrolysis-induced cleavage of phosphodiester bonds in DNA (FIG. 1B). Therefore, ND1 to ND4 were considered to have nuclease activity.

Example 2

Cleavage Activity of Novel Nuclease Domains (SSA Method)

In order to evaluate the nuclease activity of ND1 to ND4, a ZFN plasmid (pSTL-ZFA36-ND) containing each of ND1 to ND4 was prepared, and the cleavage activity of each novel nuclease domain was measured by SSA reporter assay.

(1) Construction of ZFN Plasmid

The base sequences of ND1 to ND4 were codon-optimized and artificially synthesized by IDT. The ZFN plasmid used (pSTL-ZFA36) was a construct prepared by Ochiai et al (Ochiai et al. (2010) Targeted mutagenesis in the sea urchin embryo using zinc-finger nucleases. Genes to Cells 15: 875-885). In order to replace FokI-ND of pSTL-ZFA36 with the newly identified ND1 to ND4, PCR was performed by PrimeSTAR Max (Takara) with each nuclease domain replacement primer pair. PCR was performed at 98° C. for 2 minutes, followed by 40 cycles of 98° C. for 10 seconds, 60° C. for 5 seconds, and 68° C. for 40 seconds. The obtained PCR product and artificially synthesized ND1 to ND4 were reacted using In-Fusion (Clontech) and transformed into *Escherichia coli*. A plasmid was extracted from the obtained transformant and the base sequence was confirmed to obtain each desired pSTL-ZFA36-ND plasmid. FIG. 1A shows a schematic diagram of the obtained ZFA (zinc finger array) 36-ND. The ZFA36-ND has a TGAAARA linker.

(2) SSA Reporter Assay

A 7.2 μL plasmid solution was prepared containing 120 ng of the SSA reporter plasmid, 240 ng of each of the above pSTL-ZFA36-ND plasmids, and 24 ng of the reference plasmid pRL-CMV (Promega) (a plasmid for standardizing transduction efficiency). The SSA reporter plasmid was prepared according to a known method so that the target sequence of the ZF array (ZFA36) containing the 6bp spacer sequence was inserted so as to be sandwiched between the overlapping regions of the Luc sequence (Ochiai et al. (2010) Targeted mutagenesis in the sea urchin embryo using zinc-finger nucleases. Genes to Cells 15: 875-885). To a 96-well multiwell plate (Iwaki) treated with polylysine coat, 25 μL of serum-free D-MEM culture solution was added, and 6 μL of plasmid solution was mixed. To this, 25.7 μL of a solution containing 0.7 μL of Lipofectamine LTX (Life Technologies) per 25 μL of serum-free D-MEM culture solution was added, and the mixture was allowed to stand at room temperature for 30 minutes. During this period, HEK293T cells were dissociated from a 100 mm tissue culture dish (Iwaki) by trypsin treatment, centrifuged at 1000 rpm for 3 minutes, the supernatant was removed, and the cells were suspended again in 5 mL of the culture solution. A 10 μL cell suspension was dispensed, and the number of cells was counted. From the obtained number of cells, a culture solution was added and adjusted so that the number of cells in the cell suspension was $6\times10^3$ cells/mL. To the above 96-well plate allowed to stand at room temperature for 30 minutes, 100 μL of the cell suspension was added. Then, the 96-well plate was transferred to 37° C. and a carbon dioxide concentration of 5%, and cultured to carry out transduction.

As to the culture solution of HEK293T cells cultured for 24 hours after transduction, 75 μL thereof was removed, 75 μL of Dual Glo luciferase substrate attached to Dual Glo Luciferase Assay System (Promega) was added to each well, and the cells were treated in the dark at room temperature for 10 minutes. Then, the luciferase activity was measured by TriStar LB941 of a multi-well plate reader. After the measurement, 75 μL of Dual Glo Stop & Glo Buffer containing 100-fold diluted Dual Glo Stop & Glo Substrate was added to each sample, and the mixture was treated in the dark at room temperature for 10 minutes, and the luciferase activity of the reference plasmid was measured with a plate reader in the same manner as before. As a control, ZFA36-FokI containing FokI-ND was used for the same measurement. As for the measurement results, the change in the value obtained by dividing the luciferase activity of the SSA reporter by the luciferase activity of the reference plasmid was calculated, and the relative value in each sample when the value of ZFA36-FokI was set to 1 was obtained.

(3) Results

Figure 1C:
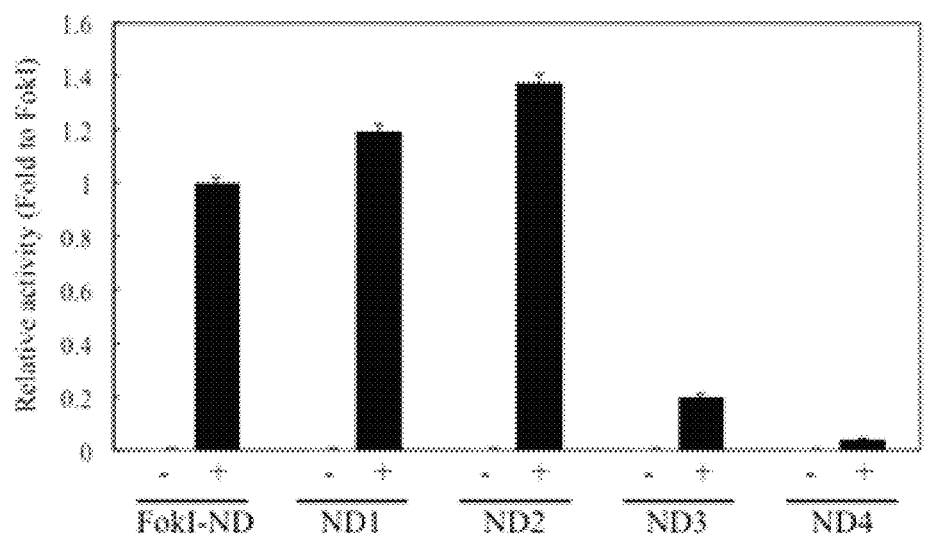
FIG. 1C shows the results of cell activity by the HEK293T cell-based SSA assay performed in Example 2. The data are shown as mean±SEM (n=3), where + and − indicate the presence or absence of the zinc finger target sequence reporter plasmid.

FIG. 1C shows the results. As is clear from FIG. 1C, ND1 and ND2 were higher by 20% or more in cleavage activity than the conventionally used FokI-ND. On the other hand, it was revealed that ND3 and ND4 have low cleavage activity and have only about 20% of FokI-ND.

Furthermore, it was confirmed, when the nuclease domain was not expressed intracellularly, whether the nuclease originally present in the cell targeted the luciferase reporter. As a result, it was found that the luciferase reporter could not be the target of various nucleases present in HEK293T cells because the relative activity against FokI-ND was extremely low. This analysis has revealed that ND1 and ND2 are novel nuclease domains derived from natural materials that surpass the cleavage activity of FokI-ND conventionally used in ZFNs.

Example 3

Cleavage Activity of Novel Nuclease Domains against Target Genome (Cel-I Method)

To confirm the extent to which the novel nuclease domains ND1 and ND2 confirmed to have nuclease activity in Example 2 bring about mutagenesis in genomic DNA in vivo, Cel-I assay was used to analyze the rate of mutagenesis into genomic DNA in cultured cells of the novel nuclease domains. As a control, FokI-ND, ND3, and ND4 were analyzed in the same manner.

(1) Cel-I Assay

In cells transduced with genome editing tools such as TALEN and ZFN, the target DNA is cleaved by their nuclease domain and the cleavage site is repaired by the repair mechanism existing in the cell, but a repair error occurs in this process. When the region containing the target sequence of this genomic DNA is amplified by PCR, a mixture product of a PCR fragment of the wild-type allele and a PCR fragment containing the mutation is obtained. Reassociation of these products after dissociation yields a mismatched double-stranded DNA composed of a PCR fragment of the wild-type allele and the allele containing the mutation, which is cleaved with a mismatch-specific endonuclease (Cel-I nuclease). Mutagenesis can be evaluated by detecting the cleavage pattern.

CHO-K1 cells were dissociated by trypsin treatment, centrifuged at 1000 rpm for 3 minutes, the supernatant was removed, and the cells were suspended in 10 mL of the culture solution. The number of cells was measured using a 10 μL cell suspension, a culture solution was added so that the number of cells was $1\times10^5$ cells/mL, and the cells were cultured overnight at 37° C. and a carbon dioxide concentration of 5%.

Each ZFN plasmid prepared in Example 2 was added to 500 μL of Opti-MEM (Difco) so as to have a weight of 800 ng, and the mixture was allowed to stand at room temperature for 5 minutes. To 500 μL of Opti-MEM, 32 μL of Lipofectamine LTX was added, and the whole amount was mixed with Opti-MEM medium containing the above plasmid, and allowed to stand at room temperature for 30 minutes. During this period, the culture solution of CHO-K1 cells grown overnight was replaced with 4 mL of Opti-MEM. To the cell culture solution, the whole amount of the plasmid solution allowed to stand at room temperature for 30 minutes was added, and the cells were cultured overnight at 37° C. and a carbon dioxide concentration of 5%. In the morning of the next day, the culture solution was changed from Opti-MEM to 10 mL of the culture solution, and the culture was further continued at 37° C. and a carbon dioxide concentration of 5%. In addition, puromycin (Wako Pure Chemical Industries, Ltd.) was added so that the final concentration was 500 μg/mL after 24 hours. After that, the culture was carried out every day for 3 days while exchanging culture solutions and adding puromycin.

CHO-K1 cells transduced with the ZFN plasmid as described above were harvested from the culture dish by trypsin treatment. The harvested cells were washed once with PBS (−). The obtained cells were subjected to the treatment by a cell lysis buffer and a protein degrader contained in either a DNA purification kit (Qiagen) or GeneArt Genomic Cleavage Detection Kit (Life Technologies) to prepare genomic DNA. With the prepared genomic DNA as a template, PCR was performed using KOD Fx Neo (ToYoBo) or AmpliTaq Gold (Life Technologies). In the case of KOD Fx Neo, PCR was performed at 95° C. for 2 minutes, followed by 40 cycles of 95° C. for 30 seconds, 60° C. for 30 seconds, and 68° C. for 30 seconds to amplify the target. In the case of AmpliTaq Gold, treatment was performed at 95° C. for 10 minutes, followed by 40 cycles of 95° C. for 10 seconds, 60° C. for 30 seconds, and 72° C. for 40 seconds, and finally treatment at 72° C. for 7 minutes was performed to amplify the target. Equivalent amounts of each obtained PCR product were subjected to a cleavage reaction with a detection enzyme using GeneArt Genomic Cleavage Detection Kit according to the manual. In the solution after the reaction, cleaved fragments were detected by agarose gel electrophoresis or MultiNA (Shimadzu Corporation). Cleavage efficiency was calculated from the molar concentrations of the uncleaved bands and the larger cleaved fragments.

(2) Results

FIG. 2 shows the results of electrophoresis by MultiNA. Table 1 shows the candidate sequences for the ZFN genomic target (ZFA36-ZFA36) in CHO-K1 cells used in the analysis. Table 1 also shows the candidate sequences for the ZFN genomic target (ZFL1-ZFA36) used in Example 7 described later.

TABLE 1

Sequences of Target Sites

| Target Site | | Target Site Sequence |
|---|---|---|
| ZFA36-ZFA36 | | ACCATCTTCnnnnnnGAAGATGGT |
| | 1st site | ACCATCTTCcactctGAAGATGGA |
| | 2nd site | ACCATCTTCaagagaGAAGATGGC |
| | 3rd site | ACCATCTTCcttgatGAAGATGCC |
| ZFL1-ZFA36 | | GTCACCTTCnnnnnnGAAGATGGT |
| | 1st site | GTCACCTTCaagtctGAAGATGGT |
| | 2nd site | TTCACCTTCttaagtGAAGATGGT |

Figure 2A:
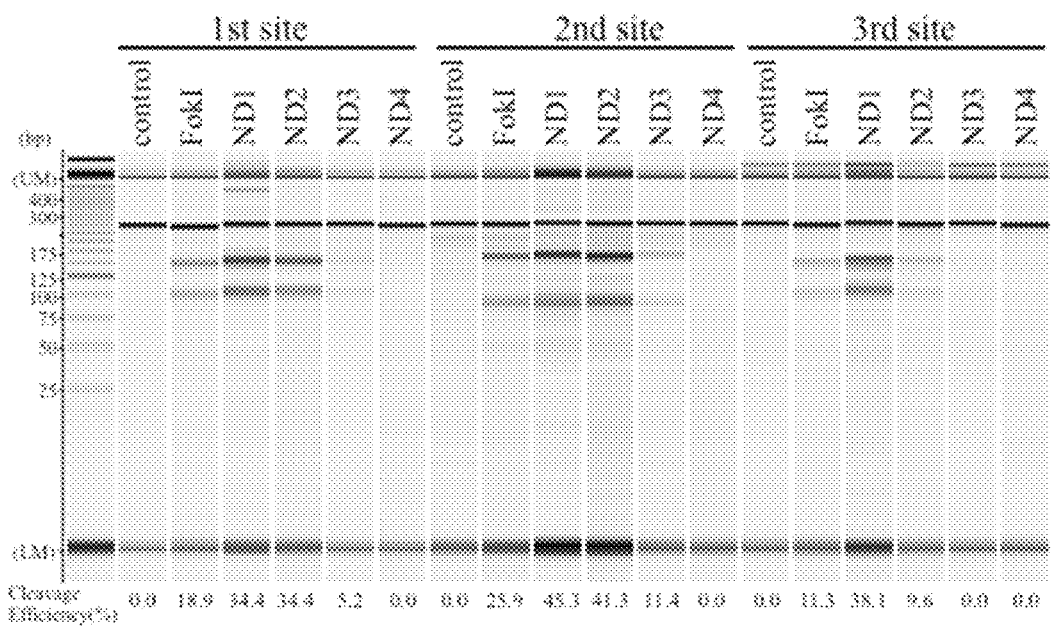
FIG. 2A shows the cleavage activity of a nuclease domain against a target genome. CHO-K1 cells transfected with ZFA36-ND were incubated at 37° C. and harvested after 72 hours to prepare a genomic DNA template. The PCR product containing the ZFA36 target site was cleaved by GeneArt Genomic Cleavage Detection Kit. Cleaved fragments were analyzed by electrophoresis (MultiNA System). The cleavage efficiency was calculated from the molar concentrations of uncut bands and larger cleaved fragments. In the figure, "FokI" means FokI-ND.
Figure 2B:
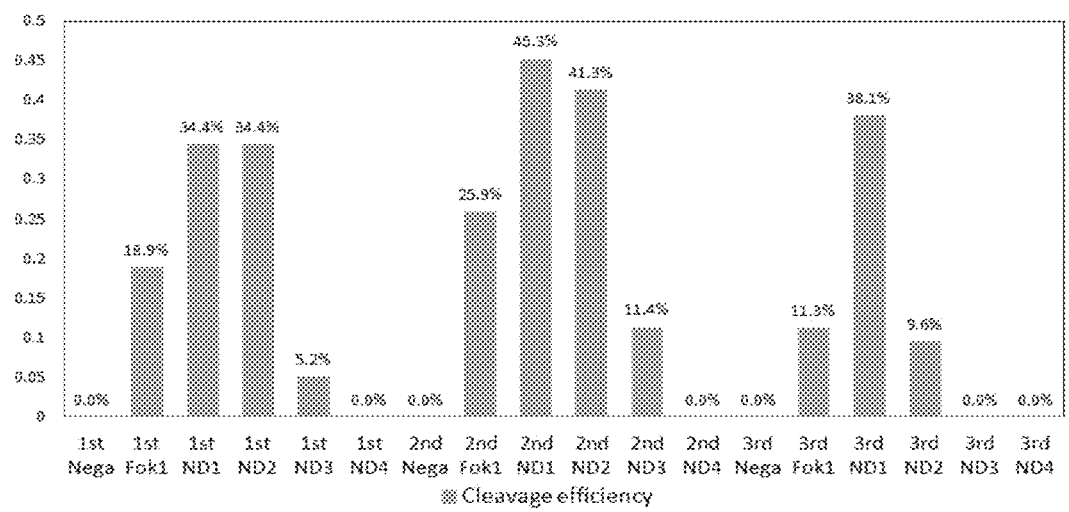
FIG. 2B shows the results of the cleavage activity test for the target genome of the nuclease domain performed in Example 3 in terms of cleavage efficiency.

In all the target sequences analyzed, the target half site (L) was in perfect agreement with the target sequence of the ZF array. On the other hand, the target half site (R) did not completely match the target sequence of the ZF array, and there was a mismatch on the 3′-side. Cleavage of these target candidate sequences by Cel-I revealed that the cleavage efficiency of the novel nuclease domains ND1 and ND2 was about 1.5 times higher than that of FokI-ND, similar to the results of luciferase reporter analysis (FIGS. 2A and 2B). In particular, the mutagenesis activity of ND1 had more stable and higher cleavage activity than that of ND2 in all the target candidate sequences analyzed. These results have revealed that ND1 and ND2 are novel nuclease domains derived from natural materials that are more active than conventional FokI-ND also with respect to target genomic sequences in vivo, similar to the results of the reporter analysis using the luminescence of luciferase in Example 2.

On the other hand, in ND3, although the mutagenesis activity changed depending on the target candidate sequence, it was about 25 to 45% of the activity of FokI-ND. In addition, in ND4, no mutagenesis into the detectable target candidate sequences was observed in all the analyzed target candidate sequences.

Example 4

Analysis of Intracellular Accumulation Amount of Novel Nuclease Domains

To clarify whether or not the reason why the mutagenesis rate of the novel nuclease domain is higher than that of FokI-ND is that the apparent mutagenesis rate is higher because the intracellular accumulation amount is larger than that of FokI-ND, the amount of each nuclease domain accumulated was analyzed by adding a tag to ZFN and using an antibody that recognizes it. In order to perform this analysis, a construct in which an AcV5 tag was newly added to the N-terminus of ZFN was prepared and used for the analysis.

(1) Analysis of Intracellular Accumulation Amount (Western Blot Analysis)

In order to analyze the amount of ZFN accumulated in cells, PCR was performed using each pSTL-ZFA36-ND prepared in Example 2 as a template, and after an In-Fusion reaction, transformation into *Escherichia coli* was performed to obtain each ZFN plasmid having an AcV5 tag added to the N-terminus side of the ZF array. A plasmid solution in an amount of 7.2 μL containing 240 ng of the ZFN plasmid was prepared. The plasmid solution was transduced into HEK293T cells in the same manner as in the SSA assay described in Example 2, and cultured at 37° C. and a carbon dioxide concentration of 5% for 3 days. The culture solution was changed every day.

The cultured HEK293T cells were treated with trypsin and centrifuged, and the supernatant was removed. The obtained precipitate was suspended in PBS, and added with a sample treatment solution composed of 2% SDS, 10% glycerol, 10 mM DTT, 0.005% BPB, and 62.5 mM Tris-HCl (pH 6.8), and the mixture was boiled at 95° C. for 5 minutes. Then, nucleic acids and the like were cut by ultrasonic treatment. The obtained protein samples were quantified using a protein assay kit (Bio-Rad) using BSA as an external standard. Each sample prepared to be 10 μg was separated by SDS-PAGE and transferred to a PVDF membrane by semi-dry transfer. Post-transcriptional PVDF membranes were blocked with PBS containing 5% skim milk and incubated with 2000-fold diluted α-tubulin antibody (Abcam) and AcV5-tag antibody (Sigma). After washing with PBST, they were incubated with 2000-fold diluted goat anti-mouse IgG antibody-conjugated HRP (Bio-Rad). After washing with PBST, they were made to emit light using Supersignal West Dura Extended Duration Substrate (Thermo Fisher) and exposed to an X-ray film.

(2) Results

Figure 3:
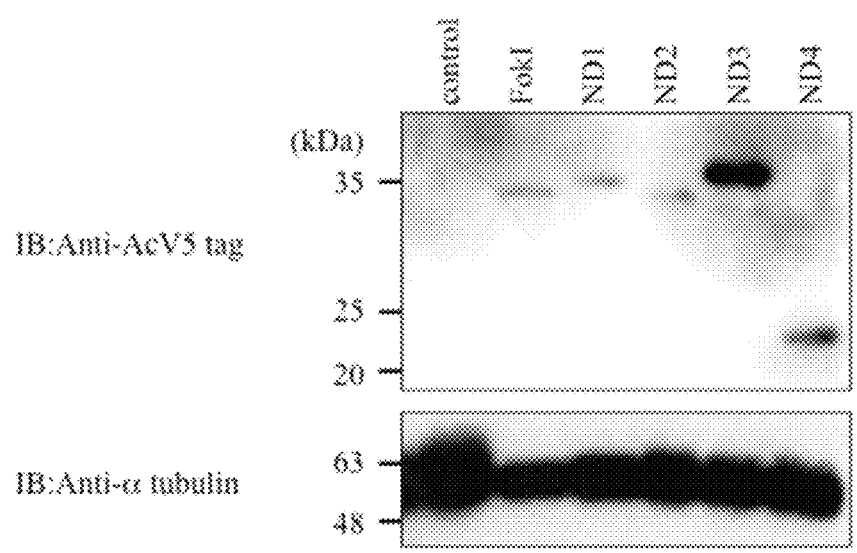
FIG. 3 shows the results of Western blot analysis showing the expression level of ZFA36-ND. AcV5 tag-ZFA36-ND was expressed by HEK293T cells. Transfected cells were harvested after 72 hours, and cell lysates were probed with antibodies against both AcV5 tag and α-tubulin. In the figure, "FokI" means FokI-ND.

FIG. 3 shows the results. When the amount of protein in the cell disruption solution was compared using a monoclonal antibody against α-tubulin as an internal standard, the amount of tubulin accumulated was large in the control cells that had not been transduced with ZFN. When ZFN containing each nuclease domain was expressed, FokI-ND and ND1 appeared to be slightly less, but showed approximately equal amounts of tubulin accumulation, and approximately equal amounts of protein separation by SDS-PAGE and transcription to PVDF membranes.

On the other hand, as can be seen from the accumulated amount of tubulin, in the control, although the analysis was performed with a larger amount of protein than the cell disruption solution expressing each nuclease domain, no non-specific signals derived from the AcV5 tag antibody were observed, and it was found that the AcV5 antibody specifically recognized the tag. When the amount of protein accumulated was analyzed using this AcV5 antibody, in the cell disruption solution transduced with each nuclease domain, a signal derived from the AcV5 tag was obtained in FokI-ND and ND1 to ND3 at around 35 kDa, which is the expected size. In addition, the signals of FokI-ND, ND1, and ND2 were almost the same. When considered in combination with the amount of tubulin used as an internal standard, the intracellular accumulation amount of each nuclease domain of FokI-ND, ND1, and ND2 suggested that FokI-ND accumulated the most in the cell, followed by ND1 and ND2 in this order. On the other hand, for ND3, since the signal derived from the AcV5 tag was obtained significantly stronger than that of FokI-ND and the like, it was revealed that the amount of ND3 accumulated in the cells was larger than that of FokI-ND and the like.

(3) Analysis of Intracellular Accumulation Amount and Localization (ZFN-EGFP Expression Analysis)

Moreover, although the cleavage activity was lost, a construct in which EGFP was fused to the C-terminus was prepared in order to clarify the intracellular accumulation amount and localization of each ZFN. The prepared construct was used to perform transduction into HEK293T cells, and fluorescence derived from GFP was observed with a confocal laser scanning microscope to analyze the expression level of ZFN and to, at the same time, stain the nuclei with DAPI for clarification of intracellular localization.

PCR was performed using each pSTL-ZFA36-ND prepared in Example 2 as a template, and after an In-Fusion reaction, transformation into *Escherichia coli* was performed to obtain each ZFN plasmid having EGFP added to the C-terminus side of the ZF array. A plasmid solution in an amount of 7.2 µL containing 240 ng of the ZFN plasmid was prepared. The plasmid solution was transduced into HEK293T cells in the same manner as in the SSA assay described in Example 2, and cultured at 37° C. and a carbon dioxide concentration of 5% for 3 days. HEK293T cells were applied to a collagen-treated 24-well glass bottom plate.

The grown HEK293T cells were fixed with paraformaldehyde. After washing with PBS (−), nucleic acid was stained with DAPI. After washing with PBS (−) again, observation was performed with a confocal laser scanning microscope (FD-1000D, Olympus). Fluorescence images were obtained at Ex: 473 nm/Em: 510 nm for EGFP and at Ex: 405 nm/Em: 473 nm for DAPI.

(4) Results

Figure 4:
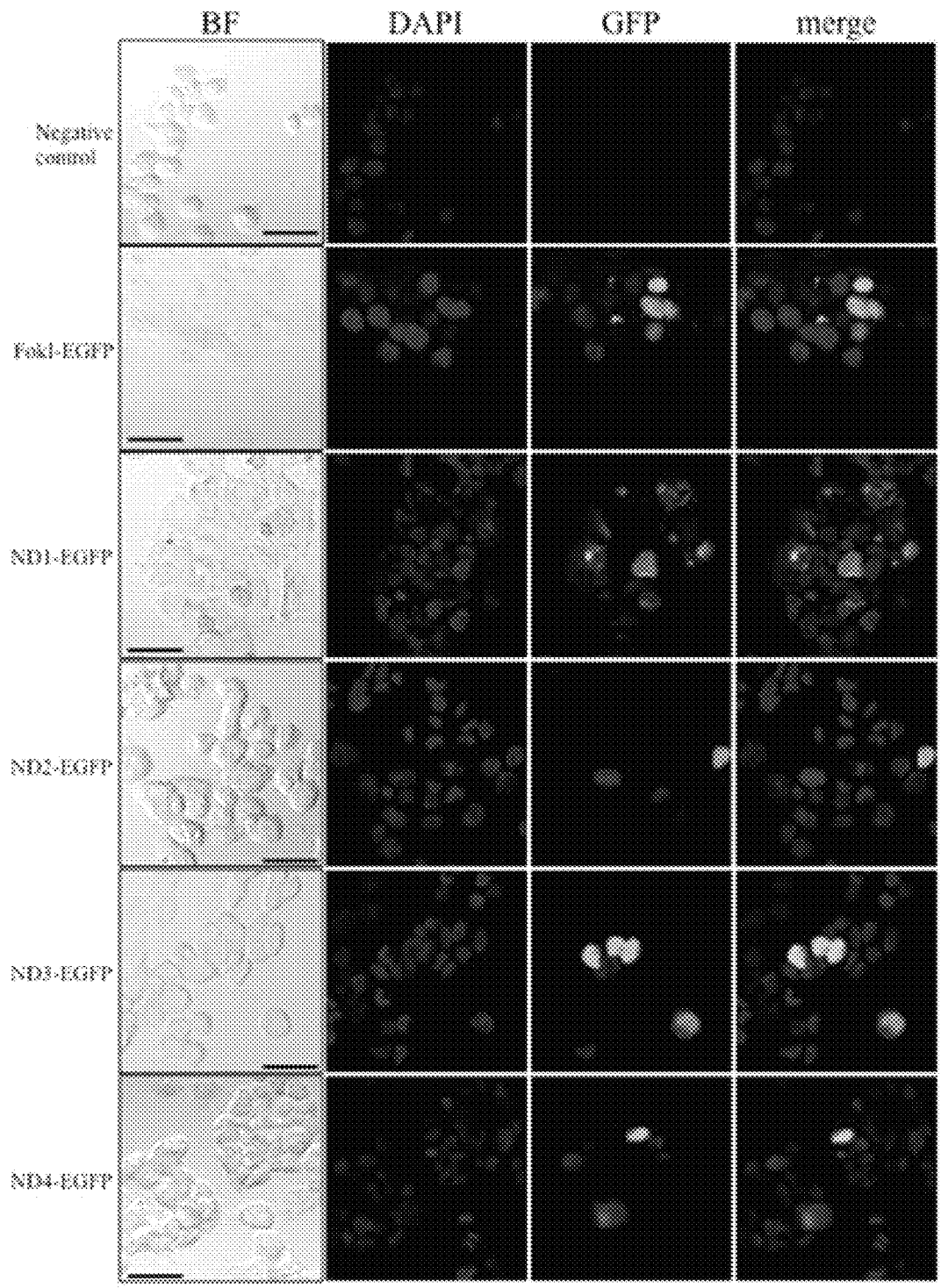
FIG. 4 shows LSM images of ZFA36-ND-EGFP in HEK293T cells, and a photomicrograph of ZFA36-ND-EGFP overexpressing cells. DNA was visualized by DAPI staining. Scale bar: 40 μm. In the figure, "FokI" means FokI-ND.

FIG. 4 shows the results. In the negative control in which ZFN was not expressed, fluorescence derived from GFP was not observed, and only fluorescence derived from nucleic acid by DAPI was observed. In cells introduced with ZFN having EGFP fused in each nuclease domain, GFP-derived fluorescence was observed in the cytoplasm and nucleus, although there was a difference in GFP-derived fluorescence intensity.

When FokI-ND-EGFP was expressed, GFP fluorescence was observed in the cytoplasm for some cells and also in the nucleus for some other cells. When ND1-EGFP was expressed, GFP-derived fluorescence was observed in more cells than in FokI-ND, but the intensity of each fluorescence was weaker than in FokI-ND. When ND2-EGFP was expressed, it was found that in the observed cells, the number of cells having GFP-derived fluorescence was smaller than that in FokI-ND, but it was localized in the cytoplasm and nucleus. When ND3-EGFP was expressed, GFP-derived fluorescence was observed in the nucleus and cytoplasm, as in FokI-ND and the like. In addition, since GFP-derived fluorescence was more strongly observed in ND3 than in other nuclease domains, it was considered that the expression level was higher in the cells. Analysis of ND3 by Western blotting also showed that the intracellular accumulation amount was higher than that of FokI-ND, but even though it could be localized in the nucleus, the apparent mutagenesis rate was low, and it was considered that the biochemical properties of the enzyme were also different, such as a different optimum temperature from that of FokI-ND.

(5) Summary

From the results of antibody analysis and GFP fluorescence analysis, it was revealed that FokI-ND, ND1, and ND2 were accumulated in cells to the same extent. This has revealed that the high cleavage activity of the novel nuclease domains ND1 and ND2 is not because of the large amount of intracellular accumulation, but because of the higher cleavage activity than that of FokI-ND, meaning that ND1 and ND2 are nuclease domains derived from natural materials having cleaving activity that surpasses FokI-ND, which has been conventionally used in ZFNs and the like.

Example 5

Analysis of Target Sequence Selectivity of Novel Nuclease Domains

To further verify the usefulness of ND1 and ND2, an attempt was made to modify the linker sequence between the ZF array and the nuclease domain. In conventional ZFNs, it has been reported that when the linker sequence is modified, the length of the spacer sequence exhibiting cleavage activity and the toxicity given to cells are different. Therefore, in addition to the TGAAARA linker, which is a conventional linker sequence used in the analysis so far, ZFN vectors modified into GS linker, RPGEKP linker, and TGPGAAARA linker were constructed and used for the analysis.

(1) Experimental Method

As a ZFN vector having a TGAAARA linker, each pSTL-ZFA36-ND prepared in Example 2 was used. The selection of GS linker, RPGEKP linker, and TGPGAAARA linker was based on the reports of Handel et al. (2009) (NPL 1), Wilson et al. (2013) (Wilson et al. (2013) Expanding the Repertoire of Target Sites for Zinc Nuclease-mediated Genome modification. Mol. Ther-Nucleic Acids 2: e88), and Nomura et al. (2012) (Nomura et al. (2012) Effects of DNA Binding of the Zinc Finger and Linkers for Domain Fusion on the Catalytic Activity of Sequence-Specific Chimeric Recombinase Determined by a Facile Fluorescent System. Biochemistry. 51: 1510-1517). The ZFN vector with each linker modified was subjected to PCR by PrimeSTAR Max (Takara) with each linker modification primer pair using pSTL-ZFA36-ND as a template. The obtained PCR product was reacted using In-Fusion (Clontech) and transformed into *Escherichia coli*. A plasmid was extracted from the obtained transformant, and the base sequence was confirmed to obtain the desired plasmid. In addition, SSA reporter plasmids with spacer lengths modified to 5 bp or 7 bp were used to perform SSA reporter assays as described in Example 2 to measure the nuclease activity of each ZFN.

(2) Results

Figure 5A:
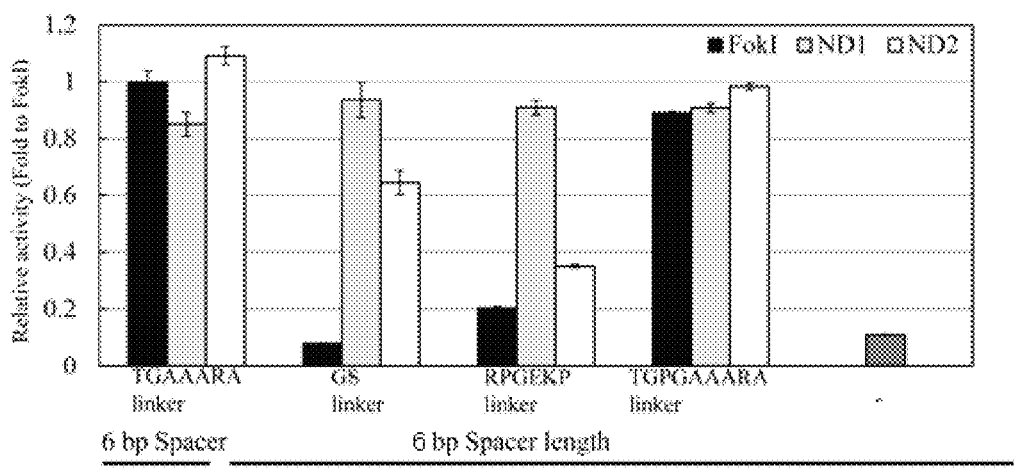
FIGS. 5A-5B show reporter activity profiles of ZFA36-ND linker mutants at different spacer lengths, and shows the results of the SSA reporter assay performed in Example 5. ZFN linker mutants and spacer lengths are shown as 6 bp FIG. 5A, 5 bp FIG. 5B, and 7 bp FIG. 5C. The data are normalized to the luciferase activity of FokI's TGAAARA-linker with a 6 bp spacer length. The data are shown as mean±SEM (n=3). In the figure, "FokI" means FokI-ND.
Figure 5B:
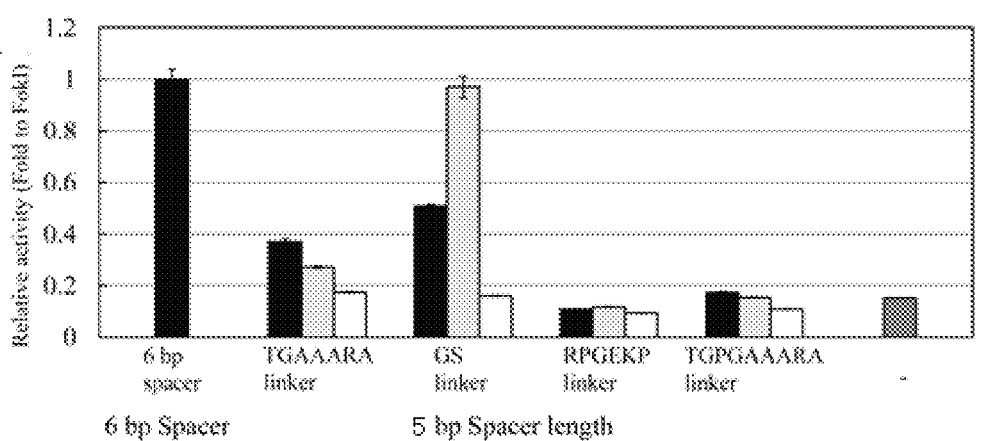
Figure 5C:
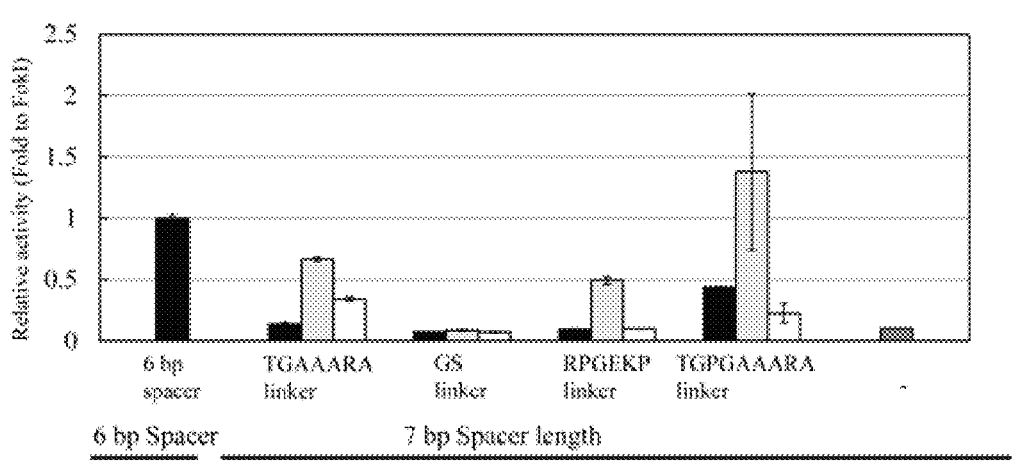

FIGS. 5A-5B show the results. Note that the cleavage activity includes the conventional linker and is shown by the relative activity when the cleavage activity of ZFA-FokI-ND of the spacer sequence 6bp is 100%.

When the length of the spacer sequence was 6 bp, in FokI-ND, the activity was reduced to 20% or less when modified to a GS linker or RPGEKP linker, as compared with the cleavage activity when the ZF array and the nuclease domain were connected by the conventional linker (TGAAARA). On the other hand, when modified to a TGPGAAARA linker, the cleavage activity of FokI-ND was about 90% of that before the linker modification (FIG. 5A).

In ND1, when the spacer sequence was 6 bp, the cleavage activity was not affected even when the linker sequence was modified, and the cleavage activity was about 90% of that of FokI-ND before the linker sequence modification. In ND2, when the spacer sequence was 6 bp, the cleavage activity was reduced to about 60% when modified to the GS linker sequence and to about 35% when modified to the RPGEKP linker sequence, as compared with the cleavage activity of FokI-ND before the linker sequence modification. From these results, it has been clarified that, as previously reported, even when the spacer sequences have the same length, the linker sequence used in the analysis affects the cleavage activity of the nuclease domain.

When the length of the spacer sequence was set to 5 bp, the cleavage activity of FokI-ND was reduced to about 40% in the conventional linker sequence (TGAAARA linker) as compared with the case of 6 bp, but when modified to a GS linker, about 50% of cleavage activity remained. However, when modified to RPGEKP linker or TGPGAAARA linker, the cleavage activity of FokI-ND was about 20% of that of the conventional linker sequence, and almost no cleavage was possible. It was revealed that in ND1, when the spacer sequence was 5 bp, the cleavage activity remained high when modified to the GS linker, but the conventional linker sequence reduced the cleavage activity to about 30%, and when converted to other linker sequences, almost no cleavage was possible.

In ND2, when the length of the spacer sequence was set to 5 bp, almost no cleavage activity was exhibited even when the linker sequence was modified. When the length of the spacer sequence was short, the influence of the linker sequence was large, and it was considered that the shorter the linker sequence, the easier it was to maintain the cleavage activity.

When the length of the spacer sequence was set to 7 bp, in FokI-ND, cleavage activity was observed only when modified to the TGPGAAARA linker, and this activity was about 50% of the cleavage activity of the conventional linker sequence having a spacer sequence length of 6 bp. Almost no cleavage activity was exhibited when converted to other linker sequences.

In ND1, it was found that when the length of the spacer sequence was set to 7 bp, the cleavage activity was not exhibited when modified to the GS linker sequence, but when modified to other linker sequences, the cleavage activity of about 50% or more was exhibited. In particular, the TGPGAAATA linker was considered to be higher than the cleavage activity of the target FokI-ND. On the other hand, for ND2, the conventional linker sequence showed about 40% cleavage activity, but when modified to other linker sequences, almost no cleavage activity was exhibited. When the length of the spacer sequence was long, the longer the linker sequence, the higher the cleavage activity tended to be.

From the above results, it has been clarified that ND1 is less susceptible to the modification of the linker sequence than FokI-ND, has less restriction on the spacer sequence, and exhibits higher cleavage activity than FokI-ND. This indicates that ND1 is a nuclease domain that is more versatile than FokI-ND also in terms of target sequence selectivity and the like.

So far, there have been reports on the modification of FokI-ND for ZFN. It has also been reported that the nuclease domain itself is modified from FokI-ND to endonucleases such as PvuII and I-TevI. Although the modified ZFN using this I-TevI has a higher cleavage activity than FokI-ND, the spacer sequence is about 30 bp, which is longer than that of FokI because of the intramolecular linker and DNA binding motif existing in I-TevI, in addition to the ZF array. Similarly, when modified to PvuII, the spacer sequence is long. As a result, it is considered that the DNA sequence acting on the ZFN is also long and easily restricted by the base sequence. On the other hand, when used in ZFN, the nuclease domain of the present invention has the same protein structure as the conventional FokI-ND but has a high mutagenesis rate, and the target DNA sequence acting on the ZFN is shortened to 24 bp as a whole. From this, the nuclease domain of the present invention is less restricted by the base sequence than I-TevI and the like, and is easy to handle as a simpler genome editing tool.

Example 6

Cleavage Activity of Novel Nuclease Domain Introduced with Sharkey Mutation

An amino acid substitution (Sharkey mutation) is known that increases cleavage activity when introduced into FokI-ND (Guo, J., Gaj, T. and Barbas, C. F., 3rd. (2010) Directed evolution of an enhanced and highly efficient FokI cleavage domain for zinc finger nucleases. J Mol Biol, 400, 96-107). Therefore, introduction was attempted of the same amino acid substitutions as the Sharkey mutation in the novel nuclease domains ND1 and ND2 for the purpose of further enhancing the cleavage activity.

(1) Experimental Method

ZFN vectors containing nuclease domains introduced with the Sharkey mutations (S418P and K441E amino acid substitutions in FokI-ND, and corresponding amino acid substitutions in other nuclease domains) was subjected to PCR by PrimeSTAR Max (Takara) with a Sharkey mutagenesis primer pair using each pSTL-ZFA36-ND as a template with reference to the report by Guo et al. The obtained PCR product was reacted using In-Fusion (Clontech) and transformed into *Escherichia coli*. A plasmid was extracted from the obtained transformant, and the base sequence was confirmed to obtain the desired plasmid. An SSA reporter assay was performed as described in Example 2 to measure the nuclease activity of each ZFN. As a control having no Sharkey mutation, each pSTL-ZFA36-ND prepared in Example 2 was used.

(2) Results

Figure 6A:
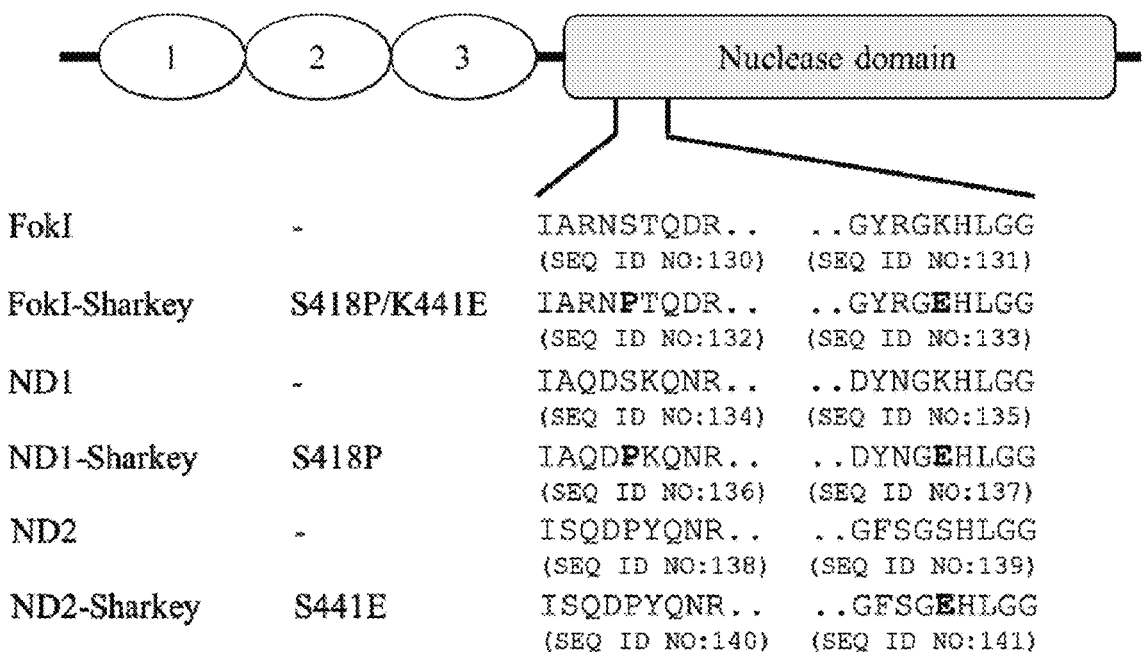
FIGS. 6A-6B show a reporter activity profile of the ZFA36-ND-Sharkey mutant. In the figure, "FokI" means FokI-ND. FIG. A Schematic diagram of ZFN. The sequences of ND1, ND2, and Sharkey mutants corresponding to the amino acid sequence at positions 414 to 445 of FokI-ND are shown. In the figure, the amino acid number is based on the full-length amino acid of each nuclease domain.
Figure 6B:
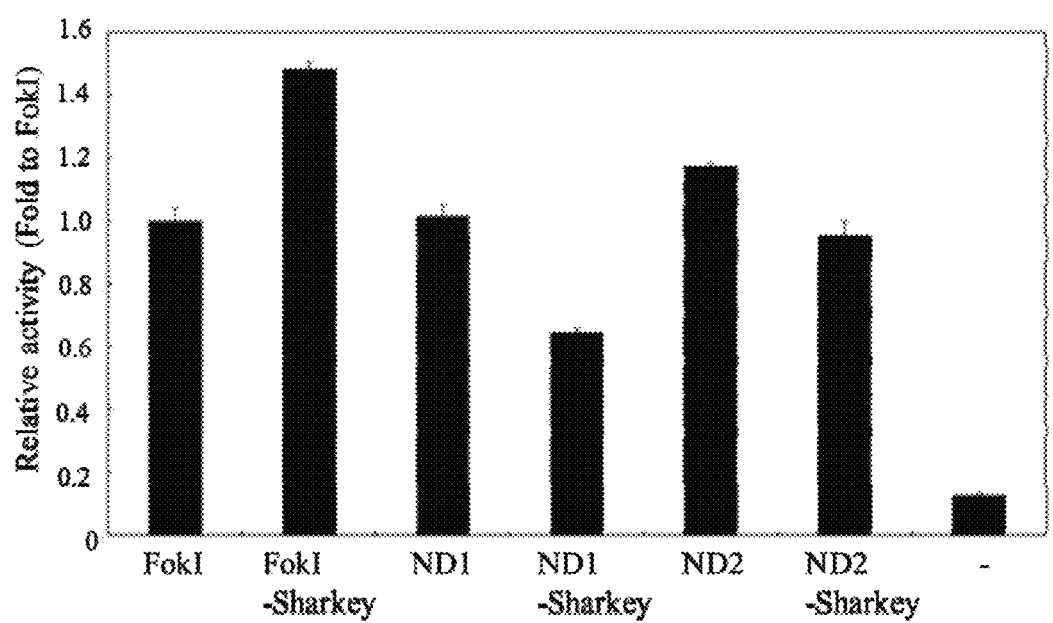

By comparing the amino acid sequences of FokI-ND, Sharkey mutation, and ND1 and ND2, the amino acid substitution site brought about by the Sharkey mutation was identified (FIGS. 6A-6B). FIGS. 6A-6B show the results. Note that each of the cleavage activities is shown as a relative activity when the cleavage activity of ZFA-FokI-ND having no Sharkey mutation is 1.

In ND1, the amino acids corresponding to the positions S418 and K441 of FokI-ND, which are the amino acid sites required for the introduction of the Sharkey mutation, were the same as those of FokI-ND and were S424 and K447, respectively. On the other hand, in ND2, the amino acid corresponding to the position S418 of FokI-ND was the same as that of the Sharkey mutation (P422), but the amino acid corresponding to the position K441 of FokI-ND was S445. Therefore, ND1 and ND2, in which the same amino acid substitutions as the Sharkey mutation were introduced into the above amino acid sites, were designated as ND1-Sharkey and ND2-Sharkey, respectively. When the cleavage activity was measured using a luciferase reporter using these, the cleavage activity was increased by about 1.5 times in the Sharkey mutation of FokI-ND (FIG. 6B). As already reported, the Sharkey mutation has been shown to enhance the cleavage activity of FokI-ND. However, in both ND1-Sharkey and ND2-Sharkey, the cleavage activity was lower than that before the introduction of the amino acid substitutions, and the expected high cleavage activity was not obtained. This result means that the cleavage mechanism of the nucleases ND1 and ND2 is different from that of FokI-ND. Therefore, the novel nuclease domains ND1 and ND2 are different nuclease domains from FokI-ND.

Example 7

Cleavage Activity Using Heterodimer Type Nuclease Domains

When the target sequence is cleaved by a ZFN, FokI-ND forms a dimer. Furthermore, it is known that, by substituting a specific amino acid, FokI-ND can be functionally converted into a mutant such as DDD-type/RRR-type and the like which exhibit cleavage activity only at the time of heterodimer formation. Therefore, further analysis was performed in order to clarify whether the functional modifications for maintaining the cleavage activity would be possible in the novel nuclease domains ND1 and ND2.

By making an alignment with FokI-ND, it was verified whether the amino acids involved in heterodimer formation were also conserved in ND1 and ND2 (FIG. 1B). As a result, amino acids other than the histidine residue presenting most on the C-terminus side in the amino acid substitution site for the heterodimer type nuclease revealed by FokI-ND were also conserved in ND1 and ND2. From this, it was possible to infer that ND1 and ND2 could be functionally converted to the heterodimer type in the same manner as FokI-ND. Therefore, in ND1 and ND2, the cleavage activity during heterodimer formation was measured.

(1) Experimental Method

Substitutions were introduced at the relevant amino acid sites as shown in Table 2 in order to perform functional conversion to the heterodimer type for ND1 and ND2. Note that in the table, "FokI" means FokI-ND. In the table, the amino acid numbers are based on the full-length amino acids of each nuclease domain.

TABLE 2

Amino Acid Sequences of FokI Nuclease Domains and Homologs

| Nuclease | | Amino Acid Sequence of Nuclease Domain |
|---|---|---|
| FokI | — | GQADEMQRYVE.. TRNKH ..RLNHITN |
| FokI-DDD | R487D/N496D | GQADEMQDYVE.. TRDKH ..RLNHITN |
| FokI-RRR | D483R/H537R | GQAREMQRYVE.. TRNKH ..RLNRITN |
| ND1 | — | SQADEMQRYVD.. NRNAI ..RVSNLTK |
| ND1-DDD | R493D/N502D | SQADEMQDYVD.. NRDAI ..RVSNLTK |
| ND1-RRR | D489R/N543R | SQAREMQRYVD.. NRNAI ..RVSRLTK |
| ND2 | — | SQADEMERYRE.. DENEH ..RISIDTG |
| ND2-DDD | R487D/N496D | SQADEMEDYRE.. DEDEH ..RISIDTG |
| ND2-RRR | D483R/I537R | SQAREMERYRE.. DENEH ..RISRDTG |

In order to analyze the heterodimer formation, the target half-site L and the target half-site R, which are the target sequences of the ZF array, need to be different sequences. A construct was constructed using a ZF array whose target sequence was a sequence different from the ZF array used in the previous examples. As the ZF array, hPGRN_ZFL1 was artificially synthesized by IDT (hereinafter also referred to as "ZFL1"). In order to replace the ZF array of each pSTL-ZFA36-ND prepared in Example 2 with hPGRN ZFL1, each pSTL-ZFA36-ND was used as a template with a ZF array replacement primer pair, and PCR was performed by PrimeSTAR Max. The obtained PCR product and hPGRN ZFL1 were reacted using In-Fusion and transformed into *Escherichia coli*. A plasmid was extracted from the obtained transformant, and the base sequence was confirmed to obtain each desired pSTL-hPGRN ZFL1-ND plasmid.

Furthermore, in order to functionally convert the amino acids of the novel nuclease domains corresponding to the amino acids (D483, R487, and N496) involved in the heterodimerization of FokI-ND to the DDD-type, each pSTL-hPGRN_ZFL1-ND was used as a template and a primer pair was used to perform PCR by PrimeSTAR Max. Further, in order to convert the function to the RRR-type, each pSTL-ZFA36-ND was used as a template to perform PCR in the same manner. Each of the obtained PCR products was transformed into *Escherichia coli* after an In-Fusion reaction. Plasmids were extracted from the obtained transformants, and after sequence confirmation, target constructs (hereinafter also referred to as "DDD-type mutant ZFL1-ND" and "RRR-type mutant ZFA36-ND") were prepared. The DDD-type ZFL1-ND and RRR-type ZFA36-ND obtained were used to perform an SSA reporter assay as described in Example 2 to measure the nuclease activity of each ZFN. Note that the amount of each ZFN plasmid in 7.2 µL of the plasmid solution used in the SSA reporter assay was changed to 120 ng for the target half-site L and 120 ng for the target half-site R. In addition, nuclease activity was measured by the Cel-I assay in the same manner as described in Example 3.

(2) Results

Figure 7A:
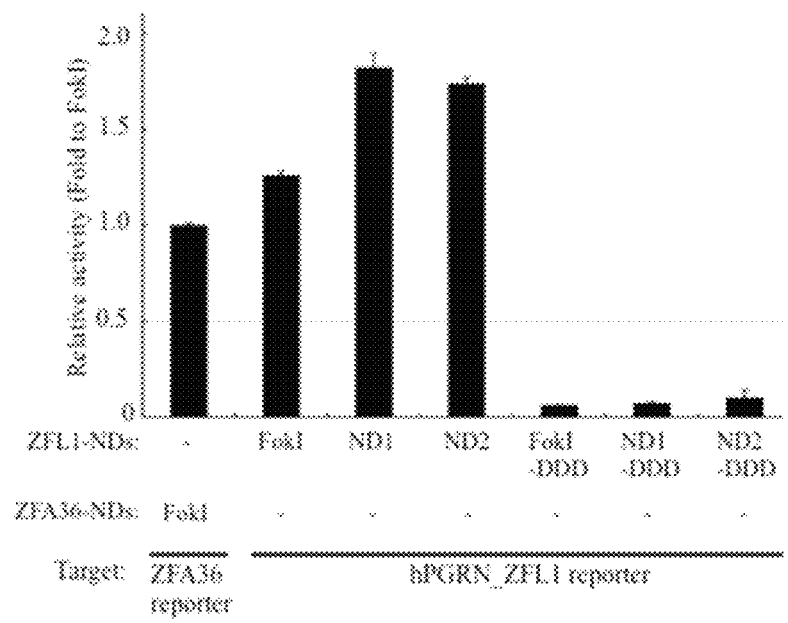
FIGS. 7A-7B show nuclease activity in single use of ZFNs with heterodimer type mutations measured by a cell-based SSA assay. HEK293T cells were co-transfected with each ZFN expression plasmid, reporter plasmid, and reference plasmid to perform a dual luciferase assay. After transfection, cells were incubated for 24 hours, lysed, and analyzed for luciferase activity.
Figure 7B:
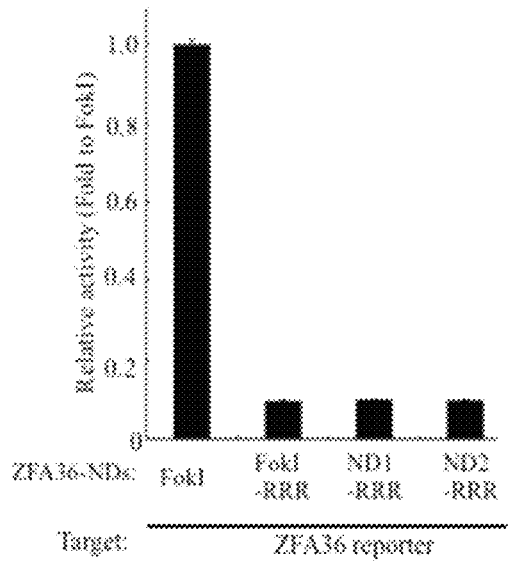
Figure 8A:
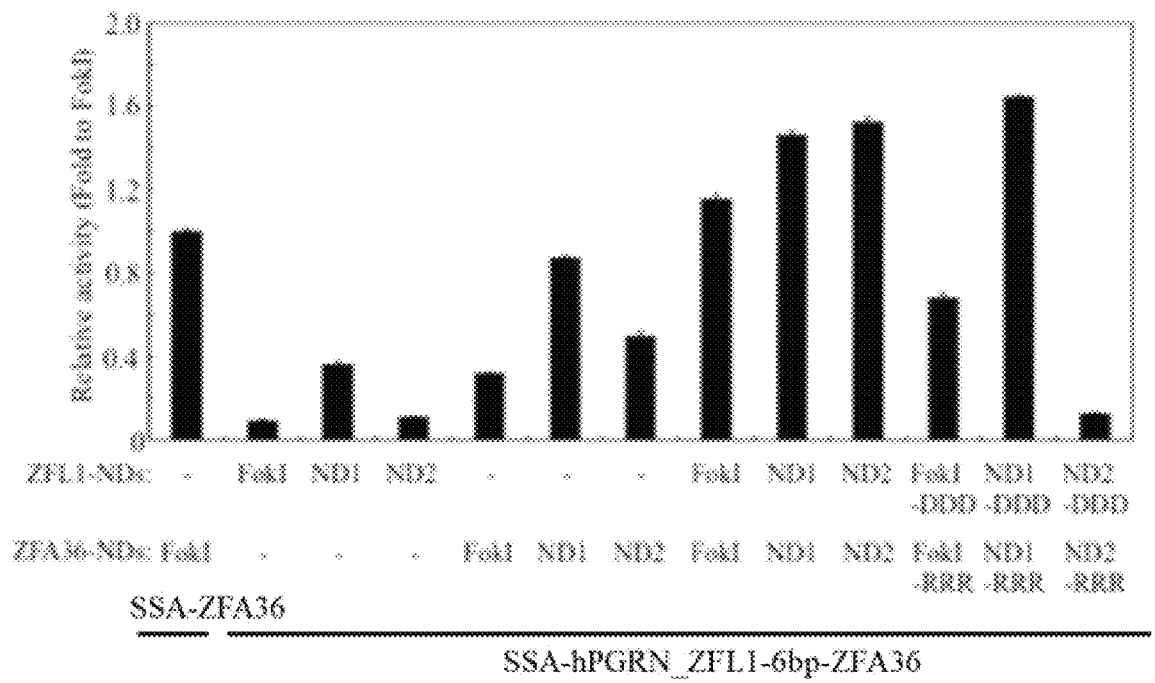
FIG. 8A analysis of homodimer and heterodimer cleavage reactions by SSA reporter assay. HEK293T cells were co-transfected with each pair of ZFN expression plasmids, reporter plasmids, and reference plasmids to perform a dual luciferase assay. After transfection, cells were incubated for 24 hours, lysed, and analyzed for luciferase activity. The data are shown as mean±SEM (n=3). In the figure, "FokI" means FokI-ND.
Figure 8B:
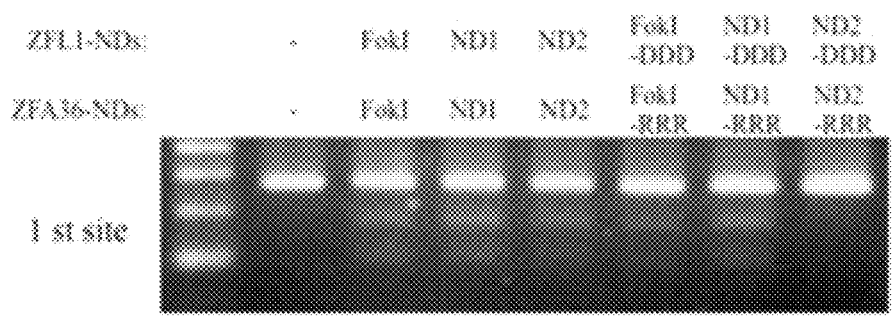
FIG. 8B shows analysis of homodimer and heterodimer cleavage reactions by the Cel-I assay. CHO-K1 cells transfected with each ZFN plasmid were incubated at 37° C. for 72 hours. Genomic DNA was then prepared from the transfected cells to amplify the fragments containing the ZFA36-ZFL1 target site. The PCR product was cleaved with GeneArt Genomic Cleavage Detection Kit. The cleaved fragments were analyzed by agarose gel electrophoresis. In the figure, "FokI" means FokI-ND.

FIGS. 7 and 8A show the results of the SSA reporter assay. The cleavage activity was calculated by using a 6bp spacer sequence as in the reporter analysis so far, and in terms of relative activity with respect to the cleavage activity of ZFA36-FokI which recognizes two target sequences on the left and right. FIG. 8B shows the results of the Cel-I assay.

The cleavage activity of the target sequence (ZFL1-ZFL1) on the reporter was measured with a construct in which each nuclease domain was connected to ZFL1 so as to be a homodimer, and the activity of ND1 and ND2 was higher than that of FokI-ND, similar to the results shown in FIG. 1C (FIG. 7A). From this result, it has been clarified that the high cleavage activity of the novel nuclease domains ND1 and ND2 is universal even when different ZF arrays are used.

When a homodimer was formed using a construct connecting ZFL1 and nuclease domains to measure the cleavage activity of the target sequence (ZFL1-ZFA36) on the reporter, ND1 had about 40% cleavage activity, but in FokI-ND and ND2, almost no cleavage activity was observed (FIG. 8A). On the other hand, when a homodimer was formed by the construct connecting the ZF array (ZFA36) used in Examples 2 to 6 and the nuclease domains to perform the analysis in the same manner, cleavage activity was also observed in FokI-ND and ND2, which were about 35% and about 50%, respectively. Further, in ND1, the cleavage activity was higher, about 90% (FIG. 8A).

When a heterodimer was formed using a ZFN construct, in which the ZF arrays of the homodimer type nuclease domains were ZFA36 and ZFL1, to analyze the cleavage activity, the activities of ND1 and ND2 were higher than those of FokI-ND as in the case of analysis with ZFA36 alone (FIG. 8A). From this, it has also been found that ND1 and ND2 have high cleavage activity and are universal regardless of the ZF array.

Next, in order to verify whether a dimer is formed and exhibits cleavage activity when only each heterodimer type nuclease domain is expressed, the cleavage activity of the target sequence (ZFL1-ZFL1 or ZFA36-ZFA36) on the reporter was measured. A DDD-type mutation was introduced into each nuclease domain connected to ZFL1, and an RRR-type mutation was introduced into each nuclease domain connected to ZFA36, and as a result of reporter analysis, almost no cleavage activity was observed in each of the DDD-type mutant ZFL1-ND and the RRR-type mutant ZFA36-ND alone (FIGS. 7A and 7B). From this, it has been clarified that even in the novel nuclease domains ND1 and ND2, homodimers cannot be formed by introducing amino acid substitutions into DDD-type/RRR-type, as in the case of FokI-ND.

Each nuclease domain was transduced to form a heterodimer type to measure the cleavage activity of the target sequence (ZFL1-ZFA36) on the reporter. FIG. 8A shows the results. The cleavage activity in FokI-ND was reduced to about 60% of the target. However, in ND1, even in the heterodimer type, no decrease in cleavage activity was observed, and the activity was as high as about 1.6 times that of the target. On the other hand, in ND2, the cleavage activity almost disappeared when the heterodimer type was used. From these results, it has been clarified that ND1 is capable of functional conversion to a heterodimer type having higher cleavage activity than FokI-ND.

Furthermore, in order to clarify the mutagenesis efficiency of each heterodimer type nuclease into the genome target sequence, analysis by Cel-I was performed (FIG. 8B). As shown in Table 1, the target base sequences on the genome were completely identical at the 1st site. Genomes were prepared from CHO-K1 cells expressing homodimer type and heterodimer type nucleases, and PCR fragments containing these target sequences were treated with Cel-I. Then, in the homodimer type, each nuclease domain cleaved the target genomic DNA, similar to the results previously obtained. On the other hand, in the heterodimer type, mutagenesis was observed in FokI-ND as well as the results of SSA reporter analysis, but the mutagenesis rate was higher in ND1. In ND2, no detectable mutagenesis was observed even in the target genome sequence, and it was considered that the cleavage activity was lost.

These results suggest that, unlike FokI-ND, ND1 is capable of functional conversion to a heterodimer type that maintains high activity, and also that conversion to the heterodimer type may result in significant structural changes in ND2, which means that each structural property is different from FokI-ND.

Example 8

Effect on Cleavage Activity Using Combination of Heterodimer Type Nuclease Domains Further analysis was conducted to determine whether it is possible to exhibit higher cleavage activity than conventional FokI-ND by changing the combination of nuclease domains during heterodimer formation.

Figure 9A:
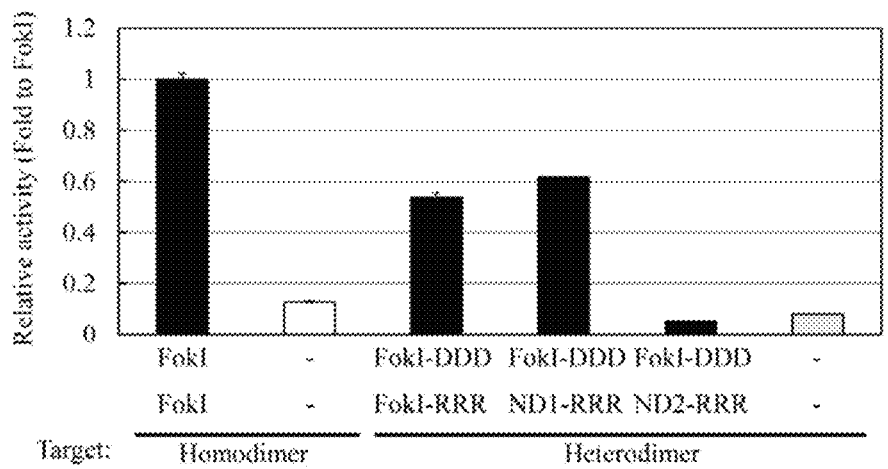
FIGS. 9A-9C show the nuclease activity of hybrid ZFNs as measured by a cell-based SSA assay. A HEK293T cell-based SSA assay. HEK293T cells were co-transfected with each pair of ZFN expression plasmids, reporter plasmids, and reference plasmid to perform a dual luciferase assay. After transfection, cells were incubated for 24 hours, lysed, and analyzed for luciferase activity. The white and gray bars indicate the absence of ZFA36-FokI and ZFN, respectively.
Figure 9B:
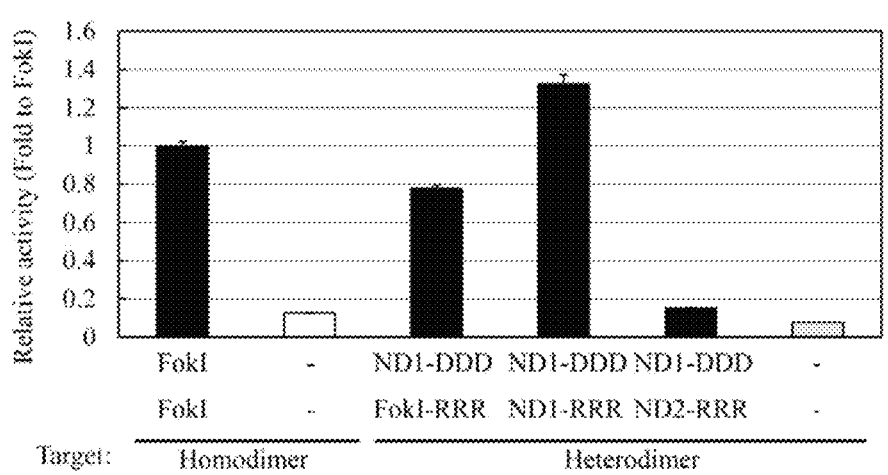
Figure 9C:
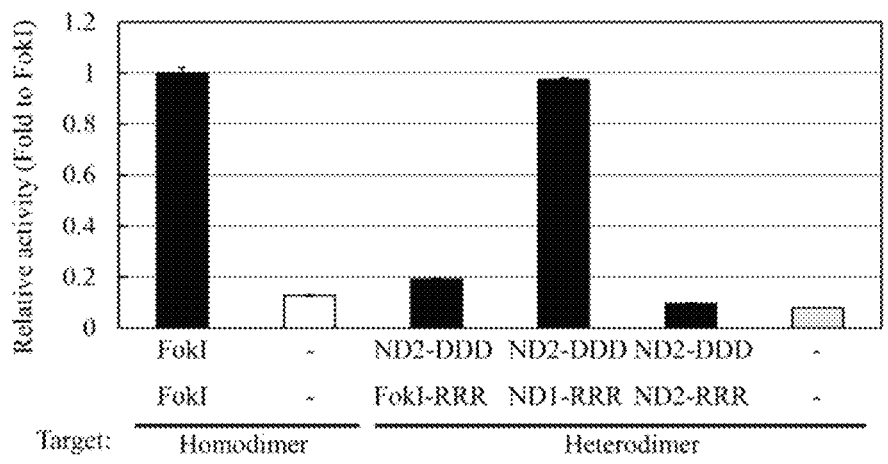

The DDD-type mutant ZFL1-ND and RRR-type mutant ZFA36-ND prepared in Example 7 were used in various combinations, and the nuclease activity was measured by the SSA reporter assay in the same manner as described in Example 2. FIGS. 9A-9C show the results.

When analysis was performed with a DDD-type mutation FokI-ND and each nuclease domain introduced with the RRR-type mutation, no increase in the cleavage activity of the reporter was observed even when combined with ND1 having a high cleavage activity so far, and it was about 60% of the cleavage activity of the FokI-ND homodimer type. In addition, almost no cleavage activity was observed in combination with ND2 (FIG. 9A).

The DDD-type mutant ND1 had a cleavage activity of about 80% in combination with the RRR-type mutant FokI-ND, and meanwhile, in combination with the RRR-type mutant ND2, the cleavage activity was almost lost as in the case of the DDD-type mutant FokI-ND (FIG. 9B).

Unlike the results of the DDD-type mutant FokI-ND and the DDD-type mutant ND1, the DDD-type mutant ND2 showed high cleavage activity only in combination with the RRR-type mutant ND1, and almost lost its cleavage activity in combination with the RRR-type mutant FokI-ND or the RRR-type mutant ND2 (FIG. 9C). As a result, it has been clarified that in the case of the heterodimer type of the RRR-type mutant ND2, the cleavage activity is lost regardless of the combination of nuclease domains.

It has been found that a combination of heterodimer type nuclease domains showing cleaving activity is possible, and in the amino acid substitution analyzed this time, it is possible to enhance the cleavage activity only in the combination of the DDD-type mutant ND1 and the RRR-type mutant ND1. In addition, it has been revealed that the combination of the DDD-type mutant ND2 and the RRR-type mutant ND1 also has the same cleavage activity as the homodimer of FokI-ND. From the above results, it has been found that when ND1 and ND2 form a dimer, structural properties different from those of FokI-ND take action.

Example 9

Analysis at Base Sequence Level of Mutagenesis by ZFN

Investigation was made as to what change would take place in the base sequence due to the mutagenesis into the target sequence by ZFN.
(1) Sequence Analysis In order to clarify what change would be brought to the base sequence by the mutagenesis by ZFN into the target sequences (1st site and 2nd site) of ZFA36 existing on the genome sequence of CHO-K1 cells, sequence analysis of the genomic region containing the target sequences was performed as follows. In the same manner as in the Cel-I assay described in Example 3, PCR was performed using KOD Fx Neo with the CHO-K1 genomic DNA transduced with each ZFN as a template. The obtained PCR product was subjected to TA cloning after A-addition to the PCR product by TArget clone plus (Toyobo). The PCR product was cloned in *Escherichia coli*, at least 16 independent *Escherichia coli* transformants were randomly selected, and each plasmid thereof was extracted. M13-f primers were added so that the obtained plasmid had a final concentration of 6.4 pmol at 400 ng, and Fasmac was requested to carry out PCR and sequence analysis. From the obtained sequence, the mutant sequence of the target sequence in each ZFN and its ratio were calculated.
(2) Results FIG. 10 shows the results. At the 1st site of ZFA36-ZFA36, FokI-ND obtained 1 clone with 1-base insertion and 3 clones with 4-base insertion among the 17 clones analyzed. Of the 14 clones that could be analyzed in ND1, there was 1 clone for each of 1-base insertion, 2-base deletion, and 8-base deletion. Furthermore, 2 clones of mutation were obtained with 2-base insertion and 1-base deletion, and 6 clones of mutation were obtained with 4-base insertion, which was the largest number in this analysis. Of the 13 clones that could be analyzed in ND2, there was 1 clone obtained for each of 1-base insertion, 2-base insertion, 2-base deletion, and 4-base deletion. In the 15 clones of ND3 and the 16 clones of ND4 that could be analyzed, no base insertion or deletion was observed in the analysis of the ZFA36-ZFA36 1st site this time. In addition, the mutagenesis of each nuclease domain at the 2nd site of the ZFA36 target sequence was analyzed. Then, in FokI, of the 20 clones analyzed, there was 1 clone obtained for each of 2-base insertion, 5-base insertion, and 2-base deletion, and 1 clone was obtained with insertion exceeding 230 bases. In addition, similar to the ZFA36 1st site, the most mutations were 4-base insertion, and 3 clones were obtained. In ND1, of the 17 clones analyzed, there were 2 clones obtained for each of 2-base deletion and 4-base deletion. In addition, 3 clones were obtained with 4-base insertion, and 6 clones were obtained with 2-base insertion which was most frequent in this analysis. Of the 16 clones analyzed in ND2, 1 clone was obtained with 1-base insertion, 2 clones were obtained with 2-base insertion, and 5 clones were obtained with 4-base insertion which was most frequent in the analysis. In addition, 1 clone was obtained with as large a base insertion as 71 bases. In ND3, unlike the 1st site, mutagenesis was present in the target sequence at the 2nd site, and in the analyzed 16 clones, there was 1 clone obtained for each of 2-base insertion, 2-base deletion, and 8-base deletion. In ND4, in all 14 clones that could be analyzed, no mutagenesis was observed in the target sequence at the 2nd site as well as at the 1st site.

As a result of sequence analysis, as for the mutagenesis into the target sequence by ND1 and ND2, many clones were observed with 4-bases insertion similar to FokI-ND, but various patterns not seen in FokI-ND were seen as mutations to the genome. The overhang of the base generated by the novel nuclease domains may differ from the FokI nuclease domain. Table 3 shows the mutation rates of ZFA36 obtained by sequence analysis at each target site. Under these analysis conditions, it has been clarified that, also in the sequence analysis, the mutagenesis rate of each nuclease domain in the target genome sequence is similar to that in the Cel-I assay.

TABLE 3

| | Genome Editing Mutation Rate in Sequence Analysis | |
|---|---|---|
| ZFA36-ND | ZFA36-ZFA36 1st site | ZFA36-ZFA36 2nd site |
| FokI-ND | 4/17 (23.5%) | 7/20 (35.0%) |
| ND1 | 11/14 (78.6%) | 13/17 (76.5%) |
| ND2 | 4/13 (30.8%) | 9/16 (56.3%) |
| ND3 | 0/15 (0.0%) | 3/16 (18.8%) |
| ND4 | 0/16 (0.0%) | 0/14 (0.0%) |

Example 10

Cleavage Activity of Novel Nuclease Domains Combined with Nucleic Acid-Binding Domain Other Than ZFA In order to clarify whether the novel nuclease domains of the present invention have higher cleavage activity than FokI-ND even when using a nucleic acid-binding domain other than ZFA, an artificial nucleic acid-cleaving enzyme containing ND1 and TALE was prepared, and its cleaving activity was measured. Specifically, TALE-FokI-ND and TALE-ND1 were prepared using the Platinum TALEN (doi: 10.1038/srep03379) technology developed in the laboratory of the present inventors, and their cleavage activity was evaluated by the SSA reporter assay method.
(1) Construction of Destination Vector for TALE-ND1
Platinum TALEN destination vector ptCMV-153/47-VR-NG
(https://www.addgene.org/50704/addgene.org/50704/) uninserted with the nucleic acid binding module was used as a template, and a ptTALE-nuclease domain replacement primer pair (for vector amplification) was used for amplification by PrimeStar Max, to thereby obtain vector fragments. In addition, a ptTALE-nuclease domain replacement primer pair (for insert amplification) was used to obtain insert fragments of ND1. These vector fragments and insert fragments were mixed to carry out an In-Fusion reaction. After transformation of *Escherichia coli*, a plasmid was extracted from the obtained transformant to obtain a target destination vector of TALE-ND1 (a vector in which FokI-ND in ptCMV-153/47-VR-NG was replaced with ND1).

(2) Incorporation of Nucleic Acid Binding Module and Construction of SSA Reporter Plasmid The nucleic acid binding module for recognizing the sequences of ROSA26 locus and HPRT1 locus of CHO-K1 cells was incorporated into the destination vector obtained in (1) above by the Golden Gate method (based on the method described in doi: 10.1038/srep03379). This was used to transform *Escherichia coli*, and the desired plasmids (TALE-ROSA26-ND1 and TALE-HPRT1-ND1) were obtained from the obtained transformants. In addition, for TALEN (TALE-FokI) holding the conventional FokI-ND, constructs (TALE-ROSA26-FokI and TALE-HPRT1-FokI) incorporating a nucleic acid binding module were prepared in the same manner. As for the SSA reporter plasmids, those containing the respective target sequences (SSA-CHO-ROSA26 reporter and SSA-CHO-HPRT1 reporter) were prepared by a conventional method. Table 4 below shows the target sequences for the ROSA26 locus and HPRT1 locus.

TABLE 4

Target Sequences at ROSA26 Locus and HPRT1 Locus of CHO-K1 Cells

ROSA26:

5'-TGCCCAGAAGACTCCCGcccatctcccagaaaGCCTCGACTTGCAGA
TCA-3'
3'-ACGGGTCTTCTGAGGGCgggtagagggtctttCGGAGCTGAACGTCT
AGT-5'

HPRT1:

5'-TGAACCAGGCTATGACCTagatttattttgtatTCCTAATCACTATG
TCGA-3'
3'-ACTTGGTCCGATACTGGAtctaaataaaacataAGGATTAGTGATAC
AGCT-5'

The underlines mean the DNA recognition sequences of TALEN (left side and right side) at each locus, and the lowercase letters mean the spacer sequence between the DNA recognition sequences.

(3) Introduction into Cells and Reporter Assay

By use of the TALEN plasmids (TALE-FokI-ND and TALE-ND1) incorporating the nucleic acid binding module for recognizing the target sequence, and the SSA reporter plasmids incorporating the target sequence prepared in (2) above, transduction was performed on HEK293T cells using Lipofectamine LTX, and using the cells 24 hours after transduction, SSA reporter assay was performed in the same manner as in Example 2. As controls, a ZFN plasmid containing FokI-ND (pSTL-ZFA36) and a plasmid pSTL expressing only FokI-ND were used to perform measurement in a similar manner. The cleavage activity of each TALE-ND was calculated as a relative activity when the value of the cleavage activity of ZFA36-FokI with respect to the reporter containing the target sequence of ZFA36 was set to 1.

(4) Results

Figure 11A:
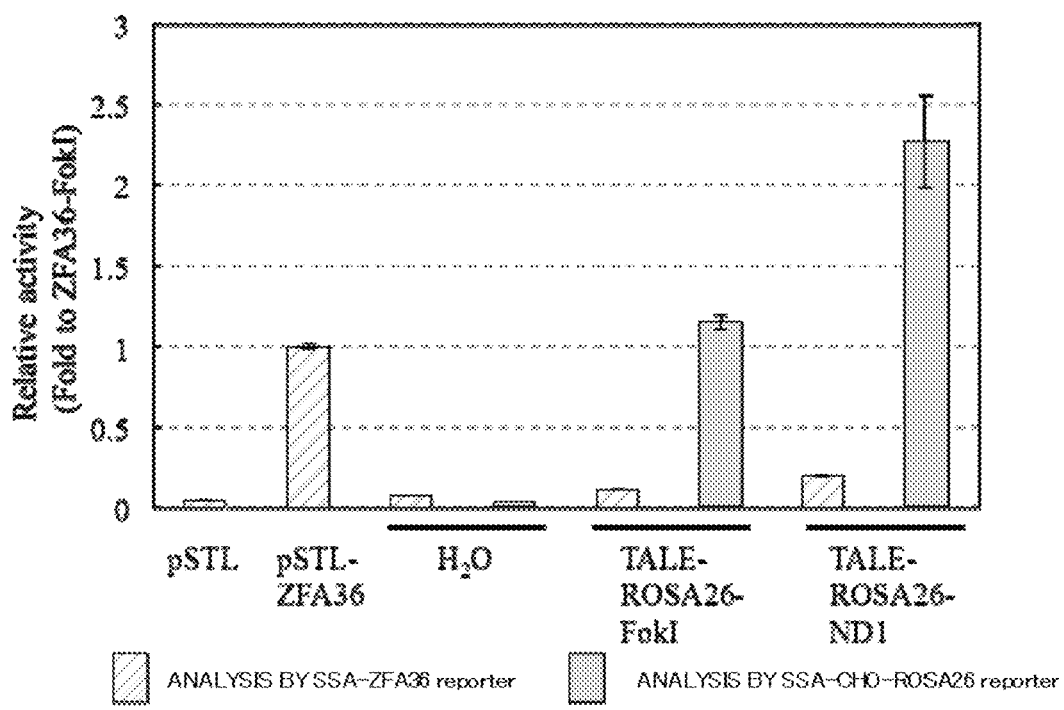
FIG. 11A shows the results of a cleavage test of an artificial nucleic acid-cleaving enzyme containing the novel nuclease domain of the present invention and TALE, which was performed in Example 10. In the figure, "FokI" means FokI-ND.
Figure 11B:
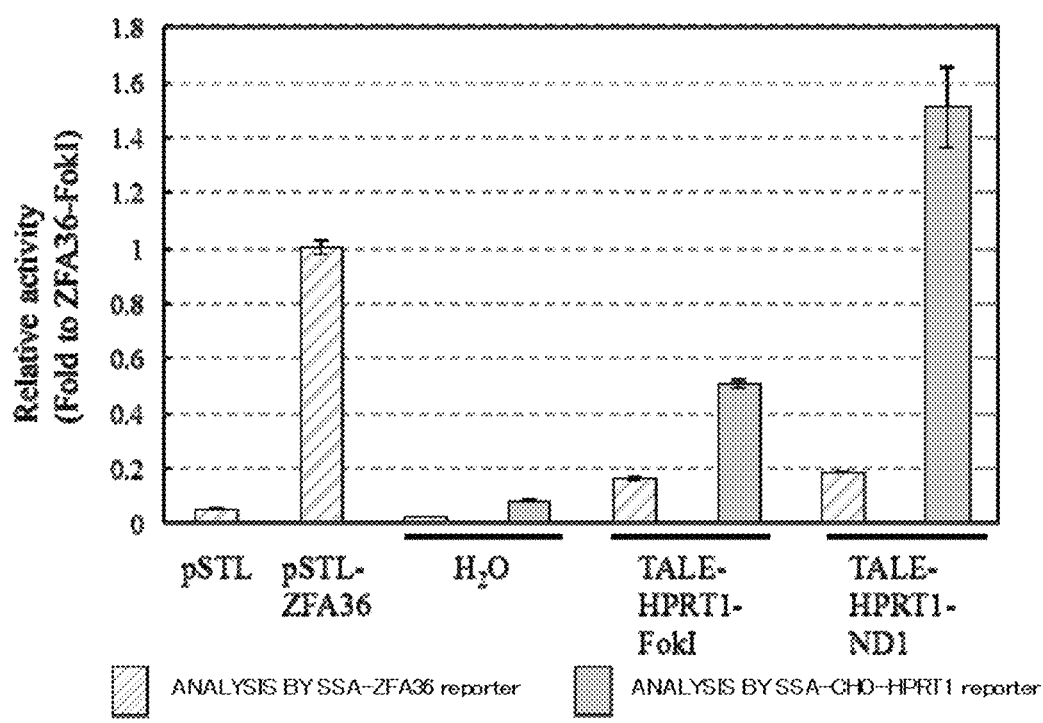
FIG. 11B shows the results of a cleavage test of an artificial nucleic acid-cleaving enzyme containing the novel nuclease domain of the present invention and TALE, which was performed in Example 10. In the figure, "FokI" means FokI-ND.

FIGS. 11A and 11B show the results. FIG. 11A shows the results when the sequence derived from the ROSA26 locus was the target, and FIG. 11B shows the results when the sequence derived from the HPRT1 locus was the target.

As is clear from FIG. 11A, in TALE-ROSA26-FokI in which the nuclease domain of Platinum TALEN is conventional FokI-ND, it has been revealed that the cleavage activity of the reporter targeting the sequence derived from the ROSA26 locus has an activity close to the cleavage activity of ZFA36-FokI targeting the ZFA36 reporter. On the other hand, in TALE-ROSA26-ND1 in which the nuclease domain of Platinum TALEN is replaced with ND1, it has been revealed that the cleavage activity of the reporter targeting the sequence derived from the ROSA26 locus is about twice as high as that of TALE-ROSA26-FokI. Based on the above, when targeting the ROSA26 locus-derived sequence of the endogenous genome of CHO-K1 cells, it has been revealed that TALE-ND1 has a higher cleavage activity in the nuclease domain than the conventional FokI-ND, TALE-FokI.

In addition, a sequence derived from the HPRT1 locus, which is a locus different from the ROSA26 locus, was targeted and analyzed in the same manner. As a result, as is clear from FIG. 11B, in TALE-HPRT1-FokI in which the nuclease domain of Platinum TALEN is conventional FokI-ND, it has been revealed that the cleavage activity of the reporter targeting the HPRT1 locus-derived sequence is about half of the cleavage activity of ZFA36-FokI targeting the ZFA36 reporter. On the other hand, in TALE-HPRT1-ND1 in which the nuclease domain of Platinum TALEN is replaced with ND1, the cleavage activity of the reporter targeting the HPRT locus-derived sequence was about twice as high as that of TALE-FokI, and the same result as that of the ROSA26 locus-derived sequence was obtained.

From these results, it has been clarified that TALE-ND1 having ND1 as the nuclease domain of Platinum TALEN shows higher cleavage activity than TALE-FokI having the conventional FokI-ND. From the above, it has been suggested that the novel nuclease domains of the present invention are nuclease domains having better cleavage activity than FokI-ND even when in the case of using not only ZFN but also other nucleic acid binding domains.

From the above, it has been demonstrated that the novel nuclease domains of the present invention have the following main characteristics.

(i) ND1 and ND2 of the present invention, especially ND1, have significantly higher cleavage activity than FokI-ND. In addition, since ND1 shows a cleavage activity higher than FokI-ND even in ZF array that recognizes other sequences and in TALE, the effect of increasing cleavage activity by ND1 is universal.

(ii) By modifying the linker between the ZF array and ND, ND1 exhibits about the same cleavage activity as the 6bp spacer even with a 5bp or 7bp spacer, and therefore ND1 has higher flexibility than FokI-ND in dimerization and can relax the restriction of the target sequence.

(iii) By introducing a DDD-type mutation and an RRR-type mutation into ND1 and ND2, homodimerization can be suppressed as in FokI-ND. Furthermore, by combining ZFL1-DDD and ZFA36-RRR, cleavage with a heterodimer is possible in ND1. Further, since the cleavage activity at that time is about the same as that of the wild-type ND1, it is possible to obtain a nuclease domain having both high specificity and high cleavage activity by using ND1-DDD/RRR. (iv) When the activity was verified by combining DDD/RRR-type FokI-ND, ND1, and ND2 with each other, it was revealed that the pair of ND1-DDD and ND1-RRR showed the highest activity among all the combinations, demonstrating the superiority of the ND1-DDD/ND1-RRR heterodimer system.

Example 11

Preparation of Protein in *Escherichia Coli*

(1) Construction of Expression Vectors for ZF-ND1 and ZF-FokI

The XhoI site and SalI site of the pET-MCS plasmid containing a His tag at the N-terminus were cleaved, and a ZF-ND1 fragment was inserted. The ZF-ND1 fragment contains the nuclear localization signal NLS, Zinc-Finger (hereinafter abbreviated as ZF), and the nuclease domain ND1. As ZF, a domain that recognizes two types of sequences was used. One is ZFA36, which recognizes the 12 base pair DNA sequence GAAGATGGT. The other is ZFL1, which recognizes the 12 base pair DNA sequence GAAGGTGAC. Therefore, as plasmids expressing ZF (ZFA36A)-ND1 and ZF (ZFL1)-ND1, pET-ZF (ZFA36A) ND1 and pET-ZF (ZFL1) ND1 were prepared, respectively.

Based on the above plasmids, plasmids in which the nuclease domain of the restriction enzyme FokI (hereinafter abbreviated as FokI) was inserted instead of ND1, pET-ZF (ZFA36A)-FokI, and pET-ZF (ZFL1)-FokI were prepared. The amino acid sequences of ZF (ZFA36A)-ND1, ZF (ZFL1)-ND1, ZF (ZFA36A)-FokI, and ZF (ZFL1)-FokI are set forth in SEQ ID NOs: 119 to 122.

(2) Expression and Purification of ZF-ND1 Protein in *Escherichia Coli*

The pET plasmid expressing ZF-ND1 or ZF-FokI, and pRARE2 (Stratagene) were transformed into *Escherichia coli* strain BL21 (DE3) and cultured in LB medium containing kanamycin and chloramphenicol. The transformed *Escherichia coli* was cultured at 37° C. until the OD (absorbance at 600 nm) became 0.6, and then cultured at 18° C. for 1 hour. Isopropyl β-D-1-thiogalactopyranoside (IPTG) was added to a final concentration of 0.1 mM to induce protein expression. After further shaking and culturing at 18° C. for 17 hours, *Escherichia coli* was lysed using a lysis buffer (20 mM Tris-HCl, 500 mM NaCl, 10% glycerol, 10 mM imidazole, 1 mM benzyl sulfonyl fluoride, 1 mM dithiothreitol, pH 8.0). Subsequently, the protein was adsorbed on a nickel NTA column, and a washing buffer (20 mM Tris-HCl, 500 mM NaCl, 10% glycerol, 20 mM imidazole, pH 8.0) was used to remove impurities. Elution of the protein was performed using an elution buffer (20 mM Tris-HCl, 500 mM NaCl, 10% glycerol, 500 mM imidazole, pH 8.0). A portion of the eluted protein was dissolved in SDS sample buffer for protein yield analysis. The eluted protein was purified using gel filtration chromatography HiPrep 16/60 Sephacryl S-200 HR (GE healthcare, United States, Illinois) and buffer A (20 mM HEPES, 150 mM NaCl, 10% glycerol, pH 7.4), frozen instantly with liquid nitrogen, and then stored at −80° C. For analysis of protein yield, the imidazole-eluted protein fraction and the final purified protein were dissolved in SDS sample buffer and electrophoresed by SDS-PAGE. During electrophoresis, a known concentration of BSA protein was electrophoresed in another lane, the gel after PAGE was stained with Coomassie, the band of the target protein molecular weight was quantified by ChemiDoc XRS+, and the protein yield was analyzed from the protein molecular weight.

(3) Results

When expressing and purifying ZFN proteins in *Escherichia coli*, there is a problem that the protein yield is low. It is considered the fundamental properties of ZFN proteins are that they are low in solubility, resulting in aggregation. It was verified how soluble the protein of the novel ND1 was compared to the FokI as the conventional art.

TABLE 5

| | Protein Yield per 1 L of *Escherichia Coli* Culture (nmol/culture 1 L) | Increase (Times) in Protein Yield of ND1 When Compared to FokI |
|---|---|---|
| ZF(ZFA36A)-ND1 Protein | 104.8 | 11 |
| ZF(ZFA36A)-FokI Protein | 9.3 | (1) |
| ZF(ZFL1)-ND1 Protein | 67.6 | 13 |
| ZF(ZFL1)-FokI Protein | 5.0 | (1) |

As shown in Table 5, when ZF-ND1 was expressed in *Escherichia coli*, it was generally more soluble than ZF-FokI, and the yield per 1 L of *Escherichia coli* culture was improved. The higher the solubility, the higher the concentration of protein that can be introduced, which therefore is particularly convenient for genome editing using protein.

Example 12

Activity of ZF-ND1 and ZF-FokI in Plant Cells (1) Construction of Reporter Cells In order to evaluate the activity of ZF-ND1 or ZF-FokI, reporter cells were constructed that expresses a full-length 2.1 kb GUS (β-glucuronidase) gene when SSA (single-strand annealing) after DNA cleavage is induced. Specifically, 1.8 kb from the upstream of the GUS gene, the recognition sequence of ZFA36 (GAAGCTGGT), and 0.8 kb from the downstream of the GUS gene were introduced into pCAMBIA 1305.2 (Marker Gene). Regarding 1.8 kb from the upstream of the GUS gene and 0.8 kb from the downstream of the GUS gene, they have 500 bp as a common sequence (overlap region). This vector was transformed via *Agrobacterium* into an *Arabidopsis thaliana* T87 cultured cell line (RIKEN), and the established cell line was designated as T87-GUUS (ZFA36). Since the expression of GUS can be easily visualized and detected using the blue staining reagent X-Gluc, the detection of the GUS protein allows the evaluation of the introduction of ZF-ND1 or ZF-FokI into the nucleus and the SSA-inducing activity.

(2) Introduction by Electroporation Method

Figure 12A:
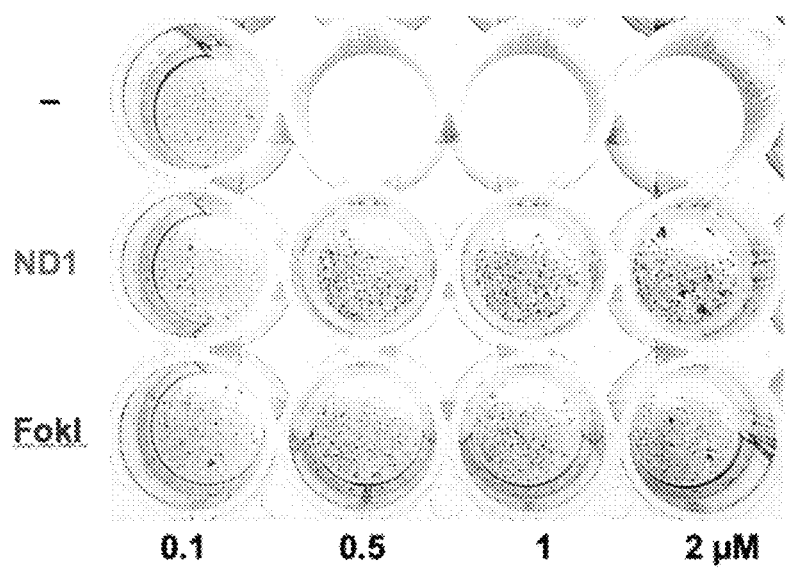
FIG. 12A shows the results of detecting by SSA reporter assay the nuclease activity of ZF-ND1 and ZF-FokI introduced into plant cells by the electroporation method.
Figure 12B:
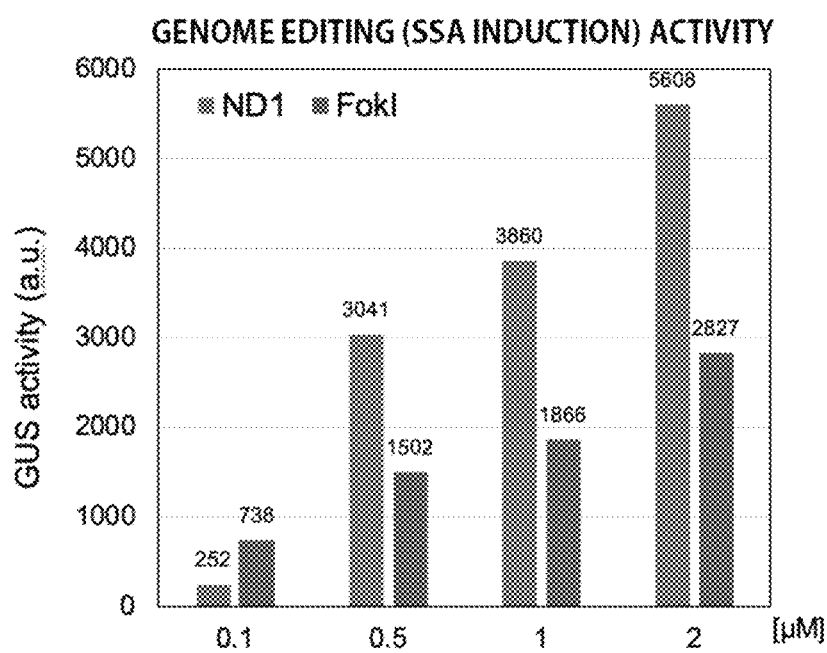
FIG. 12B is a graph of the results of FIG. 12A.

The protein prepared in Example 11 was introduced by the electroporation method. The established T87-GUUS (ZFA36) cells were used to attempt to introduce ZF-ND1 and ZF-FokI by electroporation into T87 cells having a cell wall. NEPA21 Type II sold by Neppa Gene was used for electroporation. Electroporation was performed using Opti-MEMI buffer, and the GUS activity was evaluated two days later. As a result, as shown in FIGS. 12A-12B, when electroporation was performed using Opti-MEMI, a very large number of cells expressed GUS. In the experiment using the ZF-ND1 protein, it was found that the SSA-inducing activity was about twice as high as that in the case of using the ZF-FokI protein. In the experiment, it has been found that, when introduced not only as a gene expression vector but also as a protein, ZF-ND1 has higher activity than that of ZF-FokI, and that ZF-ND1 has higher activity than ZF-FokI not only in animal cells but also in plant cells.

(3) Introduction by Protein Transduction Method

Figure 13:
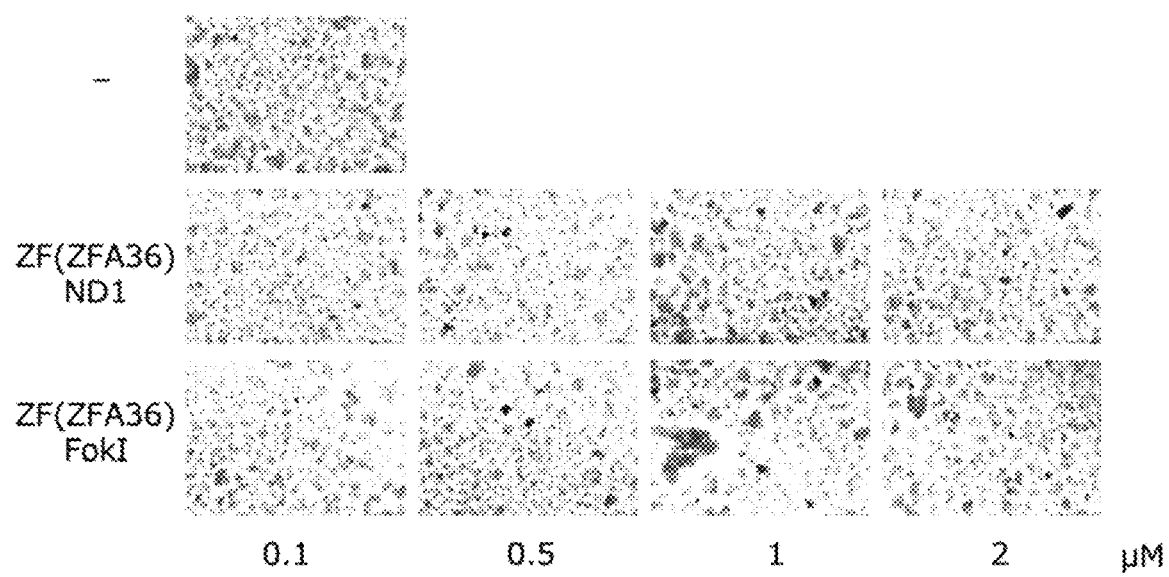
FIG. 13 shows the results of detecting by SSA reporter assay the nuclease activity of ZF-ND1 and ZF-FokI introduced into plant cells by the protein transduction method.

The protein prepared in Example 11 was used to attempt introduction by the protein transduction method. That is, to T87-GUUS (ZFA36) having a cell wall, ZF (ZFA36A)-ND1 protein or ZF (ZFA36A)-FokI protein having a final concentration of 0.1 to 2 μM was added, and then, after 1 hour, the mixture was washed with a culture medium and cultured for 3 days. When the protein was added, no biochemical treatment such as protease treatment or physicochemical treatment such as electroporation was performed. Therefore, spontaneous intake of the protein was expected. As a result, as shown in FIG. 13, although it is a small proportion compared to the electroporation method, it has been revealed that the ZF (ZFA36A)-ND1 protein and the ZF (ZFA36A)-FokI protein are taken in by the protein transduction method, allowing genome editing. When the protein transduction method was used, the activity of ZF (ZFA36A)-ND1 was equal to or higher than that of ZF (ZFA36A)-FokI.

INDUSTRIAL APPLICABILITY

The novel nuclease domains of the present invention have excellent properties different from the nuclease domain of FokI, and the artificial nucleic acid-cleaving enzyme containing the nuclease domains of the present invention is very useful as a genome editing tool.

Sequence Listing Free Text

SEQ ID NO: 9; ND1 substitution forward primer
SEQ ID NO: 10; ND1 substitution reverse primer
SEQ ID NO: 11; ND2 substitution forward primer
SEQ ID NO: 12; ND2 substitution reverse primer
SEQ ID NO: 13; ND3 substitution forward primer
SEQ ID NO: 14; ND3 substitution reverse primer
SEQ ID NO: 15; ND4 substitution forward primer
SEQ ID NO: 16; ND4 substitution reverse primer
SEQ ID NO: 17; forward primer for linker alteration, ZFN-FokI-GS-F
SEQ ID NO: 18; reverse primer for linker alteration, ZFN-GS-inverse-R
SEQ ID NO: 19; forward primer for linker alteration, ZFN-ND1-GS-F
SEQ ID NO: 20; reverse primer for linker alteration, ZFN-GS-inverse-R
SEQ ID NO: 21; forward primer for linker alteration, ZFN-ND2-GS-F
SEQ ID NO: 22; reverse primer for linker alteration, ZFN-GS-inverse-R
SEQ ID NO: 23; forward primer for linker alteration, ZFN-FokI-RPGEKP-F
SEQ ID NO: 24; reverse primer for linker alteration, ZFN-RPGEKP-R
SEQ ID NO: 25; forward primer for linker alteration, ZFN-ND1-RPGEKP-F
SEQ ID NO: 26; reverse primer for linker alteration, ZFN-RPGEKP-R
SEQ ID NO: 27; forward primer for linker alteration, ZFN-ND2-RPGEKP-F
SEQ ID NO: 28; reverse primer for linker alteration, ZFN-RPGEKP-R
SEQ ID NO: 29; forward primer for linker alteration, ZFN-FokI-TGPGAAARA-F
SEQ ID NO: 30; reverse primer for linker alteration, ZFN-FokI-TGPGAAARA-R
SEQ ID NO: 31; forward primer for linker alteration, ZFN-ND1-TGPGAAARA-F
SEQ ID NO: 32; reverse primer for linker alteration, ZFN-FokI-TGPGAAARA-R
SEQ ID NO: 33; forward primer for linker alteration, ZFN-ND2-TGPGAAARA-F
SEQ ID NO: 34; reverse primer for linker alteration, ZFN-FokI-TGPGAAARA-R
SEQ ID NO: 35; forward primer for Sharkey mutation introduction in FokI-ND
SEQ ID NO: 36; reverse primer for Sharkey mutation introduction in FokI-ND
SEQ ID NO: 37; forward primer for Sharkey mutation introduction in ND1
SEQ ID NO: 38; reverse primer for Sharkey mutation introduction in ND1
SEQ ID NO: 39; forward primer for Sharkey mutation introduction in ND2
SEQ ID NO: 40; reverse primer for Sharkey mutation introduction in ND2
SEQ ID NO: 41; ZFA substitution forward primer
SEQ ID NO: 42; ZFA substitution reverse primer
SEQ ID NO: 43; forward primer for FokI-DDD mutation introduction
SEQ ID NO: 44; reverse primer for FokI-DDD mutation introduction
SEQ ID NO: 45; forward primer for ND1-DDD mutation introduction
SEQ ID NO: 46; reverse primer for ND1-DDD mutation introduction
SEQ ID NO: 47; forward primer for ND2-DDD mutation introduction
SEQ ID NO: 48; reverse primer for ND2-DDD mutation introduction
SEQ ID NO: 49; forward primer for FokI-RRR vector mutation introduction
SEQ ID NO: 50; reverse primer for FokI-RRR vector mutation introduction
SEQ ID NO: 51; forward primer for FokI-RRR insert mutation introduction
SEQ ID NO: 52; reverse primer for FokI-RRR insert mutation introduction
SEQ ID NO: 53; forward primer for ND1-RRR vector mutation introduction
SEQ ID NO: 54; reverse primer for ND1-RRR vector mutation introduction
SEQ ID NO: 55; forward primer for ND1-RRR insert mutation introduction
SEQ ID NO: 56; reverse primer for ND1-RRR insert mutation introduction
SEQ ID NO: 57; forward primer for ND2-RRR vector mutation introduction
SEQ ID NO: 58; reverse primer for ND2-RRR vector mutation introduction
SEQ ID NO: 59; forward primer for ND2-RRR insert mutation introduction
SEQ ID NO: 60; reverse primer for ND2-RRR insert mutation introduction
SEQ ID NO: 61; M13-F primer
SEQ ID NO: 62; CHO-K1 ZFA36-ZFA36 target 1st site
SEQ ID NO: 63; CHO-K1 ZFA36-ZFA36 target 2nd site
SEQ ID NO: 64; CHO-K1 ZFA36-ZFA36 target 3rd site
SEQ ID NO: 65; CHO-K1 ZFL1-ZFA36 target 1st site
SEQ ID NO: 66; CHO-K1 ZFL1-ZFA36 target 2nd site
SEQ ID NO: 67; FokI-DDD amino acid sequence
SEQ ID NO: 68; FokI-RRR amino acid sequence
SEQ ID NO: 69; ND1-DDD amino acid sequence
SEQ ID NO: 70; ND1-RRR amino acid sequence
SEQ ID NO: 71; ND2-DDD amino acid sequence
SEQ ID NO: 72; ND2-RRR amino acid sequence
SEQ ID NO: 73; FokI-S418P/K441E amino acid sequence
SEQ ID NO: 74; ND1-S418P/K441E amino acid sequence
SEQ ID NO: 75; ND2-S441E amino acid sequence
SEQ ID NO: 76; FokI-cleaved CHO-K1 ZFA36-ZFA36 target 1st site SEQ ID NO: 77; FokI-cleaved CHO-K1 ZFA36-ZFA36 target 1st site
SEQ ID NO: 78; FokI-cleaved CHO-K1 ZFA36-ZFA36 target 1st site
SEQ ID NO: 79; ND1-cleaved CHO-K1 ZFA36-ZFA36 target 1st site
SEQ ID NO: 80; ND1-cleaved CHO-K1 ZFA36-ZFA36 target 1st site
SEQ ID NO: 81; ND1-cleaved CHO-K1 ZFA36-ZFA36 target 1st site
SEQ ID NO: 82; ND1-cleaved CHO-K1 ZFA36-ZFA36 target 1st site
SEQ ID NO: 83; ND1-cleaved CHO-K1 ZFA36-ZFA36 target 1st site
SEQ ID NO: 84; ND1-cleaved CHO-K1 ZFA36-ZFA36 target 1st site
SEQ ID NO: 85; ND2-cleaved CHO-K1 ZFA36-ZFA36 target 1st site
SEQ ID NO: 86; ND2-cleaved CHO-K1 ZFA36-ZFA36 target 1st site
SEQ ID NO: 87; ND2-cleaved CHO-K1 ZFA36-ZFA36 target 1st site
SEQ ID NO: 88; ND2-cleaved CHO-K1 ZFA36-ZFA36 target 1st site
SEQ ID NO: 89; ND2-cleaved CHO-K1 ZFA36-ZFA36 target 1st site
SEQ ID NO: 90; ND3-cleaved CHO-K1 ZFA36-ZFA36 target 1st site
SEQ ID NO: 91; ND4-cleaved CHO-K1 ZFA36-ZFA36 target 1st site
SEQ ID NO: 92; FokI-cleaved CHO-K1 ZFA36-ZFA36 target 2nd site
SEQ ID NO: 93; FokI-cleaved CHO-K1 ZFA36-ZFA36 target 2nd site
SEQ ID NO: 94; FokI-cleaved CHO-K1 ZFA36-ZFA36 target 2nd site
SEQ ID NO: 95; FokI-cleaved CHO-K1 ZFA36-ZFA36 target 2nd site
SEQ ID NO: 96; FokI-cleaved CHO-K1 ZFA36-ZFA36 target 2nd site
SEQ ID NO: 97; FokI-cleaved CHO-K1 ZFA36-ZFA36 target 2nd site
SEQ ID NO: 98; ND1-cleaved CHO-K1 ZFA36-ZFA36 target 2nd site
SEQ ID NO: 99; ND1-cleaved CHO-K1 ZFA36-ZFA36 target 2nd site
SEQ ID NO: 100; ND1-cleaved CHO-K1 ZFA36-ZFA36 target 2nd site
SEQ ID NO: 101 ND1-cleaved CHO-K1 ZFA36-ZFA36 target 2nd site
SEQ ID NO: 102 ND1-cleaved CHO-K1 ZFA36-ZFA36 target 2nd site
SEQ ID NO: 103; ND2-cleaved CHO-K1 ZFA36-ZFA36 target 2nd site
SEQ ID NO: 104; ND2-cleaved CHO-K1 ZFA36-ZFA36 target 2nd site
SEQ ID NO: 105; ND2-cleaved CHO-K1 ZFA36-ZFA36 target 2nd site
SEQ ID NO: 106; ND2-cleaved CHO-K1 ZFA36-ZFA36 target 2nd site
SEQ ID NO: 107; ND2-cleaved CHO-K1 ZFA36-ZFA36 target 2nd site
SEQ ID NO: 108; ND3-cleaved CHO-K1 ZFA36-ZFA36 target 2nd site
SEQ ID NO: 109; ND3-cleaved CHO-K1 ZFA36-ZFA36 target 2nd site
SEQ ID NO: 110; ND3-cleaved CHO-K1 ZFA36-ZFA36 target 2nd site
SEQ ID NO: 111; ND3-cleaved CHO-K1 ZFA36-ZFA36 target 2nd site
SEQ ID NO: 112; ND4-cleaved CHO-K1 ZFA36-ZFA36 target 2nd site
SEQ ID NO: 113; forward primer for vector amplification for ptTALE-ND substitution, ptTALEN-inverse-F
SEQ ID NO: 114; reverse primer for vector amplification for ptTALE-ND substitution, NC-inverse-R 2
SEQ ID NO: 115; forward primer for insert amplification for ptTALE-ND substitution, ND1-NC-F v2
SEQ ID NO: 116; reverse primer for insert amplification for ptTALE-ND substitution, ND1-ptTALEN-R
SEQ ID NO: 117; target sequence on ROSA26 locus in CHO-K1 cell
SEQ ID NO: 118; target sequence on HPRT1 locus in CHO-K1 cell
SEQ ID NO: 119; ZF(ZFA36A)-ND1 amino acid sequence
SEQ ID NO: 120; ZF(ZFL1)-ND1 amino acid sequence
SEQ ID NO: 121; ZF(ZFA36A)-FokI amino acid sequence
SEQ ID NO: 122; ZF(ZFL1)-FokI amino acid sequence

The invention claimed is:

1. A combination of two artificial nucleic acid-cleaving enzymes comprising:

a first artificial nucleic acid-cleaving enzyme comprising a nuclease domain which is a polypeptide comprising the amino acid sequence set forth in SEQ ID NO 69 and a nucleic acid-binding domain, and a second artificial nucleic acid-cleaving enzyme comprising a nuclease domain which is a polypeptide comprising the amino acid sequence set forth in SEQ ID NO 70 and a nucleic acid-binding domain, wherein the nucleic acid-binding domain of the first artificial nucleic acid-cleaving enzyme and of the second artificial nucleic acid-cleaving enzyme is a zinc finger.

2. The combination of two artificial nucleic acid-cleaving enzymes according to claim 1, wherein each of the first and the second artificial nucleic acid-cleaving enzymes further comprises a linker located between the nuclease domain and the nucleic acid-binding domain.

3. An isolated nucleic acid comprising a nucleic acid sequence encoding the combination of two artificial nucleic acid-cleaving enzymes according to claim 1.

4. A vector comprising: the nucleic acid according to claim 3.

5. A method for modifying a target nucleic acid, comprising: introducing into a cell the combination of artificial nucleic acid-cleaving enzymes according to claim 1.

6. A kit for modifying a target nucleic acid, comprising: the combination of two artificial nucleic acid-cleaving enzymes according to claim 1.

7. A method for modifying a target nucleic acid, comprising: introducing into a cell the nucleic acid according to claim 3.

8. A method for modifying a target nucleic acid, comprising: introducing into a cell the vector according to claim 4.

9. A kit for modifying a target nucleic acid, comprising: the nucleic acid according to claim 3.

10. A kit for modifying a target nucleic acid, comprising: the vector according to claim 4.

* * * * *

SEQUENCE LISTING

<160> NUMBER OF SEQ ID NOS: 147

<210> SEQ ID NO 1
<211> LENGTH: 585
<212> TYPE: PRT
<213> ORGANISM: Bacillus sp. SGD-V-76

<400> SEQUENCE: 1

Met Ala Thr Lys Arg Val Val Arg Thr Phe Gly Trp Ile Gln Asn Pro
1               5                   10                  15

Gly Lys Phe Glu Asn Leu Lys Arg Thr Val Gln Val Phe Asp Glu Asn
            20                  25                  30

Ser Lys Val Tyr Lys Glu Val Arg Asp Ile Lys Ile Pro Asn Leu Val
        35                  40                  45

Lys Asp Lys Asp Val Arg Thr Thr Leu Ile Ala Ala Met Asn Arg Leu
    50                  55                  60

```
Glu Asn Tyr Tyr Ser Tyr Lys Glu Leu Val Gly Thr Gly Thr Ser Val
 65                  70                  75                  80

Arg Ala Gln Ala Pro Cys Asp Ala Ile Ile Gln Ala Ala Ile Gln Asp
                 85                  90                  95

Gln Gly Asn Lys Lys Gly Tyr Ile Asp Asn Trp Ser Ser Asp Gly Phe
            100                 105                 110

Val Arg Trp Ala His Ala Leu Gly Phe Leu Glu Tyr Asn Ser Asp Lys
        115                 120                 125

Asp Ser Phe Tyr Leu Thr Asp Ile Gly Leu Glu Tyr Ser Arg Ser Thr
    130                 135                 140

Asp Asp Ser Leu Asn Glu Lys Ile Ile Leu Ile Glu Ala Leu Ser Ser
145                 150                 155                 160

Tyr Pro Pro Ala Ile Arg Ile Leu Thr Leu Leu Glu Asn Gly Glu His
                165                 170                 175

Leu Thr Lys Phe Asp Leu Gly Lys Gln Leu Gly Phe Ser Gly Glu Ser
            180                 185                 190

Gly Phe Thr Ser Leu Pro Gln Asn Leu Phe Leu Asp Ala Leu Ala Asn
        195                 200                 205

Ala Pro Ser Ser Pro Thr Ile Lys Asn Ser Ile Arg Ser Asp Trp
210                 215                 220

Glu Gly Ser Ala Asp Lys Tyr Ala Arg Met Ile Ser Gly Trp Leu Val
225                 230                 235                 240

Lys Met Gly Leu Val Ala Gln Gly Arg Lys Asn Phe Val Val Pro Thr
                245                 250                 255

Val Gly Gly Ser Thr Arg Asn Glu Tyr Ile Ser His Ala Phe Lys Ile
            260                 265                 270

Thr Lys Asp Gly Leu Asp Val Leu Arg Arg Ala Lys Gly Ala Ser Lys
        275                 280                 285

His Val Arg Val Pro Lys Arg Val Tyr Trp Glu Met Phe Ala Thr Asn
    290                 295                 300

Ile Asn Asp Arg Val Tyr Val Arg Thr Arg Ala Tyr Thr Leu Tyr
305                 310                 315                 320

Leu Leu Met Arg Ser Asn Thr Ala Leu Asn Thr Val Gln Leu Gln Val
                325                 330                 335

Lys Leu Lys Ala Leu Gly Phe Glu Glu Leu Glu Glu Thr Ile Glu Asn
            340                 345                 350

Asp Val Lys Gly Leu Ile Asn Ser Gly Ile Phe Ile Asn Val Thr Asn
        355                 360                 365

Lys Gly Tyr His Phe Lys Asp Thr Ile Lys Pro Phe Glu Ile Pro Glu
    370                 375                 380

Phe Gly Val Thr Glu Pro Leu Val Lys Gly Glu Met Glu Lys Lys
385                 390                 395                 400

Ser Asp Leu Arg His Lys Leu Lys His Val Pro His Glu Tyr Ile Glu
                405                 410                 415

Leu Ile Glu Ile Ala Gln Asp Ser Lys Gln Asn Arg Leu Phe Glu Phe
            420                 425                 430

Lys Val Val Glu Phe Leu Lys Glu Val Tyr Asp Tyr Asn Gly Lys His
        435                 440                 445

Leu Gly Gly Ser Arg Lys Pro Asp Gly Ala Leu Tyr Thr Asn Gly Leu
    450                 455                 460

Lys Thr Asp Tyr Gly Ile Ile Leu Asp Thr Lys Ala Tyr Lys Asp Gly
465                 470                 475                 480

Tyr Ser Leu Pro Ile Ser Gln Ala Asp Glu Met Gln Arg Tyr Val Asp
```

```
                    485              490              495
Glu Asn Asn Arg Asn Ala Ile Ile Asn Pro Asn Glu Trp Trp Lys
            500              505              510

Val Tyr Pro Asn Ser Ile Leu Asp Phe Lys Phe Leu Phe Val Ser Gly
            515              520              525

Phe Phe Lys Gly Asp Tyr Lys Lys Gln Leu Ala Arg Val Ser Asn Leu
            530              535              540

Thr Lys Arg Lys Gly Ala Val Leu Ser Val Glu Gln Leu Leu Leu Gly
545              550              555              560

Gly Glu Lys Ile Lys Asp Gly Ser Leu Thr Leu Glu Asp Val Gly Asp
                565              570              575

Lys Phe Asn Asn Asp Glu Ile Ile Phe
            580              585
```

<210> SEQ ID NO 2
<211> LENGTH: 1758
<212> TYPE: DNA
<213> ORGANISM: Bacillus sp. SGD-V-76

<400> SEQUENCE: 2

```
atggcaacaa aacgagtggt tcgtacattt ggttggatac agaatccagg taaattcgag    60
aacctaaaac gaacagtcca agtattcgat gaaaactcaa agtatataa agaggttagg    120
gatataaaga ttccaaatct agtgaaagat aaagatgtaa gaactacttt aatagctgct    180
atgaatcgat tagaaaatta ttactcatat aaagagttgg ttggtacagg tacttcagtt    240
agagctcaag cgccttgtga tgccattatt caagcagcga ttcaagacca aggtaataaa    300
aaaggataca ttgataattg gtcttctgat ggattcgttc gttgggcaca tgcattgggg    360
tttcttgagt ataactcaga taaggactca ttttacctaa ctgatattgg attggaatat    420
tctcgttcta cagatgattc actaaatgaa aaaatcatac ttattgaagc attgtcatca    480
tatccaccag caattcgaat attgacatta cttgaaaatg gtgagcattt aacaaaattc    540
gacctaggta acagttaggc tttagtggaa gagagtggtt ttacttcatt accacaaaac    600
ttatttttag atgcgttagc aaatgcacct tcatcaccac caacaattaa gaattctatt    660
cgttctgatt gggaaggttc tgcggataaa tatgcacgga tgatttcagg ctggcttgta    720
aagatggggc ttgttgcaca aggtcgtaaa aattttgttg taccaacggt aggtggttct    780
actcgaaatg agtatatatc tcatgctttt aaaattacaa agatggtct tgatgtgtta    840
aggagagcaa aaggtgccag taaacatgta cgagtaccaa agcgtgtata ctgggagatg    900
ttcgctacca acattaacga tagagtgtat gtaagaacaa gacgggctta tacactttac    960
ttgttaatga agtaacac tgctctaaat actgttcaac ttcaagtgaa attaaaagct   1020
ttgggctttg aagaattgga agaaacaatt gagaatgatg taaaaggttt aattaactct   1080
ggaattttta tcaatgtgac gaataaaggt tatcatttta agatacaat taaaccattc   1140
gaaattcctg aatttggcgt aacagaacca ttagtaaagg gggaaatgga agaagaaaa   1200
tccgatttgc gtcataagtt aaaacacgta ccgcatgaat atattgaact aatagaaatt   1260
gcacaggatt caaagcaaaa tcgtttgttc gaatttaaag tagttgagtt tttgaaagaa   1320
gtttatgatt ataatggaaa gcacctaggg gggagtcgaa aaccagatgg cgcactatat   1380
accaatggtt taaaaacaga ttatggaata attttagata ccaaagctta caaagatggt   1440
tatagtttac caatctccca ggcagatgaa atgcagcgtt atgtcgatga aaataataat   1500
agaaatgcta ttattaatcc taacgaatgg tggaaagtgt atcctaattc tatccttggac   1560
```

-continued

```
tttaaattct tattcgtaag tggtttttt aaaggtgact ataaaaaaca attagctcgt    1620
gtaagtaatc ttacaaagcg taaaggtgct gtcctaagcg tagagcaact attattggga    1680
ggggaaaaaa ttaaagatgg tagtttaaca ttagaagatg ttggtgacaa attcaataat    1740
gatgaaatta ttttctaa                                                  1758

<210> SEQ ID NO 3
<211> LENGTH: 579
<212> TYPE: PRT
<213> ORGANISM: Clostridium botulinum

<400> SEQUENCE: 3

Val Glu Ser Leu Arg Leu Ser Asp Ile Thr Ile Arg Thr Phe Gly Trp
1               5                   10                  15

Ile Gln Asn Pro Ser Asp Phe Ser Lys Leu Lys Ile Val Gln Leu
            20                  25                  30

Phe Asp His Thr Ser Ser Ile His Val Asp Leu Lys Glu Asn Arg Ile
            35                  40                  45

Pro Arg Leu Val Glu Lys Asp Asp Gly Arg Asp Arg Phe Ile Glu Ile
        50                  55                  60

Leu Asn Arg Ile Pro Leu Lys Ile Lys Tyr Ile Asp Leu Val Gly Thr
65                  70                  75                  80

Ser Phe Lys Pro Arg Ser Ser Gly Arg Cys Asn Gly Ile Ala Gln Ala
                85                  90                  95

Met Ile Glu Gly Gln Gly Lys Ser Phe Thr Asp Asn Trp Thr Ala Asp
            100                 105                 110

Gly Phe Ile Arg Trp Ala His Ala Leu Gly Phe Ile Gln Tyr Asp Tyr
        115                 120                 125

Leu Glu Asp Glu Phe Ser Ile Thr Gln Ala Gly Phe Asp Phe Ser Arg
    130                 135                 140

Ser Ile Asn Asp Ser Glu Gly Glu Asn Glu Ile Leu Ile Glu Ala Met
145                 150                 155                 160

Leu Ser Tyr Pro Pro Ala Val Arg Val Leu Asp Leu Leu Ser Leu Gly
                165                 170                 175

Glu His Leu Thr Lys Phe Asp Ile Gly Lys Asn Leu Gly Phe Asn Gly
            180                 185                 190

Glu Ser Gly Phe Thr Ser Leu Pro Leu Asn Ile Met Leu Gln Thr Leu
        195                 200                 205

Ala Asp Asn Asp Leu Val Ser Glu Lys Thr Lys Ile Arg Gln Asp Trp
    210                 215                 220

Glu Gly Ser Ser Asp Lys Tyr Ser Arg Met Ile Ala Gly Trp Leu Ser
225                 230                 235                 240

Lys Leu Gly Leu Val Lys Lys Gly Lys Lys Tyr Phe Asp Val Asn Ile
                245                 250                 255

Gly Gly Ile Ile His Arg Glu Tyr Ile Ser His Ala Tyr Lys Ile Thr
            260                 265                 270

Gly Glu Gly Leu Lys Gln Leu Arg Arg Ala Lys Gly Thr Thr Ser Ala
        275                 280                 285

Arg Arg Ile Glu Lys Arg Val Cys Trp Glu Met Phe Ala Thr Lys Asn
    290                 295                 300

Leu Asp Arg Thr Tyr Ile Arg Thr Arg Ala Tyr Ile Leu Lys Phe
305                 310                 315                 320

Leu Glu Val Ser Ser Ser Leu Ile Thr Ile Glu Gln Ile Lys Thr Lys
                325                 330                 335
```

Leu Leu Glu Lys Gly Tyr Asp Glu Thr Val Glu Thr Ile Lys Ser Asp
            340                 345                 350

Ile Lys Gly Leu Ile Asn Ile Gly Leu Asn Ile Gln Glu Thr Thr Arg
        355                 360                 365

Gly Tyr Ser Leu Lys Asp Ser Ile Asn Asp Phe Met Ile Pro Val Thr
    370                 375                 380

Asp Leu Asn Gln Ile Val Lys Ser Ser Ile Glu Met Ser Lys Ala Asn
385                 390                 395                 400

Met Arg Asp Asn Leu Gln Met Leu Pro His Asp Tyr Ile Glu Leu Ile
                405                 410                 415

Glu Ile Ser Gln Asp Pro Tyr Gln Asn Arg Ile Phe Glu Met Lys Val
            420                 425                 430

Met Asp Leu Phe Ile Asn Glu Tyr Gly Phe Ser Gly Ser His Leu Gly
        435                 440                 445

Gly Ser Arg Lys Pro Asp Gly Ala Met Tyr Ala His Gly Phe Gly Val
    450                 455                 460

Ile Val Asp Thr Lys Ala Tyr Lys Asp Gly Tyr Asn Leu Pro Ile Ser
465                 470                 475                 480

Gln Ala Asp Glu Met Glu Arg Tyr Val Arg Glu Asn Ile Asp Arg Asn
                485                 490                 495

Glu His Val Asn Ser Asn Arg Trp Trp Asn Ile Phe Pro Glu Asp Thr
            500                 505                 510

Asn Glu Tyr Lys Phe Leu Phe Val Ser Gly Phe Phe Lys Gly Asn Phe
        515                 520                 525

Glu Lys Gln Leu Glu Arg Ile Ser Ile Asp Thr Gly Val Gln Gly Gly
    530                 535                 540

Ala Leu Ser Val Glu His Leu Leu Leu Gly Ala Glu Tyr Ile Lys Arg
545                 550                 555                 560

Gly Ile Leu Thr Leu Tyr Asp Phe Lys Asn Ser Phe Leu Asn Lys Glu
                565                 570                 575

Ile Gln Phe

<210> SEQ ID NO 4
<211> LENGTH: 1740
<212> TYPE: DNA
<213> ORGANISM: Clostridium botulinum

<400> SEQUENCE: 4
gtggaatcat taagattatc agacataaca attagaacat ttgggtggat tcagaatcct      60
agtgatttta gtaaattaaa aaaaatagtt cagttatttg atcatacatc atctattcat     120
gtggatttga agaaaaccg cataccacgg ttagtggaga agatgacgg acgtgatagg      180 tttattgaga tattaaatcg gattccgtta aagataaagt atattgattt agtaggaaca     240
tcatttaaac ctagaagtag tggtagatgt aatggaattg ctcaagcaat gattgaaggt     300
caaggtaaga gttttactga taattggaca gctgatgggt ttattaggtg ggctcatgca     360
cttggcttta tacaatatga ttatttagaa gatgagtttt caataacaca agcaggcttt     420 gattttcaa ggtcaatcaa tgatagtgaa ggggaaaatg aaatattaat agaggcaatg     480
ttgtcttatc cacctgcagt tagagtttta gatttactt ctttaggaga gcatcttaca     540
aaatttgata ttggaaaaaa tctgggcttc aatggcgaat caggatttac atctttacct     600
ttaaatatca tgcttcaaac attagcagac aatgatttag taagtgaaaa gactaaaatt     660
cgtcaggatt gggaaggttc ttctgataag tattcacgaa tgatagccgg ctggttatcg     720

```
aaacttggtt tggttaaaaa gggaaaaaag tattttgatg taaatattgg aggaataatt      780
catagagaat atatctctca tgcatataaa attactggag aaggtttaaa acaactccgt      840
agggctaaag gaactacaag tgcaaggcgt atagaaaaac gggtttgctg ggaaatgttc      900
gccacaaaga atctagatag gacatatatt cgtacaagaa gagcttatat tttaaagttt     960
ttagaagttt caagcagctt aattactatt gagcaaatta agactaagtt attggaaaaa    1020
ggttatgacg aaacagtaga aactattaaa tctgatatta aggggttaat taacattggt    1080
ttaaatattc aagaaaccac tcgaggttat tcattaaagg attcaattaa tgactttatg    1140
attccagtaa ccgacttaaa tcaaattgtt aaaagtagta tagagatgtc taaagctaac    1200
atgagagaca atcttcagat gttgcctcat gattatattg agctaattga aatatcacaa    1260
gatccatatc aaaatagaat atttgaaatg aaagttatgg atttatttat taatgagtat    1320
ggtttcagtg gttcgcactt aggtggaagt aggaaacctg atggtgctat gtatgcacat    1380
ggttttggtg ttattgttga tacaaaagca tataaagatg ggtacaatct tcctataagt    1440
caagctgatg aaatggaacg atatgtaagg gaaaatattg atagaaatga acatgtgaac    1500
tcaaatagat ggtggaatat atttcccgaa gatacaaatg aatataagtt tttattcgta    1560
agtggttcct ttaaaggaaa ttttgagaaa caattagaaa ggataagtat agatactggt    1620
gtacaaggag gggctttaag tgttgaacat ttattattag gtgctgagta cataaagagg    1680
ggtattctta ctttatatga ttttaagaat agcttttaa ataaggaaat tcaattttaa    1740
```

<210> SEQ ID NO 5
<211> LENGTH: 587
<212> TYPE: PRT
<213> ORGANISM: Clostridium sp. 7_2_43FAA

<400> SEQUENCE: 5

```
Met Ile Asn Ile Ile Asp Val Asn Asn Lys Thr Ile Arg Thr Phe Gly
1               5                   10                  15

Trp Val Gln Asn Pro Ser Asn Phe Glu Ser Leu Lys Lys Val Val Ala
            20                  25                  30

Ile Phe Asp Asn Thr Ser Lys Thr Tyr Asn Glu Leu Lys Asp Lys Lys
        35                  40                  45

Ile Lys Lys Leu Val Asp Glu Arg Asp Gly Gln Lys Glu Leu Leu Asn
    50                  55                  60

Ala Leu Asn Ala Asn Pro Leu Lys Ile Lys Tyr Cys Asn Leu Val Gly
65                  70                  75                  80

Thr Ser Phe Thr Pro Arg Ser Ser Ala Arg Cys Asn Gly Ile Val Gln
                85                  90                  95

Ala Thr Val Lys Gly Gln Arg Lys Glu Phe Ile Asp Asp Trp Ser Ser
            100                 105                 110

Asp Asn Phe Val Arg Trp Ala His Ala Leu Gly Phe Ile Lys Tyr Asn
        115                 120                 125

Tyr Asp Thr Asp Thr Phe Glu Ile Thr Asp Val Gly Arg Lys Tyr Val
    130                 135                 140

Gln Ser Glu Asp Asp Ser Asn Glu Glu Ser Thr Ile Leu Glu Glu Ala
145                 150                 155                 160

Met Leu Ser Tyr Pro Pro Val Ala Arg Val Leu Thr Leu Leu Ser Asn
                165                 170                 175

Gly Glu His Leu Thr Lys Tyr Glu Ile Gly Lys Lys Leu Gly Phe Val
            180                 185                 190
```

-continued

Gly Glu Ala Gly Phe Thr Ser Leu Pro Leu Asn Val Leu Ile Met Thr
            195                 200                 205

Leu Ala Thr Thr Asp Glu Pro Lys Glu Lys Asn Lys Ile Lys Thr Asp
210                 215                 220

Trp Asp Gly Ser Ser Asp Lys Tyr Ala Arg Met Ile Ser Gly Trp Leu
225                 230                 235                 240

Val Lys Leu Gly Leu Leu Val Gln Arg Pro Lys Leu Val Thr Val Asp
                245                 250                 255

Phe Gly Gly Glu Leu Tyr Ser Glu Thr Ile Gly His Ala Tyr Met Ile
                260                 265                 270

Thr Asp Arg Gly Leu Lys Ala Val Arg Arg Leu Leu Gly Ile Asn Lys
            275                 280                 285

Val Ala Arg Val Ser Lys Asn Val Phe Trp Glu Met Leu Ala Thr Lys
290                 295                 300

Gly Ile Asp Lys Asn Tyr Ile Arg Thr Arg Arg Ala Tyr Ile Leu Lys
305                 310                 315                 320

Ile Leu Ile Glu Ser Asn Lys Val Leu Thr Leu Glu Asp Ile Lys Gly
                325                 330                 335

Lys Leu Lys Leu Ala Ser Ile Asn Glu Ser Ile Asn Thr Ile Lys Asp
            340                 345                 350

Asp Ile Asn Gly Leu Ile Asn Thr Gly Ile Asn Ile Lys Ser Glu Thr
            355                 360                 365

Thr Gly Tyr Lys Ile Tyr Asp Ser Ile Asn Asp Phe Ile Ile Pro Lys
            370                 375                 380

Thr Gly Asp Thr Glu Gly Ile Lys Ser Asn Ile Ser Leu Leu Lys Asp
385                 390                 395                 400

Glu Leu Arg Gly Gln Ile Ser His Ile Ser His Glu Tyr Leu Ser Leu
                405                 410                 415

Ile Asp Leu Ala Phe Asp Ser Lys Gln Asn Arg Leu Phe Glu Met Lys
            420                 425                 430

Val Leu Glu Leu Leu Val Asn Glu Tyr Gly Phe Lys Gly Arg His Leu
            435                 440                 445

Gly Gly Ser Arg Lys Pro Asp Gly Ile Val Tyr Ser Thr Thr Leu Glu
450                 455                 460

Asp Asn Phe Gly Ile Ile Val Asp Thr Lys Ala Tyr Ser Glu Gly Tyr
465                 470                 475                 480

Ser Leu Pro Ile Ser Gln Ala Asp Glu Met Glu Arg Tyr Val Arg Glu
                485                 490                 495

Asn Ser Asn Arg Asp Glu Glu Val Asn Pro Asn Lys Trp Trp Glu Asn
            500                 505                 510

Phe Ser Glu Glu Val Lys Lys Tyr Tyr Phe Val Phe Ile Ser Gly Ser
            515                 520                 525

Phe Lys Gly Lys Phe Glu Glu Gln Leu Arg Arg Leu Ser Met Thr Thr
530                 535                 540

Gly Val Asn Gly Ser Ala Val Asn Val Val Asn Leu Leu Leu Gly Ala
545                 550                 555                 560

Glu Lys Ile Arg Ser Gly Glu Met Thr Ile Glu Glu Leu Glu Arg Ala
                565                 570                 575

Met Phe Asn Asn Ser Glu Phe Ile Leu Lys Tyr
            580                 585

<210> SEQ ID NO 6
<211> LENGTH: 1764
<212> TYPE: DNA

<213> ORGANISM: Clostridium sp. 7_2_43FAA

<400> SEQUENCE: 6

| | |
|---|---:|
| atgattaaca taattgacgt aaataataaa actattagaa cttttggatg ggttcagaat | 60 |
| ccaagtaatt ttgaaagctt aaaaaaagtt gtagcaatat ttgataatac atcaaagaca | 120 |
| tataatgaat taaagataaa gaaaataaaa aagttagtag acgaaagaga tgggcaaaaa | 180 |
| gaactattaa atgctttaaa tgctaatcct ttaaagataa agtattgtaa tttagtaggg | 240 |
| acatctttta ctccacgaag ttctgcaaga tgtaatggaa tagtacaagc cacagtaaaa | 300 |
| ggacaaagaa aagagttcat agatgattgg tcatctgata actttgtaag atgggcacat | 360 |
| gctttaggct ttattaaata taattatgat acagatacat ttgagataac cgatgtagga | 420 |
| agaaagtatg tacagagtga agatgatagc aatgaggaaa gtacaatttt agaagaagca | 480 |
| atgttatcat atccaccagt agcaagggtt ttgacattgc tttccaatgg agaacattta | 540 |
| acaaaatatg aaataggtaa gaattagga tttgtagggg aagctggttt tactagtttg | 600 |
| ccattgaatg tattaattat gacattagct actacagatg agccgaagga aaaaaataaa | 660 |
| attaaaacag actgggatgg gtcttctgat aaatatgcaa gaatgatttc tggttggtta | 720 |
| gtaaaattag gattattggt acaaagacct aaattggtta ctgtagattt tggtggtgaa | 780 |
| ttatatagcg aaacaatagg acatgcttat atgattacgg ataggggatt aaaagctgtt | 840 |
| agaagattat taggaataaa taagttgcg agggtttcaa aaaatgtttt ttgggaaatg | 900 |
| cttgcaacaa aaggaataga taaaaattat ataagaactc gaagagcata tattttaaaa | 960 |
| atattaattg aatctaataa ggtattaact ttagaggata taaaaggaaa gttgaaatta | 1020 |
| gcgagtatta atgaatctat taatactatt aaagacgata ttaatggatt aattaataca | 1080 |
| ggtataaata ttaagagtga aacaactggg tataaaatat atgattcaat taatgatttt | 1140 |
| attataccta aaacaggaga tacagaggga ataagagta atattagctt attaaaagat | 1200 |
| gaattaagag ggcaaataag tcatatttca catgagtatt tatcattaat agatttagca | 1260 |
| tttgatagta agcaaaatag gttatttgaa atgaaagttt tagagttgtt agttaatgag | 1320 |
| tatggattta aggaaggca tctaggtgga agtagaaaac ctgatggtat agtttattca | 1380 |
| acaactttag aagataattt tggaataata gtagatacta agcttattc agaagggtat | 1440 |
| agcttaccta aagtcaagc tgatgaaatg gagagatatg ttagagaaaa ctctaataga | 1500 |
| gatgaggaag taaaccctaa taagtggtgg gaaaactttt cagaagaagt caaaaagtat | 1560 |
| tattttgtat tcatatcagg ttccttaag ggcaaatttg aagaacaatt aagaagattg | 1620 |
| agcatgacta ctggggttaa cggttcagct gttaatgtag taaatttatt actaggagct | 1680 |
| gaaaaaataa ggtctggaga atgactatt gaagaattag agagagctat gtttaataac | 1740 |
| tcggaattta tattgaagta ttaa | 1764 |

<210> SEQ ID NO 7
<211> LENGTH: 589
<212> TYPE: PRT
<213> ORGANISM: Clostridiales bacterium KA00134

<400> SEQUENCE: 7

Met Ala Glu Arg Thr Leu Gly Trp Ile Gln Asn Pro Ser Ser Phe Glu
1               5                   10                  15

Asn Leu Lys Asn Val Val Ser Val Phe Asp Lys Asn Thr Asp Ile Tyr
            20                  25                  30

Lys Glu Ile Leu Asn Thr Lys Leu Pro Lys Leu Val Lys Asp Leu Asp

```
                    35                  40                  45
Leu Gln Asn Lys Leu Ile Ser Glu Met Lys Lys Asp Pro Leu Glu Met
 50                  55                  60

Asp Tyr Val Leu Leu Lys Gly His Gly Ile Lys Ser Gly Gln Lys Arg
 65                  70                  75                  80

Ser Asp Ala Ala Cys Ser Gly Ile Val Gln Ala Ile Thr Thr Gln
                 85                  90                  95

Gly Gly Arg Ala Tyr Thr Asp Asp Trp Thr Ala Asp Gly Phe Leu Arg
                100                 105                 110

Trp Gly Ile Ser Ile Gly Leu Leu Asp Tyr Asp Thr Glu Asn Asp Thr
                115                 120                 125

Val Ser Ile Thr Lys Leu Gly Glu Lys Phe Val Lys Ser Asn Ser Glu
        130                 135                 140

Asp Ser Asp Lys Glu Ile Leu Ile Ser Ala Phe Leu Ser Tyr Pro Pro
145                 150                 155                 160

Ala Val Arg Ile Leu Thr Leu Leu Glu Ser Gly Asp His Leu Thr Lys
                165                 170                 175

Phe Glu Leu Gly Lys Gln Leu Gly Gly Leu Gly Glu Ala Gly Phe Thr
                180                 185                 190

Ser Ile Pro Gln Asp Leu Tyr Ile Gln Ala Ile Glu Leu Ala Ser Glu
                195                 200                 205

Thr Asp Lys Ala Ser Ile Arg Ser Asn Thr Glu Gly Ser Ala Asp Lys
        210                 215                 220

Tyr Ala Arg Met Ile Ser Gly Trp Leu Ser Lys Val Gly Leu Val Gln
225                 230                 235                 240

Arg Val Glu Lys Glu Val Ser Thr Lys Ile Gly Asn Val Glu Tyr Met
                245                 250                 255

Val Asn Ile Gly His Ser Phe Arg Ile Thr Leu Asn Gly Ile Lys Glu
                260                 265                 270

Leu Lys Arg Ala Arg Gly Leu Ser Ser Tyr Pro Lys Thr Asp Lys Ile
        275                 280                 285

Val Tyr Trp Gln Met Leu Ala Thr Lys Gly Lys Asp Arg Asp Tyr Ile
290                 295                 300

Arg Asn Arg Arg Gly Tyr Ile Ile Lys Ala Ile Asn Asn Arg Glu Arg
305                 310                 315                 320

Asn Leu Glu Gly Ile Lys Ala Tyr Leu Met Glu Asn Asn Ile Asp Glu
                325                 330                 335

Ser Ile Thr Thr Ile Glu Asp Glu Leu Lys Val Leu Lys Ala Met Gly
                340                 345                 350

Leu Ser Leu Lys His Ser Arg Asn Gly Tyr Val Ile Asp Asp Asn Ile
        355                 360                 365

Ile Lys Leu Glu Ile Pro Arg Thr Lys Ile Ser Lys Thr Asn Ile Leu
        370                 375                 380

Glu Leu Lys Asp Lys Val Arg Asp Lys Leu Lys Tyr Val Asp His Arg
385                 390                 395                 400

Tyr Leu Ala Leu Ile Asp Leu Ala Tyr Asp Gly Thr Ala Asn Arg Asp
                405                 410                 415

Phe Glu Ile Gln Thr Ile Asp Leu Leu Ile Asn Glu Leu Lys Phe Lys
                420                 425                 430

Gly Val Arg Leu Gly Glu Ser Arg Lys Pro Asp Gly Ile Ile Ser Tyr
        435                 440                 445

Asn Ile Asn Gly Val Ile Ile Asp Asn Lys Ala Tyr Ser Thr Gly Tyr
        450                 455                 460
```

```
Asn Leu Pro Ile Asn Gln Ala Asp Glu Met Ile Arg Tyr Ile Glu Glu
465                 470                 475                 480

Asn Gln Thr Arg Asp Glu Lys Ile Asn Ser Asn Lys Trp Trp Glu Ser
            485                 490                 495

Phe Asp Glu Lys Val Lys Asp Phe Asn Tyr Leu Phe Val Ser Ser Phe
            500                 505                 510

Phe Lys Gly Asn Phe Lys Asn Asn Leu Lys His Ile Ala Asn Arg Thr
            515                 520                 525

Gly Val Asn Gly Gly Ala Ile Asn Val Glu Asn Leu Leu Tyr Phe Ala
            530                 535                 540

Glu Glu Leu Lys Ala Gly Arg Ile Ser Tyr Leu Asp Ser Phe Lys Met
545                 550                 555                 560

Tyr Asn Asn Asp Glu Ile Tyr Leu Gly Asp Ile Ser Asp Tyr Ser Tyr
                565                 570                 575

Val Lys Phe Ala Ala Glu Glu Glu Gly Glu Tyr Leu Thr
            580                 585
```

<210> SEQ ID NO 8
<211> LENGTH: 1770
<212> TYPE: DNA
<213> ORGANISM: Clostridiales bacterium KA00134

<400> SEQUENCE: 8

```
atggcagaaa gaacattggg ttggatacaa atccatcaa gttttgaaaa tttaaaaaat       60
gtagtttctg ttttgataa aaatactgat atatataagg aaatattaaa tactaaactt      120
cctaaattag taaagatttt agatttacaa ataaactca tttcagaaat gaaaaaagat      180
ccacttgaaa tggactatgt tttattaaaa ggtcatggta aaatcagg tcagaaaaga       240
tccgatgcag cgtgtagtgg tattgttcaa gctgccatta acacaagg cggtagggct       300
tatacagacg attggactgc tgatggattt taagatggg gaatatccat aggacttta       360
gattatgata cagaaaatga tacagtttct ataacaaaac taggagaaaa gtttgtaaaa      420
tctaattctg aagattcaga taagaaaata ctaatttcag ccttttttgtc atacccacca    480
gccgtaagaa ttttaacttt attggaaagt ggagaccatt taacaaaatt tgagcttggt      540
aagcaattag gtggacttgg agaagctggt tttacatcaa ttcctcaaga tttatatatt      600
caagcaatag aacttgcttc tgaaacagat aaagcaagta ttcgatcaaa cacagaggga      660
tcagctgata aatatgccag aatgatttca ggatggttat ctaaggttgg tttagttcaa      720
agagttgaaa agaagtttc aacaaaaatt ggaaatgttg aatacatggt aaatataggt      780
cattccttta gaattacttt gaatggtata aaagaactta aagagcaag gggattatct      840
tcatatccaa agactgataa aattgtttat tggcaaatgc tagcaaccaa gggtaaagat      900
agagattata ttagaaacag acgtggatat ataatcaaag ctatcaacaa cagagaaaga      960
aatttagaag gcattaaggc ttatttaatg gaaaataata ttgatgaaag tattacaact     1020
atagaagacg aactaaaagt tcttaaagca atgggtcttt cacttaaaca tagtaggaat     1080
ggctatgtaa ttgatgataa cattataaaa ttagaaatac ctagaactaa gatttctaag     1140
acaaatatac tagaattaaa ggataaagta agagataaat taaatatgt tgaccacaga     1200
tatcttgcgc taattgattt agcttatgac ggaactgcca atagagattt tgagattcaa     1260
acaatagacc ttttaattaa tgaacttaag tttaaagggg ttcgtctagg agaaaagcaga    1320
aaaccagatg gaattatatc ttataatatt aatggcgtaa ttatagataa caaggcttat    1380
```

```
tctacgggtt ataatctacc aattaatcaa gcagatgaaa tgattagata tatcgaagaa    1440
aatcaaacta gagatgaaaa aataaattca aataaatggt gggaaagctt tgatgaaaaa    1500
gttaaggatt tcaactattt atttgtatca tctttcttta agggaaactt taagaataat    1560
ttgaaacata tagccaatag aactggtgta aatggtggag ctattaatgt agaaaattta    1620
ttatattttg cagaagaatt aaaagctgga agaatatctt atcttgactc atttaaaatg    1680
tataacaatg atgaaatata tttaggagat attagtgact atagttatgt taaatttgct    1740
gcagaagaag aaggcgaata tttaacataa                                    1770
```

<210> SEQ ID NO 9  
<211> LENGTH: 38  
<212> TYPE: DNA  
<213> ORGANISM: Artificial  
<220> FEATURE:  
<223> OTHER INFORMATION: ND1 substitution forward primer

<400> SEQUENCE: 9

```
gatgagatca tcttctaagg gcccttcgaa ggtaagcc                              38
```

<210> SEQ ID NO 10  
<211> LENGTH: 34  
<212> TYPE: DNA  
<213> ORGANISM: Artificial  
<220> FEATURE:  
<223> OTHER INFORMATION: ND1 substitution reverse primer

<400> SEQUENCE: 10

```
ctctcccttt actaaagctc ttgccgcagc accc                                  34
```

<210> SEQ ID NO 11  
<211> LENGTH: 38  
<212> TYPE: DNA  
<213> ORGANISM: Artificial  
<220> FEATURE:  
<223> OTHER INFORMATION: ND2 substitution forward primer

<400> SEQUENCE: 11

```
aaggagattc agttctaagg gcccttcgaa ggtaagcc                              38
```

<210> SEQ ID NO 12  
<211> LENGTH: 34  
<212> TYPE: DNA  
<213> ORGANISM: Artificial  
<220> FEATURE:  
<223> OTHER INFORMATION: ND2 substitution reverse primer

<400> SEQUENCE: 12

```
actactttta acaatagctc ttgccgcagc accc                                  34
```

<210> SEQ ID NO 13  
<211> LENGTH: 38  
<212> TYPE: DNA  
<213> ORGANISM: Artificial  
<220> FEATURE:  
<223> OTHER INFORMATION: ND3 substitution forward primer

<400> SEQUENCE: 13

```
aacagcgagt tcatataagg gcccttcgaa ggtaagcc                              38
```

<210> SEQ ID NO 14  
<211> LENGTH: 34  
<212> TYPE: DNA  
<213> ORGANISM: Artificial

```
<220> FEATURE:
<223> OTHER INFORMATION: ND3 substitution reverse primer

<400> SEQUENCE: 14
gttactcttg attccagctc ttgccgcagc accc                              34

<210> SEQ ID NO 15
<211> LENGTH: 38
<212> TYPE: DNA
<213> ORGANISM: Artificial
<220> FEATURE:
<223> OTHER INFORMATION: ND4 substitution forward primer

<400> SEQUENCE: 15
gatgaaatct acctgtaagg gcccttcgaa ggtaagcc                          38

<210> SEQ ID NO 16
<211> LENGTH: 34
<212> TYPE: DNA
<213> ORGANISM: Artificial
<220> FEATURE:
<223> OTHER INFORMATION: ND4 substitution reverse primer

<400> SEQUENCE: 16
gtttgtcttg gagatagctc ttgccgcagc accc                              34

<210> SEQ ID NO 17
<211> LENGTH: 49
<212> TYPE: DNA
<213> ORGANISM: Artificial
<220> FEATURE:
<223> OTHER INFORMATION: forward primer for linker alteration,
      ZFN-FokI-GS-F

<400> SEQUENCE: 17
agaacacacg gatccctagt caaaagtgaa ctggaggaga agaaatctg               49

<210> SEQ ID NO 18
<211> LENGTH: 34
<212> TYPE: DNA
<213> ORGANISM: Artificial
<220> FEATURE:
<223> OTHER INFORMATION: reverse primer for linker alteration,
      ZFN-GS-inverse-R

<400> SEQUENCE: 18
ggatccgtgt gttctctggt gtctcacgag attg                              34

<210> SEQ ID NO 19
<211> LENGTH: 48
<212> TYPE: DNA
<213> ORGANISM: Artificial
<220> FEATURE:
<223> OTHER INFORMATION: forward primer for linker alteration,
      ZFN-ND1-GS-F

<400> SEQUENCE: 19
agaacacacg gatccttagt aaagggagag atggagaaga aaaagagc                48

<210> SEQ ID NO 20
<211> LENGTH: 34
<212> TYPE: DNA
<213> ORGANISM: Artificial
<220> FEATURE:
<223> OTHER INFORMATION: reverse primer for linker alteration,
      ZFN-GS-inverse-R
```

-continued

<400> SEQUENCE: 20
ggatccgtgt gttctctggt gtctcacgag attg     34

<210> SEQ ID NO 21
<211> LENGTH: 47
<212> TYPE: DNA
<213> ORGANISM: Artificial
<220> FEATURE:
<223> OTHER INFORMATION: forward primer for linker alteration,
     ZFN-ND2-GS-F

<400> SEQUENCE: 21
agaacacacg gatccattgt taaaagtagt attgagatgt ccaaggc     47

<210> SEQ ID NO 22
<211> LENGTH: 34
<212> TYPE: DNA
<213> ORGANISM: Artificial
<220> FEATURE:
<223> OTHER INFORMATION: reverse primer for linker alteration,
     ZFN-GS-inverse-R

<400> SEQUENCE: 22
ggatccgtgt gttctctggt gtctcacgag attg     34

<210> SEQ ID NO 23
<211> LENGTH: 51
<212> TYPE: DNA
<213> ORGANISM: Artificial
<220> FEATURE:
<223> OTHER INFORMATION: forward primer for linker alteration,
     ZFN-FokI-RPGEKP-F

<400> SEQUENCE: 23
gacccgggga gaagcccta gtcaaaagtg aactggagga gaagaaatct g     51

<210> SEQ ID NO 24
<211> LENGTH: 44
<212> TYPE: DNA
<213> ORGANISM: Artificial
<220> FEATURE:
<223> OTHER INFORMATION: reverse primer for linker alteration,
     ZFN-RPGEKP-R

<400> SEQUENCE: 24
gcttctcccc gggtctgtgt gttctctggt gtctcacgag attg     44

<210> SEQ ID NO 25
<211> LENGTH: 50
<212> TYPE: DNA
<213> ORGANISM: Artificial
<220> FEATURE:
<223> OTHER INFORMATION: forward primer for linker alteration,
     ZFN-ND1-RPGEKP-F

<400> SEQUENCE: 25
gacccgggga gaagcccta gtaaagggag agatggagaa gaaaagagc     50

<210> SEQ ID NO 26
<211> LENGTH: 44
<212> TYPE: DNA
<213> ORGANISM: Artificial
<220> FEATURE:
<223> OTHER INFORMATION: reverse primer for linker alteration,
     ZFN-RPGEKP-R

<400> SEQUENCE: 26
gcttctcccc gggtctgtgt gttctctggt gtctcacgag attg        44

<210> SEQ ID NO 27
<211> LENGTH: 49
<212> TYPE: DNA
<213> ORGANISM: Artificial
<220> FEATURE:
<223> OTHER INFORMATION: forward primer for linker alteration,
      ZFN-ND2-RPGEKP-F

<400> SEQUENCE: 27
gacccgggga gaagcccatt gttaaaagta gtattgagat gtccaaggc        49

<210> SEQ ID NO 28
<211> LENGTH: 44
<212> TYPE: DNA
<213> ORGANISM: Artificial
<220> FEATURE:
<223> OTHER INFORMATION: reverse primer for linker alteration,
      ZFN-RPGEKP-R

<400> SEQUENCE: 28
gcttctcccc gggtctgtgt gttctctggt gtctcacgag attg        44

<210> SEQ ID NO 29
<211> LENGTH: 55
<212> TYPE: DNA
<213> ORGANISM: Artificial
<220> FEATURE:
<223> OTHER INFORMATION: forward primer for linker alteration,
      ZFN-FokI-TGPGAAARA-F

<400> SEQUENCE: 29
cccggggctg cggcaagagc tctagtcaaa agtgaactgg aggagaagaa atctg        55

<210> SEQ ID NO 30
<211> LENGTH: 49
<212> TYPE: DNA
<213> ORGANISM: Artificial
<220> FEATURE:
<223> OTHER INFORMATION: reverse primer for linker alteration,
      ZFN-FokI-TGPGAAARA-R

<400> SEQUENCE: 30
tgccgcagcc ccgggacccg tgtgtgttct ctggtgtctc acgagattg        49

<210> SEQ ID NO 31
<211> LENGTH: 54
<212> TYPE: DNA
<213> ORGANISM: Artificial
<220> FEATURE:
<223> OTHER INFORMATION: forward primer for linker alteration,
      ZFN-ND1-TGPGAAARA-F

<400> SEQUENCE: 31
cccggggctg cggcaagagc tttagtaaag ggagagatgg agaagaaaaa gagc        54

<210> SEQ ID NO 32
<211> LENGTH: 49
<212> TYPE: DNA
<213> ORGANISM: Artificial
<220> FEATURE:
<223> OTHER INFORMATION: reverse primer for linker alteration,
      ZFN-FokI-TGPGAAARA-R

<400> SEQUENCE: 32

```
tgccgcagcc ccgggacccg tgtgtgttct ctggtgtctc acgagattg          49

<210> SEQ ID NO 33
<211> LENGTH: 53
<212> TYPE: DNA
<213> ORGANISM: Artificial
<220> FEATURE:
<223> OTHER INFORMATION: forward primer for linker alteration,
      ZFN-ND2-TGPGAAARA-F

<400> SEQUENCE: 33
cccggggctg cggcaagagc tattgttaaa agtagtattg agatgtccaa ggc     53

<210> SEQ ID NO 34
<211> LENGTH: 49
<212> TYPE: DNA
<213> ORGANISM: Artificial
<220> FEATURE:
<223> OTHER INFORMATION: reverse primer for linker alteration,
      ZFN-FokI-TGPGAAARA-R

<400> SEQUENCE: 34
tgccgcagcc ccgggacccg tgtgtgttct ctggtgtctc acgagattg          49

<210> SEQ ID NO 35
<211> LENGTH: 59
<212> TYPE: DNA
<213> ORGANISM: Artificial
<220> FEATURE:
<223> OTHER INFORMATION: forward primer for Sharkey mutation
      introduction in FokI-ND

<400> SEQUENCE: 35
aaggtaatgg aattttttat gaaagtttat ggatatagag gtgaacattt gggtggatc    59

<210> SEQ ID NO 36
<211> LENGTH: 57
<212> TYPE: DNA
<213> ORGANISM: Artificial
<220> FEATURE:
<223> OTHER INFORMATION: reverse primer for Sharkey mutation
      introduction in FokI-ND

<400> SEQUENCE: 36
aaattccatt accttcattt caagaattct atcctgagta ggatttctgg caatttc     57

<210> SEQ ID NO 37
<211> LENGTH: 59
<212> TYPE: DNA
<213> ORGANISM: Artificial
<220> FEATURE:
<223> OTHER INFORMATION: forward primer for Sharkey mutation
      introduction in ND1

<400> SEQUENCE: 37
ttaaggtagt ggaatttctg aaagaagtgt acgattacaa tggtgagcat ctgggcggc    59

<210> SEQ ID NO 38
<211> LENGTH: 56
<212> TYPE: DNA
<213> ORGANISM: Artificial
<220> FEATURE:
<223> OTHER INFORMATION: reverse primer for Sharkey mutation
      introduction in ND1

<400> SEQUENCE: 38
attccactac cttaaactcg aagagtctgt tctgcttggg gtcctgagca atttcg      56
```

<210> SEQ ID NO 39
<211> LENGTH: 30
<212> TYPE: DNA
<213> ORGANISM: Artificial
<220> FEATURE:
<223> OTHER INFORMATION: forward primer for Sharkey mutation
      introduction in ND2

<400> SEQUENCE: 39
tccggggagc atctgggggg tagccggaag                                    30

<210> SEQ ID NO 40
<211> LENGTH: 34
<212> TYPE: DNA
<213> ORGANISM: Artificial
<220> FEATURE:
<223> OTHER INFORMATION: reverse primer for Sharkey mutation
      introduction in ND2

<400> SEQUENCE: 40
cagatgctcc ccggagaagc catactcgtt gatg                               34

<210> SEQ ID NO 41
<211> LENGTH: 19
<212> TYPE: DNA
<213> ORGANISM: Artificial
<220> FEATURE:
<223> OTHER INFORMATION: ZFA substitution forward primer

<400> SEQUENCE: 41
acgggtgctg cggcaagag                                                19

<210> SEQ ID NO 42
<211> LENGTH: 43
<212> TYPE: DNA
<213> ORGANISM: Artificial
<220> FEATURE:
<223> OTHER INFORMATION: ZFA substitution reverse primer

<400> SEQUENCE: 42
aggtctctcg tggggtctag atttatcgtc gtcatccttg tag                     43

<210> SEQ ID NO 43
<211> LENGTH: 54
<212> TYPE: DNA
<213> ORGANISM: Artificial
<220> FEATURE:
<223> OTHER INFORMATION: forward primer for FokI-DDD mutation
      introduction

<400> SEQUENCE: 43
gaagaaaatc aaacacgaga caaacatatc aaccctaatg aatggtggaa agtc         54

<210> SEQ ID NO 44
<211> LENGTH: 50
<212> TYPE: DNA
<213> ORGANISM: Artificial
<220> FEATURE:
<223> OTHER INFORMATION: reverse primer for FokI-DDD mutation
      introduction

<400> SEQUENCE: 44
tgtttgattt tcttcgacat agtcttgcat ttcatctgct tggccaattg              50

<210> SEQ ID NO 45

```
<211> LENGTH: 49
<212> TYPE: DNA
<213> ORGANISM: Artificial
<220> FEATURE:
<223> OTHER INFORMATION: forward primer for ND1-DDD mutation
      introduction

<400> SEQUENCE: 45
cgacgaaaat aacaataggg acgcaatcat caaccctaat gagtggtgg              49

<210> SEQ ID NO 46
<211> LENGTH: 49
<212> TYPE: DNA
<213> ORGANISM: Artificial
<220> FEATURE:
<223> OTHER INFORMATION: reverse primer for ND1-DDD mutation
      introduction

<400> SEQUENCE: 46
ttgttatttt cgtcgacata gtcttgcatc tcatcggcct gagaaattg              49

<210> SEQ ID NO 47
<211> LENGTH: 49
<212> TYPE: DNA
<213> ORGANISM: Artificial
<220> FEATURE:
<223> OTHER INFORMATION: forward primer for ND2-DDD mutation
      introduction

<400> SEQUENCE: 47
tcagggagaa cattgacaga gacgagcacg tcaattctaa ccgctggtg              49

<210> SEQ ID NO 48
<211> LENGTH: 44
<212> TYPE: DNA
<213> ORGANISM: Artificial
<220> FEATURE:
<223> OTHER INFORMATION: reverse primer for ND2-DDD mutation
      introduction

<400> SEQUENCE: 48
caatgttctc cctgacgtag tcttccattt catcggcctg gctg                   44

<210> SEQ ID NO 49
<211> LENGTH: 43
<212> TYPE: DNA
<213> ORGANISM: Artificial
<220> FEATURE:
<223> OTHER INFORMATION: forward primer for FokI-RRR vector mutation
      introduction

<400> SEQUENCE: 49
ttaaatcgga tcactaattg taatggagct gttcttagtg tag                    43

<210> SEQ ID NO 50
<211> LENGTH: 34
<212> TYPE: DNA
<213> ORGANISM: Artificial
<220> FEATURE:
<223> OTHER INFORMATION: reverse primer for FokI-RRR vector mutation
      introduction

<400> SEQUENCE: 50
atttcccggg cttggccaat tgcagatta taac                               34

<210> SEQ ID NO 51
<211> LENGTH: 38
```

```
<212> TYPE: DNA
<213> ORGANISM: Artificial
<220> FEATURE:
<223> OTHER INFORMATION: forward primer for FokI-RRR insert mutation
      introduction

<400> SEQUENCE: 51
ccaagcccgg gaaatgcaac gatatgtcga agaaaatc                              38

<210> SEQ ID NO 52
<211> LENGTH: 42
<212> TYPE: DNA
<213> ORGANISM: Artificial
<220> FEATURE:
<223> OTHER INFORMATION: reverse primer for FokI-RRR insert mutation
      introduction

<400> SEQUENCE: 52
agtgatccga tttaatcgtg taagctgagc tttgtagttt cc                         42

<210> SEQ ID NO 53
<211> LENGTH: 28
<212> TYPE: DNA
<213> ORGANISM: Artificial
<220> FEATURE:
<223> OTHER INFORMATION: forward primer for ND1-RRR vector mutation
      introduction

<400> SEQUENCE: 53
gtgtccagac tgaccaagcg caagggcg                                        28

<210> SEQ ID NO 54
<211> LENGTH: 34
<212> TYPE: DNA
<213> ORGANISM: Artificial
<220> FEATURE:
<223> OTHER INFORMATION: reverse primer for ND1-RRR vector mutation
      introduction

<400> SEQUENCE: 54
catctcccgg gcctgagaaa ttgggaggct gtag                                 34

<210> SEQ ID NO 55
<211> LENGTH: 45
<212> TYPE: DNA
<213> ORGANISM: Artificial
<220> FEATURE:
<223> OTHER INFORMATION: forward primer for ND1-RRR insert mutation
      introduction

<400> SEQUENCE: 55
caggcccggg agatgcaaag atatgttgac gaaaataaca atagg                     45

<210> SEQ ID NO 56
<211> LENGTH: 34
<212> TYPE: DNA
<213> ORGANISM: Artificial
<220> FEATURE:
<223> OTHER INFORMATION: reverse primer for ND1-RRR insert mutation
      introduction

<400> SEQUENCE: 56
ggtcagtctg gacacccttg ccagctgttt cttg                                 34

<210> SEQ ID NO 57
<211> LENGTH: 28
<212> TYPE: DNA
```

```
<213> ORGANISM: Artificial
<220> FEATURE:
<223> OTHER INFORMATION: forward primer for ND2-RRR vector mutation
      introduction

<400> SEQUENCE: 57
atctcaaggg ataccggggt gcagggcg                                          28

<210> SEQ ID NO 58
<211> LENGTH: 31
<212> TYPE: DNA
<213> ORGANISM: Artificial
<220> FEATURE:
<223> OTHER INFORMATION: reverse primer for ND2-RRR vector mutation
      introduction

<400> SEQUENCE: 58
catttcccgg gcctggctga tggggagatt g                                      31

<210> SEQ ID NO 59
<211> LENGTH: 40
<212> TYPE: DNA
<213> ORGANISM: Artificial
<220> FEATURE:
<223> OTHER INFORMATION: forward primer for ND2-RRR insert mutation
      introduction

<400> SEQUENCE: 59
caggcccggg aaatggaaag gtacgtcagg gagaacattg                             40

<210> SEQ ID NO 60
<211> LENGTH: 42
<212> TYPE: DNA
<213> ORGANISM: Artificial
<220> FEATURE:
<223> OTHER INFORMATION: reverse primer for ND2-RRR insert mutation
      introduction

<400> SEQUENCE: 60
ggtatccctt gagattcttt ccaactgttt ctcaaagttt cc                          42

<210> SEQ ID NO 61
<211> LENGTH: 17
<212> TYPE: DNA
<213> ORGANISM: Artificial
<220> FEATURE:
<223> OTHER INFORMATION: M13-F primer

<400> SEQUENCE: 61
gtaaaacgac ggccagt                                                      17

<210> SEQ ID NO 62
<211> LENGTH: 24
<212> TYPE: DNA
<213> ORGANISM: Cricetulus griseus

<400> SEQUENCE: 62
accatcttcc actctgaaga tgga                                              24

<210> SEQ ID NO 63
<211> LENGTH: 24
<212> TYPE: DNA
<213> ORGANISM: Cricetulus griseus

<400> SEQUENCE: 63
accatcttca agagagaaga tggc                                              24
```

```
<210> SEQ ID NO 64
<211> LENGTH: 24
<212> TYPE: DNA
<213> ORGANISM: Cricetulus griseus

<400> SEQUENCE: 64
accatcttcc ttgatgaaga tgcc                                          24

<210> SEQ ID NO 65
<211> LENGTH: 24
<212> TYPE: DNA
<213> ORGANISM: Cricetulus griseus

<400> SEQUENCE: 65
gtcaccttca agtctgaaga tggt                                          24

<210> SEQ ID NO 66
<211> LENGTH: 24
<212> TYPE: DNA
<213> ORGANISM: Cricetulus griseus

<400> SEQUENCE: 66
ttcaccttct taagtgaaga tggt                                          24

<210> SEQ ID NO 67
<211> LENGTH: 195
<212> TYPE: PRT
<213> ORGANISM: Artificial
<220> FEATURE:
<223> OTHER INFORMATION: FokI-DDD amino acid sequence

<400> SEQUENCE: 67

Leu Val Lys Ser Glu Leu Glu Glu Lys Lys Ser Glu Leu Arg His Lys
1               5                   10                  15

Leu Lys Tyr Val Pro His Glu Tyr Ile Glu Leu Ile Glu Ile Ala Arg
            20                  25                  30

Asn Ser Thr Gln Asp Arg Ile Leu Glu Met Lys Val Met Glu Phe Phe
        35                  40                  45

Met Lys Val Tyr Gly Tyr Arg Gly Lys His Leu Gly Gly Ser Arg Lys
    50                  55                  60

Pro Asp Gly Ala Ile Tyr Thr Val Gly Ser Pro Ile Asp Tyr Gly Val
65                  70                  75                  80

Ile Val Asp Thr Lys Ala Tyr Ser Gly Gly Tyr Asn Leu Pro Ile Gly
                85                  90                  95

Gln Ala Asp Glu Met Gln Asp Tyr Val Glu Glu Asn Gln Thr Arg Asp
            100                 105                 110

Lys His Ile Asn Pro Asn Glu Trp Trp Lys Val Tyr Pro Ser Ser Val
        115                 120                 125

Thr Glu Phe Lys Phe Leu Phe Val Ser Gly His Phe Lys Gly Asn Tyr
    130                 135                 140

Lys Ala Gln Leu Thr Arg Leu Asn His Ile Thr Asn Cys Asn Gly Ala
145                 150                 155                 160

Val Leu Ser Val Glu Glu Leu Leu Ile Gly Gly Glu Met Ile Lys Ala
                165                 170                 175

Gly Thr Leu Thr Leu Glu Glu Val Arg Arg Lys Phe Asn Asn Gly Glu
            180                 185                 190

Ile Asn Phe
        195
```

<210> SEQ ID NO 68
<211> LENGTH: 195
<212> TYPE: PRT
<213> ORGANISM: Artificial
<220> FEATURE:
<223> OTHER INFORMATION: FokI-RRR amino acid sequence

<400> SEQUENCE: 68

```
Leu Val Lys Ser Glu Leu Glu Glu Lys Lys Ser Glu Leu Arg His Lys
1               5                   10                  15

Leu Lys Tyr Val Pro His Glu Tyr Ile Glu Leu Ile Glu Ile Ala Arg
            20                  25                  30

Asn Ser Thr Gln Asp Arg Ile Leu Glu Met Lys Val Met Glu Phe Phe
        35                  40                  45

Met Lys Val Tyr Gly Tyr Arg Gly Lys His Leu Gly Gly Ser Arg Lys
    50                  55                  60

Pro Asp Gly Ala Ile Tyr Thr Val Gly Ser Pro Ile Asp Tyr Gly Val
65                  70                  75                  80

Ile Val Asp Thr Lys Ala Tyr Ser Gly Gly Tyr Asn Leu Pro Ile Gly
                85                  90                  95

Gln Ala Arg Glu Met Gln Arg Tyr Val Glu Glu Asn Gln Thr Arg Asn
            100                 105                 110

Lys His Ile Asn Pro Asn Glu Trp Trp Lys Val Tyr Pro Ser Ser Val
        115                 120                 125

Thr Glu Phe Lys Phe Leu Phe Val Ser Gly His Phe Lys Gly Asn Tyr
    130                 135                 140

Lys Ala Gln Leu Thr Arg Leu Asn Arg Ile Thr Asn Cys Asn Gly Ala
145                 150                 155                 160

Val Leu Ser Val Glu Glu Leu Leu Ile Gly Gly Glu Met Ile Lys Ala
                165                 170                 175

Gly Thr Leu Thr Leu Glu Glu Val Arg Arg Lys Phe Asn Asn Gly Glu
            180                 185                 190

Ile Asn Phe
        195
```

<210> SEQ ID NO 69
<211> LENGTH: 195
<212> TYPE: PRT
<213> ORGANISM: Artificial
<220> FEATURE:
<223> OTHER INFORMATION: ND1-DDD amino acid sequence

<400> SEQUENCE: 69

```
Leu Val Lys Gly Glu Met Glu Lys Lys Lys Ser Asp Leu Arg His Lys
1               5                   10                  15

Leu Lys His Val Pro His Glu Tyr Ile Glu Leu Ile Glu Ile Ala Gln
            20                  25                  30

Asp Ser Lys Gln Asn Arg Leu Phe Glu Phe Lys Val Val Glu Phe Leu
        35                  40                  45

Lys Glu Val Tyr Asp Tyr Asn Gly Lys His Leu Gly Gly Ser Arg Lys
    50                  55                  60

Pro Asp Gly Ala Leu Tyr Thr Asn Gly Leu Lys Thr Asp Tyr Gly Ile
65                  70                  75                  80

Ile Leu Asp Thr Lys Ala Tyr Lys Asp Gly Tyr Ser Leu Pro Ile Ser
                85                  90                  95

Gln Ala Asp Glu Met Gln Asp Tyr Val Asp Glu Asn Asn Asn Arg Asp
```

```
                100              105              110
Ala Ile Ile Asn Pro Asn Glu Trp Trp Lys Val Tyr Pro Asn Ser Ile
        115              120              125

Leu Asp Phe Lys Phe Leu Phe Val Ser Gly Phe Phe Lys Gly Asp Tyr
        130              135              140

Lys Lys Gln Leu Ala Arg Val Ser Asn Leu Thr Lys Arg Lys Gly Ala
145              150              155              160

Val Leu Ser Val Glu Gln Leu Leu Gly Gly Glu Lys Ile Lys Asp
                165              170              175

Gly Ser Leu Thr Leu Glu Asp Val Gly Asp Lys Phe Asn Asn Asp Glu
                180              185              190

Ile Ile Phe
        195

<210> SEQ ID NO 70
<211> LENGTH: 195
<212> TYPE: PRT
<213> ORGANISM: Artificial
<220> FEATURE:
<223> OTHER INFORMATION: ND1-RRR amino acid sequence

<400> SEQUENCE: 70

Leu Val Lys Gly Glu Met Glu Lys Lys Ser Asp Leu Arg His Lys
1               5               10              15

Leu Lys His Val Pro His Glu Tyr Ile Glu Leu Ile Glu Ile Ala Gln
                20              25              30

Asp Ser Lys Gln Asn Arg Leu Phe Glu Phe Lys Val Val Glu Phe Leu
        35              40              45

Lys Glu Val Tyr Asp Tyr Asn Gly Lys His Leu Gly Gly Ser Arg Lys
50              55              60

Pro Asp Gly Ala Leu Tyr Thr Asn Gly Leu Lys Thr Asp Tyr Gly Ile
65              70              75              80

Ile Leu Asp Thr Lys Ala Tyr Lys Asp Gly Tyr Ser Leu Pro Ile Ser
                85              90              95

Gln Ala Arg Glu Met Gln Arg Tyr Val Asp Glu Asn Asn Asn Arg Asn
        100              105              110

Ala Ile Ile Asn Pro Asn Glu Trp Trp Lys Val Tyr Pro Asn Ser Ile
        115              120              125

Leu Asp Phe Lys Phe Leu Phe Val Ser Gly Phe Phe Lys Gly Asp Tyr
        130              135              140

Lys Lys Gln Leu Ala Arg Val Ser Arg Leu Thr Lys Arg Lys Gly Ala
145              150              155              160

Val Leu Ser Val Glu Gln Leu Leu Gly Gly Glu Lys Ile Lys Asp
                165              170              175

Gly Ser Leu Thr Leu Glu Asp Val Gly Asp Lys Phe Asn Asn Asp Glu
                180              185              190

Ile Ile Phe
        195

<210> SEQ ID NO 71
<211> LENGTH: 191
<212> TYPE: PRT
<213> ORGANISM: Artificial
<220> FEATURE:
<223> OTHER INFORMATION: ND2-DDD amino acid sequence

<400> SEQUENCE: 71
```

```
Ile Val Lys Ser Ser Ile Glu Met Ser Lys Ala Asn Met Arg Asp Asn
1               5                   10                  15
Leu Gln Met Leu Pro His Asp Tyr Ile Glu Leu Ile Glu Ile Ser Gln
            20                  25                  30
Asp Pro Tyr Gln Asn Arg Ile Phe Glu Met Lys Val Met Asp Leu Phe
                35                  40                  45
Ile Asn Glu Tyr Gly Phe Ser Gly Ser His Leu Gly Gly Ser Arg Lys
50                      55                  60
Pro Asp Gly Ala Met Tyr Ala His Gly Phe Gly Val Ile Val Asp Thr
65                  70                  75                  80
Lys Ala Tyr Lys Asp Gly Tyr Asn Leu Pro Ile Ser Gln Ala Asp Glu
                85                  90                  95
Met Glu Asp Tyr Val Arg Glu Asn Ile Asp Arg Asp Glu His Val Asn
            100                 105                 110
Ser Asn Arg Trp Trp Asn Ile Phe Pro Glu Asp Thr Asn Glu Tyr Lys
            115                 120                 125
Phe Leu Phe Val Ser Gly Phe Phe Lys Gly Asn Phe Glu Lys Gln Leu
            130                 135                 140
Glu Arg Ile Ser Ile Asp Thr Gly Val Gln Gly Gly Ala Leu Ser Val
145                 150                 155                 160
Glu His Leu Leu Leu Gly Ala Glu Tyr Ile Lys Arg Gly Ile Leu Thr
                165                 170                 175
Leu Tyr Asp Phe Lys Asn Ser Phe Leu Asn Lys Glu Ile Gln Phe
                180                 185                 190

<210> SEQ ID NO 72
<211> LENGTH: 191
<212> TYPE: PRT
<213> ORGANISM: Artificial
<220> FEATURE:
<223> OTHER INFORMATION: ND2-RRR amino acid sequence

<400> SEQUENCE: 72

Ile Val Lys Ser Ser Ile Glu Met Ser Lys Ala Asn Met Arg Asp Asn
1               5                   10                  15
Leu Gln Met Leu Pro His Asp Tyr Ile Glu Leu Ile Glu Ile Ser Gln
            20                  25                  30
Asp Pro Tyr Gln Asn Arg Ile Phe Glu Met Lys Val Met Asp Leu Phe
                35                  40                  45
Ile Asn Glu Tyr Gly Phe Ser Gly Ser His Leu Gly Gly Ser Arg Lys
50                      55                  60
Pro Asp Gly Ala Met Tyr Ala His Gly Phe Gly Val Ile Val Asp Thr
65                  70                  75                  80
Lys Ala Tyr Lys Asp Gly Tyr Asn Leu Pro Ile Ser Gln Ala Arg Glu
                85                  90                  95
Met Glu Arg Tyr Val Arg Glu Asn Ile Asp Arg Asn Glu His Val Asn
            100                 105                 110
Ser Asn Arg Trp Trp Asn Ile Phe Pro Glu Asp Thr Asn Glu Tyr Lys
            115                 120                 125
Phe Leu Phe Val Ser Gly Phe Phe Lys Gly Asn Phe Glu Lys Gln Leu
            130                 135                 140
Glu Arg Ile Ser Arg Asp Thr Gly Val Gln Gly Gly Ala Leu Ser Val
145                 150                 155                 160
Glu His Leu Leu Leu Gly Ala Glu Tyr Ile Lys Arg Gly Ile Leu Thr
                165                 170                 175
```

-continued

```
Leu Tyr Asp Phe Lys Asn Ser Phe Leu Asn Lys Glu Ile Gln Phe
            180                 185                 190
```

<210> SEQ ID NO 73
<211> LENGTH: 195
<212> TYPE: PRT
<213> ORGANISM: Artificial
<220> FEATURE:
<223> OTHER INFORMATION: FokI-S418P/K441E amino acid sequence

<400> SEQUENCE: 73

```
Leu Val Lys Ser Glu Leu Glu Glu Lys Lys Ser Glu Leu Arg His Lys
1               5                   10                  15

Leu Lys Tyr Val Pro His Glu Tyr Ile Glu Leu Ile Glu Ile Ala Arg
                20                  25                  30

Asn Pro Thr Gln Asp Arg Ile Leu Glu Met Lys Val Met Glu Phe Phe
            35                  40                  45

Met Lys Val Tyr Gly Tyr Arg Gly Glu His Leu Gly Gly Ser Arg Lys
    50                  55                  60

Pro Asp Gly Ala Ile Tyr Thr Val Gly Ser Pro Ile Asp Tyr Gly Val
65                  70                  75                  80

Ile Val Asp Thr Lys Ala Tyr Ser Gly Gly Tyr Asn Leu Pro Ile Gly
                85                  90                  95

Gln Ala Asp Glu Met Gln Arg Tyr Val Glu Glu Asn Gln Thr Arg Asn
            100                 105                 110

Lys His Ile Asn Pro Asn Glu Trp Trp Lys Val Tyr Pro Ser Ser Val
        115                 120                 125

Thr Glu Phe Lys Phe Leu Phe Val Ser Gly His Phe Lys Gly Asn Tyr
    130                 135                 140

Lys Ala Gln Leu Thr Arg Leu Asn His Ile Thr Asn Cys Asn Gly Ala
145                 150                 155                 160

Val Leu Ser Val Glu Glu Leu Leu Ile Gly Gly Glu Met Ile Lys Ala
                165                 170                 175

Gly Thr Leu Thr Leu Glu Glu Val Arg Arg Lys Phe Asn Asn Gly Glu
            180                 185                 190

Ile Asn Phe
        195
```

<210> SEQ ID NO 74
<211> LENGTH: 195
<212> TYPE: PRT
<213> ORGANISM: Artificial
<220> FEATURE:
<223> OTHER INFORMATION: ND1-S418P/K441E amino acid sequence

<400> SEQUENCE: 74

```
Leu Val Lys Gly Glu Met Glu Lys Lys Lys Ser Asp Leu Arg His Lys
1               5                   10                  15

Leu Lys His Val Pro His Glu Tyr Ile Glu Leu Ile Glu Ile Ala Gln
                20                  25                  30

Asp Pro Lys Gln Asn Arg Leu Phe Glu Phe Lys Val Val Glu Phe Leu
            35                  40                  45

Lys Glu Val Tyr Asp Tyr Asn Gly Glu His Leu Gly Gly Ser Arg Lys
    50                  55                  60

Pro Asp Gly Ala Leu Tyr Thr Asn Gly Leu Lys Thr Asp Tyr Gly Ile
65                  70                  75                  80

Ile Leu Asp Thr Lys Ala Tyr Lys Asp Gly Tyr Ser Leu Pro Ile Ser
                85                  90                  95
```

```
Gln Ala Asp Glu Met Gln Arg Tyr Val Asp Glu Asn Asn Arg Asn
            100                 105                 110

Ala Ile Ile Asn Pro Asn Glu Trp Trp Lys Val Tyr Pro Asn Ser Ile
            115                 120                 125

Leu Asp Phe Lys Phe Leu Phe Val Ser Gly Phe Lys Gly Asp Tyr
            130                 135                 140

Lys Lys Gln Leu Ala Arg Val Ser Asn Leu Thr Lys Arg Lys Gly Ala
145                 150                 155                 160

Val Leu Ser Val Glu Gln Leu Leu Gly Gly Lys Ile Lys Asp
                    165                 170                 175

Gly Ser Leu Thr Leu Glu Asp Val Gly Asp Lys Phe Asn Asn Asp Glu
                    180                 185                 190

Ile Ile Phe
        195

<210> SEQ ID NO 75
<211> LENGTH: 191
<212> TYPE: PRT
<213> ORGANISM: Artificial
<220> FEATURE:
<223> OTHER INFORMATION: ND2-S441E amino acid sequence

<400> SEQUENCE: 75

Ile Val Lys Ser Ser Ile Glu Met Ser Lys Ala Asn Met Arg Asp Asn
1               5                   10                  15

Leu Gln Met Leu Pro His Asp Tyr Ile Glu Leu Ile Glu Ile Ser Gln
                20                  25                  30

Asp Pro Tyr Gln Asn Arg Ile Phe Glu Met Lys Val Met Asp Leu Phe
            35                  40                  45

Ile Asn Glu Tyr Gly Phe Ser Gly Glu His Leu Gly Ser Arg Lys
50                  55                  60

Pro Asp Gly Ala Met Tyr Ala His Gly Phe Gly Val Ile Val Asp Thr
65                  70                  75                  80

Lys Ala Tyr Lys Asp Gly Tyr Asn Leu Pro Ile Ser Gln Ala Asp Glu
                85                  90                  95

Met Glu Arg Tyr Val Arg Glu Asn Ile Asp Arg Asn Glu His Val Asn
            100                 105                 110

Ser Asn Arg Trp Trp Asn Ile Phe Pro Glu Asp Thr Asn Glu Tyr Lys
            115                 120                 125

Phe Leu Phe Val Ser Gly Phe Phe Lys Gly Asn Phe Glu Lys Gln Leu
            130                 135                 140

Glu Arg Ile Ser Ile Asp Thr Gly Val Gln Gly Gly Ala Leu Ser Val
145                 150                 155                 160

Glu His Leu Leu Leu Gly Ala Glu Tyr Ile Lys Arg Gly Ile Leu Thr
                    165                 170                 175

Leu Tyr Asp Phe Lys Asn Ser Phe Leu Asn Lys Glu Ile Gln Phe
                    180                 185                 190

<210> SEQ ID NO 76
<211> LENGTH: 34
<212> TYPE: DNA
<213> ORGANISM: Artificial
<220> FEATURE:
<223> OTHER INFORMATION: FokI-cleaved CHO-K1 ZFA36-ZFA36 target 1st site

<400> SEQUENCE: 76
cagccaccat cttccactct gaagatggac aggt                             34
```

<210> SEQ ID NO 77
<211> LENGTH: 35
<212> TYPE: DNA
<213> ORGANISM: Artificial
<220> FEATURE:
<223> OTHER INFORMATION: FokI-cleaved CHO-K1 ZFA36-ZFA36 target 1st site

<400> SEQUENCE: 77
cagccaccat cttccactct tgaagatgga caggt                                35

<210> SEQ ID NO 78
<211> LENGTH: 38
<212> TYPE: DNA
<213> ORGANISM: Artificial
<220> FEATURE:
<223> OTHER INFORMATION: FokI-cleaved CHO-K1 ZFA36-ZFA36 target 1st site

<400> SEQUENCE: 78
cagccaccat cttccactca ctctgaagat ggacaggt                             38

<210> SEQ ID NO 79
<211> LENGTH: 34
<212> TYPE: DNA
<213> ORGANISM: Artificial
<220> FEATURE:
<223> OTHER INFORMATION: ND1-cleaved CHO-K1 ZFA36-ZFA36 target 1st site

<400> SEQUENCE: 79
cagccaccat cttccactct gaagatggac aggt                                 34

<210> SEQ ID NO 80
<211> LENGTH: 35
<212> TYPE: DNA
<213> ORGANISM: Artificial
<220> FEATURE:
<223> OTHER INFORMATION: ND1-cleaved CHO-K1 ZFA36-ZFA36 target 1st site

<400> SEQUENCE: 80
cagccaccat cttccaactc tgaagatgga caggt                                35

<210> SEQ ID NO 81
<211> LENGTH: 36
<212> TYPE: DNA
<213> ORGANISM: Artificial
<220> FEATURE:
<223> OTHER INFORMATION: ND1-cleaved CHO-K1 ZFA36-ZFA36 target 1st site

<400> SEQUENCE: 81
cagccaccat cttccactct ctgaagatgg acaggt                               36

<210> SEQ ID NO 82
<211> LENGTH: 38
<212> TYPE: DNA
<213> ORGANISM: Artificial
<220> FEATURE:
<223> OTHER INFORMATION: ND1-cleaved CHO-K1 ZFA36-ZFA36 target 1st site

<400> SEQUENCE: 82
cagccaccat cttccactca ctctgaagat ggacaggt                             38

<210> SEQ ID NO 83
<211> LENGTH: 32
<212> TYPE: DNA
<213> ORGANISM: Artificial
<220> FEATURE:

```
<223> OTHER INFORMATION: ND1-cleaved CHO-K1 ZFA36-ZFA36 target 1st site

<400> SEQUENCE: 83
cagccaccat cttcctctga agatggacag gt                                     32

<210> SEQ ID NO 84
<211> LENGTH: 25
<212> TYPE: DNA
<213> ORGANISM: Artificial
<220> FEATURE:
<223> OTHER INFORMATION: ND1-cleaved CHO-K1 ZFA36-ZFA36 target 1st site

<400> SEQUENCE: 84
cagcccactc tgaagatgga caggt                                             25

<210> SEQ ID NO 85
<211> LENGTH: 34
<212> TYPE: DNA
<213> ORGANISM: Artificial
<220> FEATURE:
<223> OTHER INFORMATION: ND2-cleaved CHO-K1 ZFA36-ZFA36 target 1st site

<400> SEQUENCE: 85
cagccaccat cttccactct gaagatggac aggt                                   34

<210> SEQ ID NO 86
<211> LENGTH: 35
<212> TYPE: DNA
<213> ORGANISM: Artificial
<220> FEATURE:
<223> OTHER INFORMATION: ND2-cleaved CHO-K1 ZFA36-ZFA36 target 1st site

<400> SEQUENCE: 86
cagccaccat cttccactct tgaagatgga caggt                                  35

<210> SEQ ID NO 87
<211> LENGTH: 36
<212> TYPE: DNA
<213> ORGANISM: Artificial
<220> FEATURE:
<223> OTHER INFORMATION: ND2-cleaved CHO-K1 ZFA36-ZFA36 target 1st site

<400> SEQUENCE: 87
cagccaccat cttccactct ctgaagatgg acaggt                                 36

<210> SEQ ID NO 88
<211> LENGTH: 32
<212> TYPE: DNA
<213> ORGANISM: Artificial
<220> FEATURE:
<223> OTHER INFORMATION: ND2-cleaved CHO-K1 ZFA36-ZFA36 target 1st site

<400> SEQUENCE: 88
cagccaccat cttcctctga agatggacag gt                                     32

<210> SEQ ID NO 89
<211> LENGTH: 30
<212> TYPE: DNA
<213> ORGANISM: Artificial
<220> FEATURE:
<223> OTHER INFORMATION: ND2-cleaved CHO-K1 ZFA36-ZFA36 target 1st site

<400> SEQUENCE: 89
cagccaccat ctttctgaag atggacaggt                                        30
```

```
<210> SEQ ID NO 90
<211> LENGTH: 34
<212> TYPE: DNA
<213> ORGANISM: Artificial
<220> FEATURE:
<223> OTHER INFORMATION: ND3-cleaved CHO-K1 ZFA36-ZFA36 target 1st site

<400> SEQUENCE: 90
cagccaccat cttccactct gaagatggac aggt                                34

<210> SEQ ID NO 91
<211> LENGTH: 34
<212> TYPE: DNA
<213> ORGANISM: Artificial
<220> FEATURE:
<223> OTHER INFORMATION: ND4-cleaved CHO-K1 ZFA36-ZFA36 target 1st site

<400> SEQUENCE: 91
cagccaccat cttccactct gaagatggac aggt                                34

<210> SEQ ID NO 92
<211> LENGTH: 34
<212> TYPE: DNA
<213> ORGANISM: Artificial
<220> FEATURE:
<223> OTHER INFORMATION: FokI-cleaved CHO-K1 ZFA36-ZFA36 target 2nd site

<400> SEQUENCE: 92
accttaccat cttcaagaga gaagatggct taaa                                34

<210> SEQ ID NO 93
<211> LENGTH: 36
<212> TYPE: DNA
<213> ORGANISM: Artificial
<220> FEATURE:
<223> OTHER INFORMATION: FokI-cleaved CHO-K1 ZFA36-ZFA36 target 2nd site

<400> SEQUENCE: 93
accttaccat cttcaagaga gagaagatgg cttaaa                              36

<210> SEQ ID NO 94
<211> LENGTH: 38
<212> TYPE: DNA
<213> ORGANISM: Artificial
<220> FEATURE:
<223> OTHER INFORMATION: FokI-cleaved CHO-K1 ZFA36-ZFA36 target 2nd site

<400> SEQUENCE: 94
accttaccat cttcaagaga gagagaagat ggcttaaa                            38

<210> SEQ ID NO 95
<211> LENGTH: 39
<212> TYPE: DNA
<213> ORGANISM: Artificial
<220> FEATURE:
<223> OTHER INFORMATION: FokI-cleaved CHO-K1 ZFA36-ZFA36 target 2nd site

<400> SEQUENCE: 95
accttaccat cttcaagagg agagagaaga tggcttaaa                           39

<210> SEQ ID NO 96
<211> LENGTH: 32
<212> TYPE: DNA
<213> ORGANISM: Artificial
<220> FEATURE:
<223> OTHER INFORMATION: FokI-cleaved CHO-K1 ZFA36-ZFA36 target 2nd site
```

```
<400> SEQUENCE: 96
accttaccat cttcaagaga agatggctta aa                                     32

<210> SEQ ID NO 97
<211> LENGTH: 268
<212> TYPE: DNA
<213> ORGANISM: Artificial
<220> FEATURE:
<223> OTHER INFORMATION: FokI-cleaved CHO-K1 ZFA36-ZFA36 target 2nd site

<400> SEQUENCE: 97
accttaccat cttcaagagc atgaacacat caccattcat taccaaaaat aaaaaatctt      60
actatgaaga gctcttggga atgggagtgt tagcctaatg agagaacaga cacttagcat     120
attctaggcc ttaggatcag tcaccaccac caaaaaacaa acaaacaaaa aacttaacac     180
atgttcatcc ccagttagtt taagtcaggg accaagtaag attcccatttt tgcagtagaa     240 tggtatcact taggtaagat ggcttaaa                                         268

<210> SEQ ID NO 98
<211> LENGTH: 34
<212> TYPE: DNA
<213> ORGANISM: Artificial
<220> FEATURE:
<223> OTHER INFORMATION: ND1-cleaved CHO-K1 ZFA36-ZFA36 target 2nd site

<400> SEQUENCE: 98
accttaccat cttcaagaga gaagatggct taaa                                  34

<210> SEQ ID NO 99
<211> LENGTH: 36
<212> TYPE: DNA
<213> ORGANISM: Artificial
<220> FEATURE:
<223> OTHER INFORMATION: ND1-cleaved CHO-K1 ZFA36-ZFA36 target 2nd site

<400> SEQUENCE: 99
accttaccat cttcaagaga gagaagatgg cttaaa                                36

<210> SEQ ID NO 100
<211> LENGTH: 38
<212> TYPE: DNA
<213> ORGANISM: Artificial
<220> FEATURE:
<223> OTHER INFORMATION: ND1-cleaved CHO-K1 ZFA36-ZFA36 target 2nd site

<400> SEQUENCE: 100
accttaccat cttcaagaga gagagaagat ggcttaaa                              38

<210> SEQ ID NO 101
<211> LENGTH: 32
<212> TYPE: DNA
<213> ORGANISM: Artificial
<220> FEATURE:
<223> OTHER INFORMATION: ND1-cleaved CHO-K1 ZFA36-ZFA36 target 2nd site

<400> SEQUENCE: 101
accttaccat cttcaataga agatggctta aa                                    32

<210> SEQ ID NO 102
<211> LENGTH: 30
<212> TYPE: DNA
<213> ORGANISM: Artificial
<220> FEATURE:
<223> OTHER INFORMATION: ND1-cleaved CHO-K1 ZFA36-ZFA36 target 2nd site
```

-continued

```
<400> SEQUENCE: 102
accttaccat cttcaagagg atggcttaaa                                        30

<210> SEQ ID NO 103
<211> LENGTH: 34
<212> TYPE: DNA
<213> ORGANISM: Artificial
<220> FEATURE:
<223> OTHER INFORMATION: ND2-cleaved CHO-K1 ZFA36-ZFA36 target 2nd site

<400> SEQUENCE: 103
accttaccat cttcaagaga gaagatggct taaa                                   34

<210> SEQ ID NO 104
<211> LENGTH: 35
<212> TYPE: DNA
<213> ORGANISM: Artificial
<220> FEATURE:
<223> OTHER INFORMATION: ND2-cleaved CHO-K1 ZFA36-ZFA36 target 2nd site

<400> SEQUENCE: 104
accttaccat cttcaaagag agaagatggc ttaaa                                  35

<210> SEQ ID NO 105
<211> LENGTH: 36
<212> TYPE: DNA
<213> ORGANISM: Artificial
<220> FEATURE:
<223> OTHER INFORMATION: ND2-cleaved CHO-K1 ZFA36-ZFA36 target 2nd site

<400> SEQUENCE: 105
accttaccat cttcaagaga gagaagatgg cttaaa                                 36

<210> SEQ ID NO 106
<211> LENGTH: 38
<212> TYPE: DNA
<213> ORGANISM: Artificial
<220> FEATURE:
<223> OTHER INFORMATION: ND2-cleaved CHO-K1 ZFA36-ZFA36 target 2nd site

<400> SEQUENCE: 106
accttaccat cttcaagaga gagagaagat ggcttaaa                               38

<210> SEQ ID NO 107
<211> LENGTH: 105
<212> TYPE: DNA
<213> ORGANISM: Artificial
<220> FEATURE:
<223> OTHER INFORMATION: ND2-cleaved CHO-K1 ZFA36-ZFA36 target 2nd site

<400> SEQUENCE: 107
accttaccat cttcaggtct tcctggtgta gaatccctag tctttggtgg tgtcatataa       60
gtcttttgtt gttgaatgca ttcttaagag agaagatggc ttaaa                      105

<210> SEQ ID NO 108
<211> LENGTH: 34
<212> TYPE: DNA
<213> ORGANISM: Artificial
<220> FEATURE:
<223> OTHER INFORMATION: ND3-cleaved CHO-K1 ZFA36-ZFA36 target 2nd site

<400> SEQUENCE: 108
accttaccat cttcaagaga gaagatggct taaa                                   34
```

<210> SEQ ID NO 109
<211> LENGTH: 36
<212> TYPE: DNA
<213> ORGANISM: Artificial
<220> FEATURE:
<223> OTHER INFORMATION: ND3-cleaved CHO-K1 ZFA36-ZFA36 target 2nd site

<400> SEQUENCE: 109
accttaccat cttcaagaga gagaagatgg cttaaa                                    36

<210> SEQ ID NO 110
<211> LENGTH: 32
<212> TYPE: DNA
<213> ORGANISM: Artificial
<220> FEATURE:
<223> OTHER INFORMATION: ND3-cleaved CHO-K1 ZFA36-ZFA36 target 2nd site

<400> SEQUENCE: 110
accttaccat cttcaagaga agatggctta aa                                        32

<210> SEQ ID NO 111
<211> LENGTH: 26
<212> TYPE: DNA
<213> ORGANISM: Artificial
<220> FEATURE:
<223> OTHER INFORMATION: ND3-cleaved CHO-K1 ZFA36-ZFA36 target 2nd site

<400> SEQUENCE: 111
accttaccat cttcagttgg cttaaa                                               26

<210> SEQ ID NO 112
<211> LENGTH: 34
<212> TYPE: DNA
<213> ORGANISM: Artificial
<220> FEATURE:
<223> OTHER INFORMATION: ND4-cleaved CHO-K1 ZFA36-ZFA36 target 2nd site

<400> SEQUENCE: 112
cagccaccat cttcaagaga gaagatggct taaa                                      34

<210> SEQ ID NO 113
<211> LENGTH: 30
<212> TYPE: DNA
<213> ORGANISM: Artificial
<220> FEATURE:
<223> OTHER INFORMATION: forward primer for vector amplification for
      ptTALE-ND substitution, ptTALEN-inverse-F

<400> SEQUENCE: 113
taaaaaatca gcctcgactg tgccttctag                                           30

<210> SEQ ID NO 114
<211> LENGTH: 22
<212> TYPE: DNA
<213> ORGANISM: Artificial
<220> FEATURE:
<223> OTHER INFORMATION: reverse primer for vector amplification for
      ptTALE-ND substitution, NC-inverse-R_2

<400> SEQUENCE: 114
ctgggatctg atcaattccg gc                                                   22

<210> SEQ ID NO 115
<211> LENGTH: 48
<212> TYPE: DNA
<213> ORGANISM: Artificial

```
<220> FEATURE:
<223> OTHER INFORMATION: forward primer for insert amplification for
      ptTALE-ND substitution, ND1-NC-F_v2

<400> SEQUENCE: 115
ttgatcagat cccagttagt aaagggagag atggagaaga aaaagagc                48

<210> SEQ ID NO 116
<211> LENGTH: 46
<212> TYPE: DNA
<213> ORGANISM: Artificial
<220> FEATURE:
<223> OTHER INFORMATION: reverse primer for insert amplification for
      ptTALE-ND substitution, ND1-ptTALEN-R

<400> SEQUENCE: 116
gaggctgatt ttttagaaga tgatctcatc gttgttgaac ttatcc                  46

<210> SEQ ID NO 117
<211> LENGTH: 50
<212> TYPE: DNA
<213> ORGANISM: Cricetulus griseus

<400> SEQUENCE: 117
tgcccagaag actcccgccc atctcccaga aagcctcgac ttgcagatca              50

<210> SEQ ID NO 118
<211> LENGTH: 51
<212> TYPE: DNA
<213> ORGANISM: Cricetulus griseus

<400> SEQUENCE: 118
tgaaccaggc tatgacctag atttattttg tattcctaat cactatgtcg a            51

<210> SEQ ID NO 119
<211> LENGTH: 318
<212> TYPE: PRT
<213> ORGANISM: Artificial Sequence
<220> FEATURE:
<223> OTHER INFORMATION: ZF(ZFA36A)-ND1 amino acid sequence

<400> SEQUENCE: 119

Met Gly His His His His His His Met Arg Leu Glu Pro Lys Lys Lys
1               5                   10                  15

Arg Lys Val Ala Ala Asp Tyr Lys Asp Asp Asp Lys Ser Arg
            20                  25                  30

Pro Gly Glu Lys Pro Tyr Lys Cys Pro Glu Cys Gly Lys Ser Phe Ser
        35                  40                  45

Thr Ser Gly His Leu Val Arg His Gln Arg Thr His Thr Gly Glu Lys
    50                  55                  60

Pro Tyr Lys Cys Pro Glu Cys Gly Lys Ser Phe Ser Thr Ser Gly Asn
65                  70                  75                  80

Leu Val Arg His Gln Arg Thr His Thr Gly Lys Pro Tyr Lys Cys
            85                  90                  95

Pro Glu Cys Gly Lys Ser Phe Ser Gln Ser Ser Asn Leu Val Arg His
            100                 105                 110

Gln Arg Thr His Thr Gly Ala Ala Ala Arg Ala Leu Val Lys Gly Glu
            115                 120                 125

Met Glu Lys Lys Lys Ser Asp Leu Arg His Lys Leu Lys His Val Pro
        130                 135                 140

His Glu Tyr Ile Glu Leu Ile Glu Ile Ala Gln Asp Ser Lys Gln Asn
```

```
                145                 150                 155                 160
        Arg Leu Phe Glu Phe Lys Val Val Glu Phe Leu Lys Glu Val Tyr Asp
                        165                 170                 175
        Tyr Asn Gly Lys His Leu Gly Gly Ser Arg Lys Pro Asp Gly Ala Leu
                        180                 185                 190
        Tyr Thr Asn Gly Leu Lys Thr Asp Tyr Gly Ile Ile Leu Asp Thr Lys
                        195                 200                 205
        Ala Tyr Lys Asp Gly Tyr Ser Leu Pro Ile Ser Gln Ala Asp Glu Met
                        210                 215                 220
        Gln Arg Tyr Val Asp Glu Asn Asn Arg Asn Ala Ile Ile Asn Pro
        225                 230                 235                 240
        Asn Glu Trp Trp Lys Val Tyr Pro Asn Ser Ile Leu Asp Phe Lys Phe
                        245                 250                 255
        Leu Phe Val Ser Gly Phe Phe Lys Gly Asp Tyr Lys Lys Gln Leu Ala
                        260                 265                 270
        Arg Val Ser Asn Leu Thr Lys Arg Lys Gly Ala Val Leu Ser Val Glu
                        275                 280                 285
        Gln Leu Leu Leu Gly Gly Glu Lys Ile Lys Asp Gly Ser Leu Thr Leu
                        290                 295                 300
        Glu Asp Val Gly Asp Lys Phe Asn Asn Asp Glu Ile Ile Phe
        305                 310                 315

<210> SEQ ID NO 120
<211> LENGTH: 318
<212> TYPE: PRT
<213> ORGANISM: Artificial Sequence
<220> FEATURE:
<223> OTHER INFORMATION: ZF(ZFL1)-ND1 amino acid sequence

<400> SEQUENCE: 120

Met Gly His His His His His His Met Arg Leu Glu Pro Lys Lys Lys
        1               5                   10                  15
        Arg Lys Val Ala Ala Ala Asp Tyr Lys Asp Asp Asp Lys Ser Arg
                        20                  25                  30
        Pro His Glu Arg Pro Phe Gln Cys Arg Ile Cys Met Arg Asn Phe Ser
                        35                  40                  45
        Asp Arg Ser Asn Leu Thr Arg His Thr Arg Thr His Thr Gly Glu Lys
        50                  55                  60
        Pro Phe Gln Cys Arg Ile Cys Met Arg Asn Phe Ser Leu Arg His His
        65                  70                  75                  80
        Leu Thr Arg His Leu Arg Thr His Thr Gly Glu Lys Pro Phe Gln Cys
                        85                  90                  95
        Arg Ile Cys Met Arg Asn Phe Ser Gln Lys Ala Asn Leu Thr Arg His
                        100                 105                 110
        Leu Arg Thr His Thr Gly Ala Ala Ala Arg Ala Leu Val Lys Gly Glu
                        115                 120                 125
        Met Glu Lys Lys Lys Ser Asp Leu Arg His Lys Leu Lys His Val Pro
                        130                 135                 140
        His Glu Tyr Ile Glu Leu Ile Glu Ile Ala Gln Asp Ser Lys Gln Asn
        145                 150                 155                 160
        Arg Leu Phe Glu Phe Lys Val Val Glu Phe Leu Lys Glu Val Tyr Asp
                        165                 170                 175
        Tyr Asn Gly Lys His Leu Gly Gly Ser Arg Lys Pro Asp Gly Ala Leu
                        180                 185                 190
        Tyr Thr Asn Gly Leu Lys Thr Asp Tyr Gly Ile Ile Leu Asp Thr Lys
```

```
            195                 200                 205
Ala Tyr Lys Asp Gly Tyr Ser Leu Pro Ile Ser Gln Ala Asp Glu Met
210                 215                 220

Gln Arg Tyr Val Asp Glu Asn Asn Arg Asn Ala Ile Ile Asn Pro
225                 230                 235                 240

Asn Glu Trp Trp Lys Val Tyr Pro Asn Ser Ile Leu Asp Phe Lys Phe
                245                 250                 255

Leu Phe Val Ser Gly Phe Phe Lys Gly Asp Tyr Lys Lys Gln Leu Ala
                260                 265                 270

Arg Val Ser Asn Leu Thr Lys Arg Lys Gly Ala Val Leu Ser Val Glu
                275                 280                 285

Gln Leu Leu Gly Gly Glu Lys Ile Lys Asp Gly Ser Leu Thr Leu
290                 295                 300

Glu Asp Val Gly Asp Lys Phe Asn Asn Asp Glu Ile Ile Phe
305                 310                 315

<210> SEQ ID NO 121
<211> LENGTH: 318
<212> TYPE: PRT
<213> ORGANISM: Artificial Sequence
<220> FEATURE:
<223> OTHER INFORMATION: ZF(ZFA36A)-FokI amino acid sequence

<400> SEQUENCE: 121

Met Gly His His His His His His Met Arg Leu Glu Pro Lys Lys Lys
1               5                   10                  15

Arg Lys Val Ala Ala Ala Asp Tyr Lys Asp Asp Asp Asp Lys Ser Arg
                20                  25                  30

Pro Gly Glu Lys Pro Tyr Lys Cys Pro Glu Cys Gly Lys Ser Phe Ser
            35                  40                  45

Thr Ser Gly His Leu Val Arg His Gln Arg Thr His Thr Gly Glu Lys
        50                  55                  60

Pro Tyr Lys Cys Pro Glu Cys Gly Lys Ser Phe Ser Thr Ser Gly Asn
65                  70                  75                  80

Leu Val Arg His Gln Arg Thr His Thr Gly Glu Lys Pro Tyr Lys Cys
                85                  90                  95

Pro Glu Cys Gly Lys Ser Phe Ser Gln Ser Ser Asn Leu Val Arg His
            100                 105                 110

Gln Arg Thr His Thr Gly Ala Ala Ala Arg Ala Leu Val Lys Ser Glu
        115                 120                 125

Leu Glu Glu Lys Lys Ser Glu Leu Arg His Lys Leu Lys Tyr Val Pro
    130                 135                 140

His Glu Tyr Ile Glu Leu Ile Glu Ile Ala Arg Asn Ser Thr Gln Asp
145                 150                 155                 160

Arg Ile Leu Glu Met Lys Val Met Glu Phe Phe Met Lys Val Tyr Gly
                165                 170                 175

Tyr Arg Gly Lys His Leu Gly Gly Ser Arg Lys Pro Asp Gly Ala Ile
                180                 185                 190

Tyr Thr Val Gly Ser Pro Ile Asp Tyr Gly Val Ile Val Asp Thr Lys
            195                 200                 205

Ala Tyr Ser Gly Gly Tyr Asn Leu Pro Ile Gly Gln Ala Asp Glu Met
        210                 215                 220

Gln Arg Tyr Val Glu Glu Asn Gln Thr Arg Asn Lys His Ile Asn Pro
225                 230                 235                 240

Asn Glu Trp Trp Lys Val Tyr Pro Ser Ser Val Thr Glu Phe Lys Phe
```

```
                        245                 250                 255
Leu Phe Val Ser Gly His Phe Lys Gly Asn Tyr Lys Ala Gln Leu Thr
            260                 265                 270

Arg Leu Asn His Ile Thr Asn Cys Asn Gly Ala Val Leu Ser Val Glu
        275                 280                 285

Glu Leu Leu Ile Gly Gly Glu Met Ile Lys Ala Gly Thr Leu Thr Leu
        290                 295                 300

Glu Glu Val Arg Arg Lys Phe Asn Asn Gly Glu Ile Asn Phe
305                 310                 315

<210> SEQ ID NO 122
<211> LENGTH: 318
<212> TYPE: PRT
<213> ORGANISM: Artificial Sequence
<220> FEATURE:
<223> OTHER INFORMATION: ZF(ZFL1)-FokI amino acid sequence

<400> SEQUENCE: 122

Met Gly His His His His His His Met Arg Leu Glu Pro Lys Lys Lys
1               5                   10                  15

Arg Lys Val Ala Ala Ala Asp Tyr Lys Asp Asp Asp Lys Ser Arg
            20                  25                  30

Pro His Glu Arg Pro Phe Gln Cys Arg Ile Cys Met Arg Asn Phe Ser
        35                  40                  45

Asp Arg Ser Asn Leu Thr Arg His Thr Arg Thr His Thr Gly Glu Lys
    50                  55                  60

Pro Phe Gln Cys Arg Ile Cys Met Arg Asn Phe Ser Leu Arg His His
65                  70                  75                  80

Leu Thr Arg His Leu Arg Thr His Thr Gly Glu Lys Pro Phe Gln Cys
                85                  90                  95

Arg Ile Cys Met Arg Asn Phe Ser Gln Lys Ala Asn Leu Thr Arg His
            100                 105                 110

Leu Arg Thr His Thr Gly Ala Ala Ala Arg Ala Leu Val Lys Ser Glu
        115                 120                 125

Leu Glu Glu Lys Lys Ser Glu Leu Arg His Lys Leu Lys Tyr Val Pro
    130                 135                 140

His Glu Tyr Ile Glu Leu Ile Glu Ile Ala Arg Asn Ser Thr Gln Asp
145                 150                 155                 160

Arg Ile Leu Glu Met Lys Val Met Glu Phe Phe Met Lys Val Tyr Gly
                165                 170                 175

Tyr Arg Gly Lys His Leu Gly Gly Ser Arg Lys Pro Asp Gly Ala Ile
            180                 185                 190

Tyr Thr Val Gly Ser Pro Ile Asp Tyr Gly Val Ile Val Asp Thr Lys
        195                 200                 205

Ala Tyr Ser Gly Gly Tyr Asn Leu Pro Ile Gly Gln Ala Asp Glu Met
    210                 215                 220

Gln Arg Tyr Val Glu Glu Asn Gln Thr Arg Asn Lys His Ile Asn Pro
225                 230                 235                 240

Asn Glu Trp Trp Lys Val Tyr Pro Ser Ser Val Thr Glu Phe Lys Phe
                245                 250                 255

Leu Phe Val Ser Gly His Phe Lys Gly Asn Tyr Lys Ala Gln Leu Thr
            260                 265                 270

Arg Leu Asn His Ile Thr Asn Cys Asn Gly Ala Val Leu Ser Val Glu
        275                 280                 285

Glu Leu Leu Ile Gly Gly Glu Met Ile Lys Ala Gly Thr Leu Thr Leu
```

```
              290                 295                 300
Glu Glu Val Arg Arg Lys Phe Asn Asn Gly Glu Ile Asn Phe
305                 310                 315

<210> SEQ ID NO 123
<211> LENGTH: 24
<212> TYPE: DNA
<213> ORGANISM: Artificial Sequence
<220> FEATURE:
<223> OTHER INFORMATION: ZFN target site
<220> FEATURE:
<221> NAME/KEY: misc_feature
<222> LOCATION: (10)..(15)
<223> OTHER INFORMATION: n is a, c, g, or t

<400> SEQUENCE: 123
accatcttcn nnnnngaaga tggt                                          24

<210> SEQ ID NO 124
<211> LENGTH: 24
<212> TYPE: DNA
<213> ORGANISM: Artificial Sequence
<220> FEATURE:
<223> OTHER INFORMATION: ZFN target site
<220> FEATURE:
<221> NAME/KEY: misc_feature
<222> LOCATION: (10)..(15)
<223> OTHER INFORMATION: n is a, c, g, or t

<400> SEQUENCE: 124
accatcttcn nnnnngaaga tggt                                          24

<210> SEQ ID NO 125
<211> LENGTH: 195
<212> TYPE: PRT
<213> ORGANISM: Flavobacterium okeanokoites

<400> SEQUENCE: 125

Leu Val Lys Ser Glu Leu Glu Glu Lys Lys Ser Glu Leu Arg His Lys
1               5                   10                  15

Leu Lys Tyr Val Pro His Glu Tyr Ile Glu Leu Ile Glu Ile Ala Arg
            20                  25                  30

Asn Ser Thr Gln Asp Arg Ile Leu Glu Met Lys Val Met Glu Phe Phe
        35                  40                  45

Met Lys Val Tyr Gly Tyr Arg Gly Lys His Leu Gly Gly Ser Arg Lys
    50                  55                  60

Pro Asp Gly Ala Ile Tyr Thr Val Gly Ser Pro Ile Asp Tyr Gly Val
65                  70                  75                  80

Ile Val Asp Thr Lys Ala Tyr Ser Gly Gly Tyr Asn Leu Pro Ile Gly
                85                  90                  95

Gln Ala Asp Glu Met Gln Arg Tyr Val Glu Glu Asn Gln Thr Arg Asn
            100                 105                 110

Lys His Ile Asn Pro Asn Glu Trp Trp Lys Val Tyr Pro Ser Ser Val
        115                 120                 125

Thr Glu Phe Lys Phe Leu Phe Val Ser Gly His Phe Lys Gly Asn Tyr
    130                 135                 140

Lys Ala Gln Leu Thr Arg Leu Asn His Ile Thr Asn Cys Asn Gly Ala
145                 150                 155                 160

Val Leu Ser Val Glu Glu Leu Leu Ile Gly Gly Glu Met Ile Lys Ala
                165                 170                 175

Gly Thr Leu Thr Leu Glu Glu Val Arg Arg Lys Phe Asn Asn Gly Glu
```

-continued

```
                180                 185                 190

Ile Asn Phe
        195

<210> SEQ ID NO 126
<211> LENGTH: 195
<212> TYPE: PRT
<213> ORGANISM: Bacillus sp. SGD-V-76

<400> SEQUENCE: 126

Leu Val Lys Gly Glu Met Glu Lys Lys Ser Asp Leu Arg His Lys
1               5                   10                  15

Leu Lys His Val Pro His Glu Tyr Ile Glu Leu Ile Glu Ile Ala Gln
            20                  25                  30

Asp Ser Lys Gln Asn Arg Leu Phe Glu Phe Lys Val Val Glu Phe Leu
        35                  40                  45

Lys Glu Val Tyr Asp Tyr Asn Gly Lys His Leu Gly Gly Ser Arg Lys
    50                  55                  60

Pro Asp Gly Ala Leu Tyr Thr Asn Gly Leu Lys Thr Asp Tyr Gly Ile
65                  70                  75                  80

Ile Leu Asp Thr Lys Ala Tyr Lys Asp Gly Tyr Ser Leu Pro Ile Ser
                85                  90                  95

Gln Ala Asp Glu Met Gln Arg Tyr Val Asp Glu Asn Asn Arg Asn
            100                 105                 110

Ala Ile Ile Asn Pro Asn Glu Trp Trp Lys Val Tyr Pro Asn Ser Ile
        115                 120                 125

Leu Asp Phe Lys Phe Leu Phe Val Ser Gly Phe Lys Gly Asp Tyr
    130                 135                 140

Lys Lys Gln Leu Ala Arg Val Ser Asn Leu Thr Lys Arg Lys Gly Ala
145                 150                 155                 160

Val Leu Ser Val Glu Gln Leu Leu Gly Glu Lys Ile Lys Asp
                165                 170                 175

Gly Ser Leu Thr Leu Glu Asp Val Gly Asp Lys Phe Asn Asn Asp Glu
            180                 185                 190

Ile Ile Phe
        195

<210> SEQ ID NO 127
<211> LENGTH: 191
<212> TYPE: PRT
<213> ORGANISM: Clostridium botulinum

<400> SEQUENCE: 127

Ile Val Lys Ser Ser Ile Glu Met Ser Lys Ala Asn Met Arg Asp Asn
1               5                   10                  15

Leu Gln Met Leu Pro His Asp Tyr Ile Glu Leu Ile Glu Ile Ser Gln
            20                  25                  30

Asp Pro Tyr Gln Asn Arg Ile Phe Glu Met Lys Val Met Asp Leu Phe
        35                  40                  45

Ile Asn Glu Tyr Gly Phe Ser Gly Ser His Leu Gly Gly Ser Arg Lys
    50                  55                  60

Pro Asp Gly Ala Met Tyr Ala His Gly Phe Gly Val Ile Val Asp Thr
65                  70                  75                  80

Lys Ala Tyr Lys Asp Gly Tyr Asn Leu Pro Ile Ser Gln Ala Asp Glu
                85                  90                  95

Met Glu Arg Tyr Val Arg Glu Asn Ile Asp Arg Asn Glu His Val Asn
```

```
            100                 105                 110

Ser Asn Arg Trp Trp Asn Ile Phe Pro Glu Asp Thr Asn Glu Tyr Lys
            115                 120                 125

Phe Leu Phe Val Ser Gly Phe Lys Gly Asn Phe Glu Lys Gln Leu
        130                 135                 140

Glu Arg Ile Ser Ile Asp Thr Gly Val Gln Gly Ala Leu Ser Val
145                 150                 155                 160

Glu His Leu Leu Leu Gly Ala Glu Tyr Ile Lys Arg Gly Ile Leu Thr
            165                 170                 175

Leu Tyr Asp Phe Lys Asn Ser Phe Leu Asn Lys Glu Ile Gln Phe
            180                 185                 190

<210> SEQ ID NO 128
<211> LENGTH: 195
<212> TYPE: PRT
<213> ORGANISM: Clostridium sp. 7_2_43FAA

<400> SEQUENCE: 128

Gly Ile Lys Ser Asn Ile Ser Leu Leu Lys Asp Glu Leu Arg Gly Gln
1               5                   10                  15

Ile Ser His Ile Ser His Glu Tyr Leu Ser Leu Ile Asp Leu Ala Phe
            20                  25                  30

Asp Ser Lys Gln Asn Arg Leu Phe Glu Met Lys Val Leu Glu Leu Leu
        35                  40                  45

Val Asn Glu Tyr Gly Phe Lys Gly Arg His Leu Gly Gly Ser Arg Lys
    50                  55                  60

Pro Asp Gly Ile Val Tyr Ser Thr Thr Leu Glu Asp Asn Phe Gly Ile
65                  70                  75                  80

Ile Val Asp Thr Lys Ala Tyr Ser Glu Gly Tyr Ser Leu Pro Ile Ser
                85                  90                  95

Gln Ala Asp Glu Met Glu Arg Tyr Val Arg Glu Asn Ser Asn Arg Asp
            100                 105                 110

Glu Glu Val Asn Pro Asn Lys Trp Trp Glu Asn Phe Ser Glu Glu Val
        115                 120                 125

Lys Lys Tyr Tyr Phe Val Phe Ile Ser Gly Ser Phe Gly Lys Phe
    130                 135                 140

Glu Glu Gln Leu Arg Arg Leu Ser Met Thr Thr Gly Val Asn Gly Ser
145                 150                 155                 160

Ala Val Asn Val Val Asn Leu Leu Gly Ala Glu Lys Ile Arg Ser
                165                 170                 175

Gly Glu Met Thr Ile Glu Glu Leu Glu Arg Ala Met Phe Asn Asn Ser
            180                 185                 190

Glu Phe Ile
        195

<210> SEQ ID NO 129
<211> LENGTH: 212
<212> TYPE: PRT
<213> ORGANISM: Clostridiales bacterium KA00134

<400> SEQUENCE: 129

Ile Ser Lys Thr Asn Ile Leu Glu Leu Lys Asp Lys Val Arg Asp Lys
1               5                   10                  15

Leu Lys Tyr Val Asp His Arg Tyr Leu Ala Leu Ile Asp Leu Ala Tyr
            20                  25                  30

Asp Gly Thr Ala Asn Arg Asp Phe Glu Ile Gln Thr Ile Asp Leu Leu
```

-continued

```
                35                  40                  45
Ile Asn Glu Leu Lys Phe Lys Gly Val Arg Leu Gly Glu Ser Arg Lys
 50                  55                  60
Pro Asp Gly Ile Ile Ser Tyr Asn Ile Asn Gly Val Ile Asp Asn
 65                  70                  75                  80
Lys Ala Tyr Ser Thr Gly Tyr Asn Leu Pro Ile Asn Gln Ala Asp Glu
                 85                  90                  95
Met Ile Arg Tyr Ile Glu Glu Asn Gln Thr Arg Asp Glu Lys Ile Asn
             100                 105                 110
Ser Asn Lys Trp Trp Glu Ser Phe Asp Glu Lys Val Lys Asp Phe Asn
         115                 120                 125
Tyr Leu Phe Val Ser Ser Phe Phe Lys Gly Asn Phe Lys Asn Asn Leu
 130                 135                 140
Lys His Ile Ala Asn Arg Thr Gly Val Asn Gly Gly Ala Ile Asn Val
 145                 150                 155                 160
Glu Asn Leu Leu Tyr Phe Ala Glu Glu Leu Lys Ala Gly Arg Ile Ser
                 165                 170                 175
Tyr Leu Asp Ser Phe Lys Met Tyr Asn Asn Asp Glu Ile Tyr Leu Gly
             180                 185                 190
Asp Ile Ser Asp Tyr Ser Tyr Val Lys Phe Ala Ala Glu Glu Glu Gly
         195                 200                 205
Glu Tyr Leu Thr
     210
```

<210> SEQ ID NO 130
<211> LENGTH: 9
<212> TYPE: PRT
<213> ORGANISM: Flavobacterium okeanokoites

<400> SEQUENCE: 130

```
Ile Ala Arg Asn Ser Thr Gln Asp Arg
 1               5
```

<210> SEQ ID NO 131
<211> LENGTH: 9
<212> TYPE: PRT
<213> ORGANISM: Flavobacterium okeanokoites

<400> SEQUENCE: 131

```
Gly Tyr Arg Gly Lys His Leu Gly Gly
 1               5
```

<210> SEQ ID NO 132
<211> LENGTH: 9
<212> TYPE: PRT
<213> ORGANISM: Artificial Sequence
<220> FEATURE:
<223> OTHER INFORMATION: FokI-Sharkey

<400> SEQUENCE: 132

```
Ile Ala Arg Asn Pro Thr Gln Asp Arg
 1               5
```

<210> SEQ ID NO 133
<211> LENGTH: 9
<212> TYPE: PRT
<213> ORGANISM: Artificial Sequence
<220> FEATURE:
<223> OTHER INFORMATION: FokI-Sharkey

<400> SEQUENCE: 133

```
Gly Tyr Arg Gly Glu His Leu Gly Gly
1               5

<210> SEQ ID NO 134
<211> LENGTH: 9
<212> TYPE: PRT
<213> ORGANISM: Bacillus sp. SGD-V-76

<400> SEQUENCE: 134

Ile Ala Gln Asp Ser Lys Gln Asn Arg
1               5

<210> SEQ ID NO 135
<211> LENGTH: 9
<212> TYPE: PRT
<213> ORGANISM: Bacillus sp. SGD-V-76

<400> SEQUENCE: 135

Asp Tyr Asn Gly Lys His Leu Gly Gly
1               5

<210> SEQ ID NO 136
<211> LENGTH: 9
<212> TYPE: PRT
<213> ORGANISM: Artificial Sequence
<220> FEATURE:
<223> OTHER INFORMATION: ND1-Sharkey

<400> SEQUENCE: 136

Ile Ala Gln Asp Pro Lys Gln Asn Arg
1               5

<210> SEQ ID NO 137
<211> LENGTH: 9
<212> TYPE: PRT
<213> ORGANISM: Artificial Sequence
<220> FEATURE:
<223> OTHER INFORMATION: ND1-Sharkey

<400> SEQUENCE: 137

Asp Tyr Asn Gly Glu His Leu Gly Gly
1               5

<210> SEQ ID NO 138
<211> LENGTH: 9
<212> TYPE: PRT
<213> ORGANISM: Clostridium botulinum

<400> SEQUENCE: 138

Ile Ser Gln Asp Pro Tyr Gln Asn Arg
1               5

<210> SEQ ID NO 139
<211> LENGTH: 9
<212> TYPE: PRT
<213> ORGANISM: Clostridium botulinum

<400> SEQUENCE: 139

Gly Phe Ser Gly Ser His Leu Gly Gly
1               5

<210> SEQ ID NO 140
<211> LENGTH: 9
<212> TYPE: PRT
<213> ORGANISM: Artificial Sequence
```

```
<220> FEATURE:
<223> OTHER INFORMATION: ND2-Sharkey

<400> SEQUENCE: 140

Ile Ser Gln Asp Pro Tyr Gln Asn Arg
1               5

<210> SEQ ID NO 141
<211> LENGTH: 9
<212> TYPE: PRT
<213> ORGANISM: Artificial Sequence
<220> FEATURE:
<223> OTHER INFORMATION: ND2-Sharkey

<400> SEQUENCE: 141

Gly Phe Ser Gly Glu His Leu Gly Gly
1               5

<210> SEQ ID NO 142
<211> LENGTH: 24
<212> TYPE: DNA
<213> ORGANISM: Artificial Sequence
<220> FEATURE:
<223> OTHER INFORMATION: Reference of CHO-K1 ZFA36-ZFA36 target 1st site

<400> SEQUENCE: 142
accatcttcc actctgaaga tgga                                              24

<210> SEQ ID NO 143
<211> LENGTH: 24
<212> TYPE: DNA
<213> ORGANISM: Artificial Sequence
<220> FEATURE:
<223> OTHER INFORMATION: Reference of ZFA36-ZFA36 target 2nd site

<400> SEQUENCE: 143
accatcttca agagagaaga tggc                                              24

<210> SEQ ID NO 144
<211> LENGTH: 16
<212> TYPE: DNA
<213> ORGANISM: Artificial
<220> FEATURE:
<223> OTHER INFORMATION: FokI-cleaved CHO-K1 ZFA36-ZFA36 target 2nd site

<400> SEQUENCE: 144
accttaccat cttcaa                                                       16

<210> SEQ ID NO 145
<211> LENGTH: 18
<212> TYPE: DNA
<213> ORGANISM: Artificial
<220> FEATURE:
<223> OTHER INFORMATION: FokI-cleaved CHO-K1 ZFA36-ZFA36 target 2nd site

<400> SEQUENCE: 145
gagtgaagat ggcttaaa                                                     18

<210> SEQ ID NO 146
<211> LENGTH: 16
<212> TYPE: DNA
<213> ORGANISM: Artificial
<220> FEATURE:
<223> OTHER INFORMATION: ND2-cleaved CHO-K1 ZFA36-ZFA36 target 2nd site

<400> SEQUENCE: 146
```

```
accttaccat cttcaa                                        16

<210> SEQ ID NO 147
<211> LENGTH: 19
<212> TYPE: DNA
<213> ORGANISM: Artificial
<220> FEATURE:
<223> OTHER INFORMATION: ND2-cleaved CHO-K1 ZFA36-ZFA36 target 2nd site

<400> SEQUENCE: 147
agagagaaga tggcttaaa                                     19
```